(12) United States Patent
Haslett

(10) Patent No.: US 10,639,356 B2
(45) Date of Patent: May 5, 2020

(54) TREATMENT OF COGNITIVE IMPAIRMENT OF MUCOPOLYSACCHARIDOSIS TYPE IIIA BY INTRATHECAL DELIVERY OF HEPARAN N-SULFATASE

(71) Applicant: SHIRE HUMAN GENETIC THERAPIES, INC., Lexington, MA (US)

(72) Inventor: Patrick Anthony John Haslett, Lexington, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 19 days.

(21) Appl. No.: 15/746,192

(22) PCT Filed: Jul. 20, 2016

(86) PCT No.: PCT/US2016/043142
§ 371 (c)(1),
(2) Date: Jan. 19, 2018

(87) PCT Pub. No.: WO2017/015375
PCT Pub. Date: Jan. 26, 2017

(65) Prior Publication Data
US 2018/0207242 A1    Jul. 26, 2018

Related U.S. Application Data

(60) Provisional application No. 62/194,695, filed on Jul. 20, 2015.

(51) Int. Cl.
*A61K 38/46* (2006.01)
*A61P 3/00* (2006.01)
*A61K 9/00* (2006.01)

(52) U.S. Cl.
CPC ............ *A61K 38/46* (2013.01); *A61K 9/0019* (2013.01); *A61P 3/00* (2018.01); *C12Y 310/01001* (2013.01)

(58) Field of Classification Search
None
See application file for complete search history.

(56) References Cited

FOREIGN PATENT DOCUMENTS

WO    2014/089487 A1    6/2014

OTHER PUBLICATIONS

Anonymous, "NCT01047306 on Mar. 29, 2016: ClinicalTrials.gov Archive", (Mar. 29, 2016) URL: https://clinicaltrials.gov/archive/NCT01047306/2016_03_29, (Sep. 9, 2016).
(Continued)

*Primary Examiner* — Rebecca E Prouty
(74) *Attorney, Agent, or Firm* — Proskauer Rose LLP; Fangli Chen; Julio J. Mendez

(57) ABSTRACT

The present invention provides, among other things, effective treatment for Sanfilippo Syndrome Type A (MPS IIIA) based on intrathecal delivery of recombinant heparan N-sulfatase (HNS) enzyme. The present invention also includes methods of treating Sanfilippo Syndrome Type A (MPS IIIA) Syndrome by intrathecal administration of a recombinant HNS enzyme at a therapeutically effective dose and an administration interval for a period sufficient to decrease glycosaminoglycan (GAG) heparan sulfate level in the cerebrospinal fluid (CSF) relative to baseline (e.g., prior to treatment) as well as to improve, stabilize, or reduce decline of cognitive function, disability, behavior, quality of life and/or auditory brainstem response relative to baseline (e.g., prior to treatment).

14 Claims, 14 Drawing Sheets

(56) References Cited

OTHER PUBLICATIONS

Anonymous, "Safety, Tolerability, Ascending Dose and Dose Frequency Study of rhHNS Via an IDDD in MPS IIIA Patients—Full Text View—ClinicalTrials.gov", (Sep. 28, 2012), URL: https://clinicaltrials.gov/ct2/show/NCT01155778, (Sep. 9, 2016).

Buhrman et al., "Natural history of Sanfilippo syndrome type A", Journal of Inherited Metabolic Disease., NL, 37(3): 431-437 (2013).

Delaney et al., "Methods of Neurodevelopmental Assessment in Children with Neurodegenerative Disease: Sanfilippo Syndrome", JIMD Reports—vol. 11, Berlin, Heidelberg, Springer Berlin Heidelberg, vol. 13: 129-137 (2013).

Jones et al., "A phase ½ study of intrathecal heparan-N-sulfatase in patients with mucopolysaccharidosis IIIA", Molecular Genetics and Metabolism, Academic Press, Amsterdam, NL, 118(3): 198-205 (2016).

Shapiro et al., "Quantifying behaviors of children with Sanfilippo syndrome: The Sanfilippo Behavior Rating Scale", Molecular Genetics and Metabolism, Amsterdam, NL, 114(4): 594-598 (2015).

Bobo, R. H. et al., "Convection-enhanced delivery of macromolecules in the brain", Applied Biological Sciences, Proc. Natl. Acad. Sci. USA, Mar. 1994, vol. 91, pp. 2076-2080.

Nguyen, T. T. et al., "Convective distribution of macromolecules in the primate brain demonstrated using computerized tomography and magnetic resonance imaging", J. Neurosurg, (2003), vol. 98, pp. 584-590.

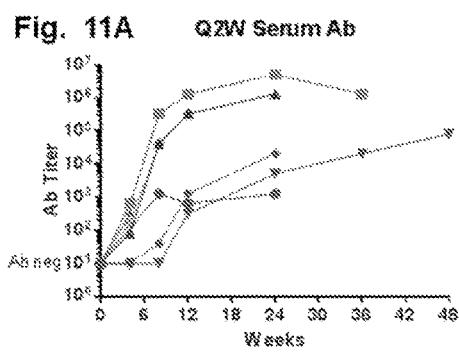
Fig. 11A  Q2W Serum Ab
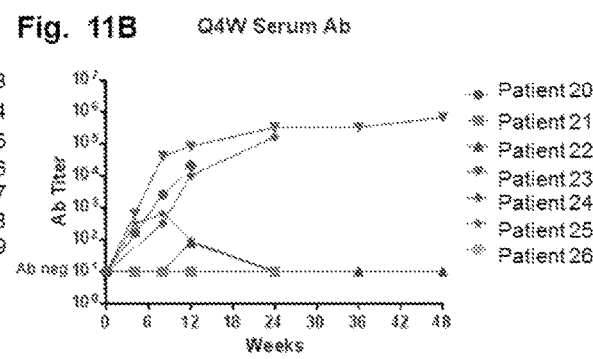
Fig. 11B  Q4W Serum Ab
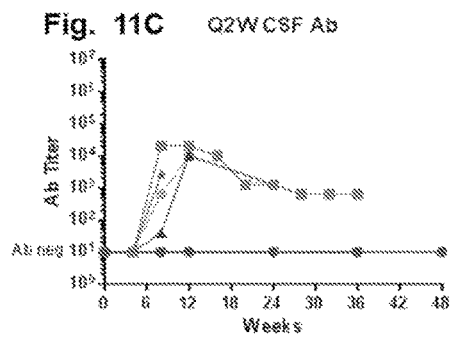
Fig. 11C  Q2W CSF Ab
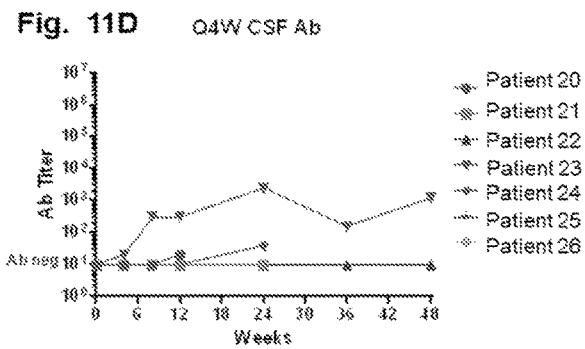
Fig. 11D  Q4W CSF Ab

TREATMENT OF COGNITIVE IMPAIRMENT OF MUCOPOLYSACCHARIDOSIS TYPE IIIA BY INTRATHECAL DELIVERY OF HEPARAN N-SULFATASE

CROSS REFERENCE TO RELATED APPLICATIONS

The present application is a 35 U.S.C. § 371 National Stage Application of International Application No. PCT/US16/43142, filed Jul. 20, 2016, which claims the benefit under 35 U.S.C. § 119(e) of U.S. Provisional Patent Application No. 62/194,695, filed Jul. 20, 2015, which is incorporated by reference in its entirety.

BACKGROUND

Glycosaminoglycans, with the exception of hyaluronic acid, are the degradation products of proteoglycans that exist in the extracellular matrix. Proteoglycans enter lysosomes for intracellular digestion, thereby generating glycosaminoglycans (GAGs).

The mucopolysaccharidoses (MPSs) are a group of lysosomal storage disorders caused by deficiency of enzymes catalyzing the stepwise degradation of GAGs (previously called mucopolysaccharides). An inability or decreased ability to degrade GAGs results in characteristic intralysosomal accumulation in all cells and increased excretion in urine of partially degraded GAGs. As substrates accumulate, the lysosomes swell and occupy more and more of the cytoplasm, affecting cellular organelles. The accumulation of GAGs ultimately results in cell, tissue, and organ dysfunction.

There are at least four different pathways of lysosomal degradation of GAGs, depending on the molecule to be degraded (e.g., dermatan sulfate, heparan sulfate, keratan sulfate, or chondroitin sulfate). The stepwise degradation of GAGs requires at least 10 different enzymes: four glycosidases, five sulfatases, and one nonhydrolytic transferase. Deficiencies of each one of these enzymes have been reported and result in seven different MPSs of various subtypes, all of which share several clinical features in variable degrees. Typical symptoms include organomegaly, dysostosis multiplex, and coarse facial features. Central nervous system function, including cognitive status, hearing, and vision, as well as cardiovascular function may also be affected. Many lysosomal storage disorders affect the nervous system and thus demonstrate unique challenges in treating these diseases with traditional therapies. There is often a large build-up of glycosaminoglycans (GAGs) in neurons and meninges of affected individuals, leading to various forms of CNS symptoms. To date, no CNS symptoms resulting from a lysosomal disorder has successfully been treated by any means available.

One such MPS disease is Mucopolysaccharidoses IIIA (MPS IIIA), which is also known as Sanfilippo Syndrome Type A. It is an autosomal recessive disease caused by a mutation in the SGSH gene, which encodes heparan N-sulfatase. Over 70 different mutations in SGSH have been described, all of which cause enzyme defects resulting in the accumulation of heparan sulfate. MPS IIIA occurs once in about every 100,000 live births, with no ethnic predisposition noted.

The primary accumulation of the GAG heparan sulfate triggers a poorly understood pathological cascade, primarily affecting the central nervous system (CNS). Mechanisms of pathology include secondary accumulation of toxic metabolites, neuroinflammation, disrupted growth factor signaling and dysregulated cell death. The clinical features of MPS IIIA are overwhelmingly neurological, with developmental delays in mid- to late-infancy often being the first manifestation of disease. Severe behavior disturbances are a frequent feature of middle childhood, with progressive dementia, emotional withdrawal and developmental regression. Afflicted individuals typically do not survive past their early twenties.

Enzyme replacement therapy (ERT) involves the systemic administration of natural or recombinantly-derived proteins and/or enzymes to a subject. Approved therapies are typically administered to subjects intravenously and are generally effective in treating the somatic symptoms of the underlying enzyme deficiency. As a result of the limited distribution of the intravenously administered protein and/or enzyme into the cells and tissues of the central nervous system (CNS), the treatment of diseases having a CNS etiology has been especially challenging because the intravenously administered proteins and/or enzymes do not adequately cross the blood-brain barrier (BBB).

The blood-brain barrier (BBB) is a structural system comprised of endothelial cells that functions to protect the central nervous system (CNS) from deleterious substances in the blood stream, such as bacteria, macromolecules (e.g., proteins) and other hydrophilic molecules, by limiting the diffusion of such substances across the BBB and into the underlying cerebrospinal fluid (CSF) and CNS.

There are several ways of circumventing the BBB to enhance brain delivery of a therapeutic agent including direct intra-cranial injection, transient permeabilization of the BBB, and modification of the active agent to alter tissue distribution. Direct injection of a therapeutic agent into brain tissue bypasses the vasculature completely, but suffers primarily from the risk of complications (infection, tissue damage, immune responsive) incurred by intra-cranial injections and poor diffusion of the active agent from the site of administration.

To date, direct administration of proteins into the brain substance has not achieved significant therapeutic effect due to diffusion barriers and the limited volume of therapeutic that can be administered. Convection-assisted diffusion has been studied via catheters placed in the brain parenchyma using slow, long-term infusions (Bobo, et al., Proc. Natl. Acad. Sci. U.S.A 91, 2076-2080 (1994); Nguyen, et al. J. Neurosurg. 98, 584-590 (2003)), but no approved therapies currently use this approach for long-term therapy. In addition, the placement of intracerebral catheters is very invasive and less desirable as a clinical alternative.

Intrathecal (IT) injection, or the administration of proteins to the cerebrospinal fluid (CSF), has also been attempted but has not yet yielded therapeutic success. A major challenge in this treatment has been quantifying clinical efficacy. Currently, there are no approved products for the treatment of brain genetic disease by administration directly to the CSF.

Thus, there remains a great need for effective and clinically quantifiable treatment of lysosomal storage diseases. More particularly, there is a great need for optimized therapeutic regimens of enzyme replace therapies capable of achieving measurable clinical efficacy, such as improvement, stabilization or reduction in decline of cognitive function, disability, behavior, quality of life and/or auditory brainstem response.

SUMMARY OF THE INVENTION

The present invention provides improved methods for safe and effective treatment of Mucopolysaccharidoses IIIA (MPS IIIA), which is also known as Sanfilippo Syndrome Type A. The present invention is, in part, based on a human clinical study demonstrating the safety, tolerability and efficacy in human MPS IIIA patients. In particular, the efficacy endpoints included decreased GAG levels in CSF as well as improvement, stabilization or reduction in decline of cognitive function, disability, behavior, quality of life and/or auditory brainstem response.

In one aspect, the invention provides methods of treating Sanfilippo Syndrome Type A (MPS IIIA) Syndrome comprising a step of administering intrathecally to a subject in need of treatment a recombinant heparan N-sulfatase (HNS) enzyme at a therapeutically effective dose and an administration interval for a period sufficient to improve, stabilize or reduce decline of one or more symptoms or features of Sanfilippo Syndrome Type A selected from the group consisting of cognitive function, total disability, behavior, quality of life, auditory brainstem response, and combinations thereof, relative to baseline.

In some embodiments, the therapeutically effective total enzyme dose ranges from about 10 mg to about 100 mg, e.g., from about 10 mg to about 90 mg, from about 10 mg to about 75 mg, from about 10 mg to about 50 mg, from about 10 mg to about 40 mg, from about 10 mg to about 30 mg, and from about 10 mg to about 20 mg. In some embodiments, the total enzyme dose is from about 40 mg to about 50 mg. In some embodiments, the therapeutically effective dose is or greater than about 10 mg per dose. In some embodiments, the therapeutically effective dose is or greater than about 45 mg per dose. In some embodiments, the therapeutically effective dose is or greater than about 90 mg per dose. In particular embodiments, the total enzyme dose is about 90 mg, about 45 mg or about 10 mg. In some embodiments, the total enzyme dose is administered as part of a treatment regimen. In some embodiments, the treatment regimen comprises intrathecal administration.

In some embodiments, the administration interval is monthly. In some embodiments, the administration interval is once every four weeks. In some embodiments, the administration interval is once every three weeks. In other embodiments, the administration interval is once every two weeks. In yet another embodiment, the administration interval is once every week.

In some embodiments, the symptoms or features of Sanfilippo Syndrome Type A are assessed one or more times during the treatment period. In some embodiments, the symptoms or features of Sanfilippo Syndrome Type A are assessed one or more times during treatment. In some embodiments, the administration is through intermittent or continuous access to an implanted intrathecal drug delivery device (IDDD).

In some embodiments the period is at least 1 month. In other embodiments, the period is at least 2 months, at least 3 months, at least 6 months or is at least 12 months.

In some embodiments, the cognitive function is assessed by the Bayley Scales of Infant Development (Third Edition) (BSID-III). In other embodiments, the intrathecal administration of the recombinant HNS enzyme results in an improved BSID-III development quotient relative to baseline. In another embodiment, the intrathecal administration of the recombinant HNS enzyme results in stabilization of a BSID-III development quotient relative to baseline. In some embodiments, the intrathecal administration of the recombinant HNS enzyme results in stabilization of a BSID-III development quotient relative to baseline for more than 1 month.

In some embodiments, the cognitive function is assessed by the Kaufman Assessment Battery for Children (Second Edition) (KABC-II). In other embodiments, the intrathecal administration of the recombinant HNS enzyme results in an improved KABC-II development quotient relative to baseline. In yet another embodiment, the intrathecal administration of the recombinant HNS enzyme results in stabilization of a KABC-II development quotient relative to baseline. In a further embodiment, the intrathecal administration of the recombinant HNS enzyme results in stabilization of a KABC-II development quotient relative to baseline for more than 1 month.

In some embodiments, the cognitive function is assessed by the Vineland Adaptive Behavior Scales Second Edition (VABS-II) test. In other embodiments, the intrathecal administration of the recombinant HNS enzyme results in an improved VABS-II development quotient relative to baseline. In yet another embodiment, the intrathecal administration of the recombinant HNS enzyme results in stabilization of a VABS-II development quotient relative to baseline. In a further embodiment, the intrathecal administration of the recombinant HNS enzyme results in stabilization of a VABS-II development quotient relative to baseline for more than 1 month.

In some embodiments, the total disability is assessed by the Four Point Scoring System/Total Disability Score (FPSS/TDS). In other embodiments, the intrathecal administration of the recombinant HNS enzyme results in an improved FPSS/TDS total disability score relative to baseline. In yet another embodiment, the intrathecal administration of the recombinant HNS enzyme results in stabilization of a FPSS/TDS total disability score relative to baseline. In a further embodiment, the intrathecal administration of the recombinant HNS enzyme results in stabilization of a FPSS/TDS total disability score relative to baseline for more than 1 month.

In some embodiments, the behavior is assessed by the Sanfilippo Behavior Rating Scale (SBRS). In other embodiments, the intrathecal administration of the recombinant HNS enzyme results in an improved SBRS score relative to baseline. In yet another embodiment, the intrathecal administration of the recombinant HNS enzyme results in stabilization of a SBRS score relative to baseline. In a further embodiment, the intrathecal administration of the recombinant HNS enzyme results in stabilization of a SBRS score relative to baseline for more than 1 month.

In some embodiments, the quality of life is assessed by a questionnaire or scale selected from the group consisting of the Child Health Questionnaire™ Parent Form 50 (CHQ 50), Infant Toddler Quality of Life Questionnaire™ (ITQOL), Children's Sleep Habits Rating Scale and combinations thereof. In other embodiments, the intrathecal administration of the recombinant HNS enzyme results in an improved quality of life score relative to baseline. In other embodiments, the intrathecal administration of the recombinant HNS enzyme results in stabilization of a quality of life score relative to baseline. In other embodiments, the intrathecal administration of the recombinant HNS enzyme results in stabilization of a quality of life score relative to baseline for more than 1 month.

In some embodiments, the auditory brainstem response (ABR) is selected from the group consisting of ABR latencies, ABR amplitude, ABR amplitude ratio, ABR log transformed latencies, ABR log transformed amplitude, ABR square-root transformed latencies, ABR square root transformed amplitude and combinations thereof. In other embodiments, the intrathecal administration of the recombinant HNS enzyme results in an improved auditory brainstem response score relative to baseline. In yet another embodiment, the intrathecal administration of the recombinant HNS enzyme results in stabilization of an auditory brainstem response score relative to baseline. In a further embodiment, the intrathecal administration of the recombinant HNS enzyme results in stabilization of an auditory brainstem response score relative to baseline for more than 1 month.

In some embodiments, the subject in need of treatment is at least 3 years old, is younger than 4 years old, is at least 12 years old or is at least 18 years old. In some embodiments, the intrathecal administration results in no serious adverse effects in the subject. In other embodiments, the intrathecal administration does not require an immunosuppressant. In yet another embodiment, the intrathecal administration is performed in conjunction with intravenous administration of the recombinant HNS enzyme.

In some embodiments, the method further comprises a step of adjusting the dose and/or administration interval for intrathecal administration based on improvement, stabilization or reduction in decline of one or more symptoms or features of Sanfilippo Syndrome Type A selected from the group consisting of cognitive function, total disability, behavior, quality of life, auditory brainstem response, and combinations thereof, relative to baseline.

In another embodiment, the step of adjusting comprises increasing the therapeutically effective dose for intrathecal administration if the improvement, stabilization or reduction in decline of one or more symptoms or features of Sanfilippo Syndrome Type A selected from the group consisting of cognitive function, total disability, behavior, quality of life, auditory brainstem response, and combinations thereof, fails to decrease relative to baseline after 4 doses.

In another aspect, the invention provides a recombinant heparan N-sulfatase (HNS) enzyme for use in a method of treating Sanfilippo Syndrome Type A (MPS IIIA) wherein the method comprises a step of administering intrathecally to a subject in need of treatment the recombinant HNS enzyme at a therapeutically effective dose and an administration interval for a treatment period sufficient to improve, stabilize or reduce decline of one or more symptoms or features of Sanfilippo Syndrome Type A selected from the group consisting of cognitive function, total disability, behavior, quality of life, auditory brainstem response, and combinations thereof, relative to baseline.

In another aspect, the invention provides for the use of a recombinant heparan N-sulfatase (HNS) enzyme in the manufacture of a medicament for treating Sanfilippo Syndrome Type A (MPS IIIA) wherein the treatment comprises a step of administering intrathecally to a subject in need of treatment the recombinant HNS enzyme at a therapeutically effective dose and an administration interval for a treatment period sufficient to improve, stabilize or reduce decline of one or more symptoms or features of Sanfilippo Syndrome Type A selected from the group consisting of cognitive function, total disability, behavior, quality of life, auditory brainstem response, and combinations thereof, relative to baseline.

In some embodiments, the treatment comprises administering intrathecally to a subject in need of treatment the recombinant HNS enzyme at a first therapeutically effective dose; and administering intravenously to the subject the recombinant HNS enzyme at a second therapeutically effective dose for a treatment period sufficient to improve, stabilize or reduce decline of one or more symptoms or features of Sanfilippo Syndrome Type A selected from the group consisting of cognitive function, total disability, behavior, quality of life, auditory brainstem response, and combinations thereof, relative to baseline.

In some embodiments, the subject has cognitive impairment. In other embodiments, cognitive function is improved or stabilized in a subject having Sanfilippo Syndrome Type A (MPS IIIA). In some particular embodiments, the subject has a pre-treatment DQ score at or greater than 60.

In various embodiments, the present invention includes a stable formulation of any of the embodiments described herein, wherein the HNS protein comprises an amino acid sequence of SEQ ID NO:1. In some embodiments, the HNS protein comprises an amino acid sequence at least 60%, 65%, 70%, 75%, 80%, 85%, 90%, 95%, or 98% identical to SEQ ID NO:1. In some embodiments, the stable formulation of any of the embodiments described herein includes a salt. In some embodiments, the salt is NaCl. In some embodiments, the NaCl is present as a concentration ranging from approximately 0-300 mM (e.g., 0-250 mM, 0-200 mM, 0-150 mM, 0-100 mM, 0-75 mM, 0-50 mM, or 0-30 mM). In some embodiments, the NaCl is present at a concentration ranging from approximately 135-155 mM. In some embodiments, the NaCl is present at a concentration of approximately 145 mM.

In some embodiments, intrathecal administration of recombinant HNS enzyme according to the invention results in maintain cognitive status, arrest cognitive decline or improve cognitive performance. Without wishing to be bound by any particular theory, it is thought that starting treatment before the onset of significant cognitive decline is important for measurable improvements, stabilizations or reduced declines in cognitive functions relative to controls (e.g., baseline pre-treatment assessment or measurement).

Thus, embodiments of the present invention prove, in part, methods of treating lysosomal storage diseases by intrathecal administration of human recombinant sulfatases at a therapeutically effective dose and an administration interval for a period sufficient to improve, stabilize or reduce declining of one or more symptoms or features relative to a control. In particular embodiments, the sulfatase is heparan N-sulfatase (HNS) enzyme. In some embodiments, methods of treating lysosomal storage diseases by intrathecal administration of human recombinant sulfatases comprise administering the therapeutically effective total enzyme dosages disclosed herein (e.g., greater than 10 mg per dose, greater than 45 mg per dose, or greater than 90 mg per dose) at the administration intervals disclosed herein (e.g., monthly, once every two weeks, once every week for a period sufficient to improve, stabilize or reduce declining of one or more cognitive functions relative to a control or to pretreatment levels.

BRIEF DESCRIPTION OF THE DRAWINGS

The drawings are for illustration purposes only, not for limitation.

FIG. 11 shows the anti-rhHNS antibody status in the serum and cerebrospinal fluid (CSF) of study subjects was monitored throughout the study. For plot purposes, Ab negative is assigned an artificial titer of 10. (45 mg/14 days—FIG. 11A, 11C, 45 mg/28 days—FIG. 11B, 11D).

DEFINITIONS

Figure 1A:
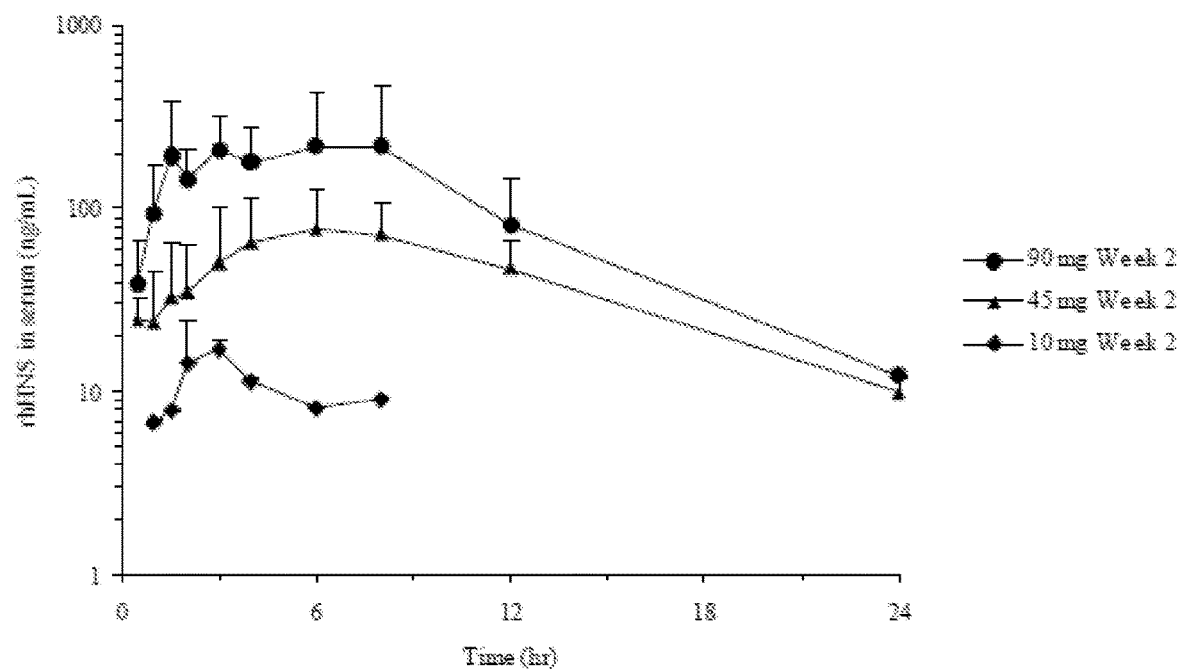
FIG. 1A shows dose dependent serum rhHNS concentration collected at Week 2 (Baseline) immediately prior to IT injection and over 24 hours following completion of IT injection.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" or "ameliorate" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Bulking agent: As used herein, the term "bulking agent" refers to a compound which adds mass to the lyophilized mixture and contributes to the physical structure of the lyophilized cake (e.g., facilitates the production of an essentially uniform lyophilized cake which maintains an open pore structure). Exemplary bulking agents include mannitol, glycine, sodium chloride, hydroxyethyl starch, lactose, sucrose, trehalose, polyethylene glycol and dextran.

Cerebroanatomical Marker: The term "Cerebroanatomical Marker" as used herein refers to any anatomical feature of a brain. In some embodiments, a cerebroanatomical marker comprises, but is not limited to, any portion of the central nervous system that is enclosed within the cranium, continuous with the spinal cord and composed of gray matter and white matter.

Cation-independent mannose-6-phosphate receptor (CI-MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose-6-phosphates, the CI-MPR also binds other proteins including IGF-II. The CI-MPR is also known as "M6P/IGF-II receptor," "CI-MPR/IGF-II receptor," "IGF-II receptor" or "IGF2 Receptor." These terms and abbreviations thereof are used interchangeably herein.

Concurrent immunosuppressant therapy: As used herein, the term "concurrent immunosuppressant therapy" includes any immunosuppressant therapy used as pre-treatment, pre-conditioning or in parallel to a treatment method.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Diagnosis: As used herein, the term "diagnosis" refers to a process aimed at determining if an individual is afflicted with a disease or ailment. In the context of the present invention, "diagnosis of Sanfilippo syndrome" refers to a process aimed at one or more of: determining if an individual is afflicted with Sanfilippo syndrome, identifying a Sanfilippo syndrome subtype (i.e., subtype A, B, C or D), and determining the stage of the disease (e.g., early Sanfilippo syndrome or late Sanfilippo syndrome).

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic protein for the patient to be treated. Each unit contains a predetermined quantity of active material calculated to produce the desired therapeutic effect. It will be understood, however, that the total dosage of the composition will be decided by the attending physician within the scope of sound medical judgment.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodstream. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Effective amount: As used herein, the term "effective amount" refers to an amount of a compound or agent that is sufficient to fulfill its intended purpose(s). In the context of the present invention, the purpose(s) may be, for example: to modulate the expression of at least one inventive biomarker; and/or to delay or prevent the onset of Sanfilippo syndrome; and/or to slow down or stop the progression, aggravation, or deterioration of the symptoms of Sanfilippo syndrome; and/or to alleviate one or more symptoms associated with Sanfilippo syndrome; and/or to bring about amelioration of the symptoms of Sanfilippo syndrome, and/or to cure Sanfilippo syndrome.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a disease.

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Linker: As used herein, the term "linker" refers to, in a fusion protein, an amino acid sequence other than that appearing at a particular position in the natural protein and is generally designed to be flexible or to interpose a structure, such as an α-helix, between two protein moieties. A linker is also referred to as a spacer.

Lyoprotectant: As used herein, the term "lyoprotectant" refers to a molecule that prevents or reduces chemical and/or physical instability of a protein or other substance upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate: a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In some embodiments, a lyoprotectant is a non-reducing sugar, such as trehalose or sucrose.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Sample: As used herein, the term "Sample" encompasses any sample obtained from a biological source. The terms "biological sample" and "sample" are used interchangeably. A biological sample can, by way of non-limiting example, include cerebrospinal fluid (CSF), blood, amniotic fluid, sera, urine, feces, epidermal sample, skin sample, cheek swab, sperm, amniotic fluid, cultured cells, bone marrow sample and/or chorionic villi. Convenient biological samples may be obtained by, for example, scraping cells from the surface of the buccal cavity. Cell cultures of any biological samples can also be used as biological samples, e.g., cultures of chorionic villus samples and/or amniotic fluid cultures such as amniocyte cultures. A biological sample can also be, e.g., a sample obtained from any organ or tissue (including a biopsy or autopsy specimen), can comprise cells (whether primary cells or cultured cells), medium conditioned by any cell, tissue or organ, tissue culture. In some embodiments, biological samples suitable for the invention are samples which have been processed to released, or otherwise make available, a nucleic acid for detection as described herein. Suitable biological samples may be obtained from a stage of life such as a fetus, young adult, adult (e.g., pregnant women), and the like. Fixed or frozen tissues also may be used.

Soluble: As used herein, the term "soluble" refers to the ability of a therapeutic agent to form a homogenous solution. In some embodiments, the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, the pharmaceutical compositions are formulated such that calcium salts are excluded from such compositions. In some embodiments, therapeutic agents in accordance with the present invention are soluble in its corresponding pharmaceutical composition. It will be appreciated that, while isotonic solutions are generally preferred for parenterally administered drugs, the use of isotonic solutions may limit adequate solubility for some therapeutic agents and, in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated in monkeys. For example, the most common approved CNS bolus formulation composition is saline (150 mM NaCl in water).

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., recombinant proteins). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measured by formation of high molecular weight (HMW) aggregates, loss of enzyme activity, generation of peptide fragments and shift of charge profiles.

Subject: As used herein, the term "subject" means any mammal, including humans. In certain embodiments of the present invention the subject is an adult, an adolescent or an infant. In certain embodiments of the present invention the subject is approximately 3 years to 22 years in age. In certain embodiments of the present invention, the subject is less than about 10 years of age. In certain embodiments of the present invention, the subject is approximately 3 years to 10 years of age. In certain embodiments of the present invention, the subject approximately 10 years of age. In certain embodiments of the invention, the subject is less than 3 years of age. In certain embodiments of the invention, the subject is approximately 1 year to 3 years of age. Also contemplated by the present invention are the administration of the pharmaceutical compositions and/or performance of the methods of treatment in-utero.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, and/or condition has been diagnosed with or displays one or more symptoms of the disease, disorder, and/or condition.

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Therapeutic moiety: As used herein, the term "therapeutic moiety" refers to a portion of a molecule that renders the therapeutic effect of the molecule. In some embodiments, a therapeutic moiety is a polypeptide having therapeutic activity.

Therapeutically effective amount: As used herein, the term "therapeutically effective amount" refers to an amount of a therapeutic protein (e.g., replacement enzyme) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset or progression of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Tolerable: As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Hunters syndrome, Sanfilippo A syndrome, Sanfilippo B syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION OF THE INVENTION

Among other things, the present invention provides methods for treating Mucopolysaccharidosis IIIA (MPS IIIA) based on intrathecal administration of recombinant replacement heparan N-sulfatase (HNS) enzyme at a therapeutically effective dose and an administration interval. In some embodiments, the replacement enzyme is administered for a period sufficient to decrease glycosaminoglycan (GAG) heparan sulfate level in the cerebrospinal fluid (CSF) relative to base line (e.g., prior to treatment with replacement enzyme). In another embodiment, the replacement enzyme is administered for a period sufficient to improve, stabilize or reduce decline of cognitive function, disability, behavior, quality of life and/or auditory brainstem response in patients with Sanfilippo Type A relative to baseline (e.g., prior to treatment with replacement enzyme).

Various aspects of the invention are described in detail in the following sections. The use of sections is not meant to limit the invention. Each section can apply to any aspect of the invention. In this application, the use of "or" means "and/or" unless stated otherwise.

Recombinant Heparan-N-Sulfatase (HNS) Enzymes

A suitable HNS protein for the present invention can be any molecule or a portion of a molecule that can substitute for naturally-occurring Heparan-N-Sulfatase (HNS) protein activity or rescue one or more phenotypes or symptoms associated with HNS-deficiency. In some embodiments, a replacement enzyme suitable for the invention is a polypeptide having an N-terminus and a C-terminus and an amino acid sequence substantially similar or identical to mature human HNS protein.

Typically, human HNS is produced as a precursor molecule that is processed to a mature form. This process generally occurs by removing the 20 amino acid signal peptide. Typically, the precursor form is also referred to as full-length precursor or full-length HNS protein, which contains 502 amino acids. The N-terminal 20 amino acids are cleaved, resulting in a mature form that is 482 amino acids in length. Thus, it is contemplated that the N-terminal 20 amino acids is generally not required for the HNS protein activity. The amino acid sequences of the mature form (SEQ ID NO:1) and full-length precursor (SEQ ID NO:2) of a typical wild-type or naturally-occurring human HNS protein are shown in Table 1.

TABLE 1

| Heparan N-Sulfatase | |
|---|---|
| Mature Form | RPRNALLLLADDGGFESGAYNNSAIATPHLDALARRSLLFRNAFTS VSSCSPSRASLLTGLPQHQNGMYGLHQDVHHFNSFDKVRSLPLLL SQAGVRTGIIGKKHVGPETVYPFDFAYTEENGSVLQVGRNITRIKL LVRKFLQTQDDRPFFLYVAFHDPHRCGHSQPQYGTFCEKFGNGES GMGRIPDWTPQAYDPLDVLVPYFVPNTPAARADLAAQYTTVGRM DQGVGLVLQELRDAGVLNDTLVIFTSDNGIPFPSGRTNLYWPGTA EPLLVSSPEHPKRWGQVSEAYVSLLDLTPTILDWFSIPYPSYAIFGS KTIHLTGRSLLPALEAEPLWATVFGSQSHHEVTMSYPMRSVQHRH FRLVHNLNFKMPFPIDQDFYVSPTFQDLLNRTTAGQPTGWYKDLR HYYYRARWELYDRSRDPHETQNLATDPRFAQLLEMLRDQLAKW QWETHDPWVCAPDGVLEEKLSPQCQPLHNEL (SEQ ID NO: 1) |
| Full-Length Precursor | MSCPVPACCALLLVLGLCRARPRNALLLLADDGGFESGAYNNSAI ATPHLDALARRSLLFRNAFTSVSSCSPSRASLLTGLPQHQNGMYGL HQDVHHFNSFDKVRSLPLLLSQAGVRTGIIGKKHVGPETVYPFDFA YTEENGSVLQVGRNITRIKLLVRKFLQTQDDRPFFLYVAFHDPHRC GHSQPQYGTFCEKFGNGESGMGRIPDWTPQAYDPLDVLVPYFVPN TPAARADLAAQYTTVGRMDQGVGLVLQELRDAGVLNDTLVIFTS DNGIPFPSGRTNLYWPGTAEPLLVSSPEHPKRWGQVSEAYVSLLD LTPTILDWFSIPYPSYAIFGSKTIHLTGRSLLPALEAEPLWATVFGSQ SHHEVTMSYPMRSVQHRHFRLVHNLNFKMPFPIDQDFYVSPTFQD LLNRTTAGQPTGWYKDLRHYYYRARWELYDRSRDPHETQNLAT DPRFAQLLEMLRDQLAKWQWETHDPWVCAPDGVLEEKLSPQCQ PLHNEL (SEQ ID NO: 2) |

Thus, in some embodiments, a therapeutic moiety suitable for the present invention is mature human HNS protein (SEQ ID NO:1). In some embodiments, a suitable therapeutic moiety may be a homologue or an analogue of mature human HNS protein. For example, a homologue or an analogue of mature human HNS protein may be a modified mature human HNS protein containing one or more amino acid substitutions, deletions, and/or insertions as compared to a wild-type or naturally-occurring HNS protein (e.g., SEQ ID NO:1), while retaining substantial HNS protein activity. Thus, in some embodiments, a therapeutic moiety suitable for the present invention is substantially homologous to mature human HNS protein (SEQ ID NO:1). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a therapeutic moiety suitable for the present invention is substantially identical to mature human HNS protein (SEQ ID NO:1). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a therapeutic moiety suitable for the present invention contains a fragment or a portion of mature human HNS protein.

Alternatively, a therapeutic moiety suitable for the present invention is full-length HNS protein. In some embodiments, a suitable therapeutic moiety may be a homologue or an analogue of full-length human HNS protein. For example, a homologue or an analogue of full-length human HNS protein may be a modified full-length human HNS protein containing one or more amino acid substitutions, deletions, and/or insertions as compared to a wild-type or naturally-occurring full-length HNS protein (e.g., SEQ ID NO:2), while retaining substantial HNS protein activity. Thus, in some embodiments, a therapeutic moiety suitable for the present invention is substantially homologous to full-length human HNS protein (SEQ ID NO:2). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a therapeutic moiety suitable for the present invention is substantially identical to SEQ ID NO:2. In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a therapeutic moiety suitable for the present invention contains a fragment or a portion of full-length human HNS protein. As used herein, a full-length HNS protein typically contains signal peptide sequence.

A replacement enzyme suitable for the present invention may be produced by any available means. For example, replacement enzymes may be recombinantly produced by utilizing a host cell system engineered to express a replacement enzyme-encoding nucleic acid. Alternatively or additionally, replacement enzymes may be produced by activating endogenous genes. Alternatively or additionally, replacement enzymes may be partially or fully prepared by chemical synthesis. Alternatively or additionally, replacements enzymes may also be purified from natural sources.

Where enzymes are recombinantly produced, any expression system can be used. To give but a few examples, known expression systems include, for example, egg, baculovirus, plant, yeast, or mammalian cells.

In some embodiments, enzymes suitable for the present invention are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells+/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, inventive methods according to the present invention are used to deliver replacement enzymes produced from human cells. In some embodiments, inventive methods according to the present invention are used to deliver replacement enzymes produced from CHO cells.

In some embodiments, replacement enzymes delivered using a method of the invention contain a moiety that binds to a receptor on the surface of brain cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. In some embodiments, a replacement enzyme suitable for the present invention contains M6P residues on the surface of the protein. In some embodiments, a replacement enzyme suitable for the present invention may contain bis-phosphorylated oligosaccharides which have higher binding affinity to the CI-MPR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme. While such bis-phosphorylated oligosaccharides may be naturally present on the enzyme, it should be noted that the enzymes may be modified to possess such oligosaccharides. For example, suitable replacement enzymes may be modified by certain enzymes which are capable of catalyzing the transfer of N-acetylglucosamine-L-phosphate from UDP-GlcNAc to the 6' position of α-1,2-linked mannoses on lysosomal enzymes. Methods and compositions for producing and using such enzymes are described by, for example, Canfield et al. in U.S. Pat. Nos. 6,537,785, and 6,534,300, each incorporated herein by reference.

In some embodiments, replacement enzymes for use in the present invention may be conjugated or fused to a lysosomal targeting moiety that is capable of binding to a receptor on the surface of brain cells. A suitable lysosomal targeting moiety can be IGF-I, IGF-II, RAP, p97, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence).

In some embodiments, replacement enzymes suitable for the present invention have not been modified to enhance delivery or transport of such agents across the BBB and into the CNS.

In some embodiments, a therapeutic protein includes a targeting moiety (e.g., a lysosome targeting sequence) and/or a membrane-penetrating peptide. In some embodiments, a targeting sequence and/or a membrane-penetrating peptide is an intrinsic part of the therapeutic moiety (e.g., via a chemical linkage, via a fusion protein). In some embodiments, a targeting sequence contains a mannose-6-phosphate moiety. In some embodiments, a targeting sequence contains an IGF-I moiety. In some embodiments, a targeting sequence contains an IGF-II moiety.

Formulations

In some embodiments, desired enzymes are delivered in stable formulations for intrathecal delivery. Certain embodiments of the invention are based, at least in part, on the discovery that various formulations disclosed herein facilitate the effective delivery and distribution of one or more therapeutic agents (e.g., an HNS enzyme) to targeted tissues, cells and/or organelles of the CNS. Among other things, formulations described herein are capable of solubilizing high concentrations of therapeutic agents (e.g., an HNS enzyme) and are suitable for the delivery of such therapeutic agents to the CNS of subjects for the treatment of diseases having a CNS component and/or etiology (e.g., Sanfilippo A Syndrome). The compositions described herein are further characterized by improved stability and improved tolerability when administered to the CNS of a subject (e.g., intrathecally) in need thereof.

In some embodiments, formulations for CNS delivery have been formulated such that they are capable of stabilizing, or alternatively slowing or preventing the degradation, of a therapeutic agent formulated therewith (e.g., an HNS enzyme). As used herein, the term "stable" refers to the ability of the therapeutic agent (e.g., an HNS enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., preferably for at least 1, 3, 6, 12, 18, 24, 30, 36 months or more). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measured by formation of high molecular weight (HMW) aggregates, loss of enzyme activity, generation of peptide fragments and shift of charge profiles.

Stability of the therapeutic agent is of particular importance. Stability of the therapeutic agent may be further assessed relative to the biological activity or physiochemical integrity of the therapeutic agent over extended periods of time. For example, stability at a given time point may be compared against stability at an earlier time point (e.g., upon formulation day 0) or against unformulated therapeutic agent and the results of this comparison expressed as a percentage. Preferably, the pharmaceutical compositions of the present invention maintain at least 100%, at least 99%, at least 98%, at least 97% at least 95%, at least 90%, at least 85%, at least 80%, at least 75%, at least 70%, at least 65%, at least 60%, at least 55% or at least 50% of the therapeutic agent's biological activity or physiochemical integrity over an extended period of time (e.g., as measured over at least about 6-12 months, at room temperature or under accelerated storage conditions).

In some embodiments, therapeutic agents (e.g., desired enzymes) are soluble in formulations of the present invention. The term "soluble" as it relates to the therapeutic agents of the present invention refer to the ability of such therapeutic agents to form a homogenous solution. Preferably the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts.) In some embodiments, the pharmaceutical compositions are formulated such that calcium salts are excluded from such compositions.

Suitable formulations, in either aqueous, pre-lyophilized, lyophilized or reconstituted form, may contain a therapeutic agent of interest at various concentrations. In some embodiments, formulations may contain a protein or therapeutic agent of interest at a concentration in the range of about 0.1 mg/ml to 100 mg/ml (e.g., about 0.1 mg/ml to 90 mg/ml, about 0.1 mg/ml to 80 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 60 mg/ml, about 0.1 mg/ml to 50 mg/ml, about 0.1 mg/ml to 45 mg/ml, about 0.1 mg/ml to 40 mg/ml, about 0.1 mg/ml to 35 mg/ml, about 0.1 mg/ml to 30 mg/ml, about 0.1 mg/ml to 25 mg/ml, about 0.1 mg/ml to 20 mg/ml, about 0.1 mg/ml to 15 mg/ml, about 0.1 mg/ml to 10 mg/ml, about 0.1 mg/ml to 5 mg/ml, about 1 mg/ml to 10 mg/ml, about 1 mg/ml to 20 mg/ml, about 1 mg/ml to 40 mg/ml, about 5 mg/ml to 100 mg/ml, about 5 mg/ml to 50 mg/ml, or about 5 mg/ml to 25 mg/ml). In some embodiments, formulations according to the invention may contain a therapeutic agent at a concentration of approximately 1 mg/ml, 5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml, or 100 mg/ml.

The formulations of the present invention are characterized by their tolerability either as aqueous solutions or as reconstituted lyophilized solutions. As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Many therapeutic agents, and in particular the proteins and enzymes of the present invention, require controlled pH and specific excipients to maintain their solubility and stability in the pharmaceutical compositions of the present invention. Table 2 below identifies typical exemplary aspects of protein formulations considered to maintain the solubility and stability of the protein therapeutic agents of the present invention.

TABLE 2

Exemplary pH and excipients

| Parameter | Typical Range/Type | Rationale |
| --- | --- | --- |
| pH | 4 to 8.0 | For stability<br>Sometimes also for solubility |
| Buffer type | acetate, succinate, citrate, histidine, phosphate or Tris | To maintain optimal pH<br>May also affect stability |
| Buffer concentration | 5-50 mM | To maintain pH<br>May also stabilize or add ionic strength |
| Tonicifier | NaCl, sugars, mannitol | To render iso-osmotic or isotonic solutions |
| Surfactant | Polysorbate 20, polysorbate 80 | To stabilize against interfaces and shear |
| Other | Amino acids (e.g. arginine) at tens to hundreds of mM | For enhanced solubility or stability |

Buffers

The pH of the formulation is an additional factor which is capable of altering the solubility of a therapeutic agent (e.g., an enzyme or protein) in an aqueous formulation or for a pre-lyophilization formulation. Accordingly the formulations of the present invention preferably comprise one or more buffers. In some embodiments the aqueous formulations comprise an amount of buffer sufficient to maintain the optimal pH of said composition between about 4.0-8.0 (e.g., about 4.0, 4.5, 5.0, 5.5, 6.0, 6.2, 6.4, 6.5, 6.6, 6.8, 7.0, 7.5, or 8.0). In some embodiments, the pH of the formulation is between about 5.0-7.5, between about 5.5-7.0, between about 6.0-7.0, between about 5.5-6.0, between about 5.5-6.5, between about 5.0-6.0, between about 5.0-6.5 and between about 6.0-7.5. Suitable buffers include, for example acetate, citrate, histidine, phosphate, succinate, tris(hydroxymethyl) aminomethane ("Tris") and other organic acids. The buffer concentration and pH range of the pharmaceutical compositions of the present invention are factors in controlling or adjusting the tolerability of the formulation. In some embodiments, a buffering agent is present at a concentration ranging between about 1 mM to about 150 mM, or between about 10 mM to about 50 mM, or between about 15 mM to about 50 mM, or between about 20 mM to about 50 mM, or between about 25 mM to about 50 mM. In some embodiments, a suitable buffering agent is present at a concentration of approximately 1 mM, 5 mM, 10 mM, 15 mM, 20 mM, 25 mM, 30 mM, 35 mM, 40 mM, 45 mM 50 mM, 75 mM, 100 mM, 125 mM or 150 mM.

Tonicity

In some embodiments, formulations, in either aqueous, pre-lyophilized, lyophilized or reconstituted form, contain an isotonicity agent to keep the formulations isotonic. Typically, by "isotonic" is meant that the formulation of interest has essentially the same osmotic pressure as human blood. Isotonic formulations will generally have an osmotic pressure from about 240 mOsm/kg to about 350 mOsm/kg. Isotonicity can be measured using, for example, a vapor pressure or freezing point type osmometers. Exemplary isotonicity agents include, but are not limited to, glycine, sorbitol, mannitol, sodium chloride and arginine. In some embodiments, suitable isotonic agents may be present in aqueous and/or pre-lyophilized formulations at a concentration from about 0.01-5% (e.g., 0.05, 0.1, 0.15, 0.2, 0.3, 0.4, 0.5, 0.75, 1.0, 1.25, 1.5, 2.0, 2.5, 3.0, 4.0 or 5.0%) by weight. In some embodiments, formulations for lyophilization contain an isotonicity agent to keep the pre-lyophilization formulations or the reconstituted formulations isotonic.

While generally isotonic solutions are preferred for parenterally administered drugs, the use of isotonic solutions may change solubility for some therapeutic agents and in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated. The most common approved CNS bolus formulation composition is saline (about 150 mM NaCl in water).

Stabilizing Agents

In some embodiments, formulations may contain a stabilizing agent, or lyoprotectant, to protect the protein. Typically, a suitable stabilizing agent is a sugar, a non-reducing sugar and/or an amino acid. Exemplary sugars include, but are not limited to, dextran, lactose, mannitol, mannose, sorbitol, raffinose, sucrose and trehalose. Exemplary amino acids include, but are not limited to, arginine, glycine and methionine. Additional stabilizing agents may include sodium chloride, hydroxyethyl starch and polyvinylpyrolidone. The amount of stabilizing agent in the lyophilized formulation is generally such that the formulation will be isotonic. However, hypertonic reconstituted formulations may also be suitable. In addition, the amount of stabilizing agent must not be too low such that an unacceptable amount of degradation/aggregation of the therapeutic agent occurs. Exemplary stabilizing agent concentrations in the formulation may range from about 1 mM to about 400 mM (e.g., from about 30 mM to about 300 mM, and from about 50 mM to about 100 mM), or alternatively, from 0.1% to 15% (e.g., from 1% to 10%, from 5% to 15%, from 5% to 10%) by weight. In some embodiments, the ratio of the mass amount of the stabilizing agent and the therapeutic agent is about 1:1. In other embodiments, the ratio of the mass amount of the stabilizing agent and the therapeutic agent can be about 0.1:1, 0.2:1, 0.25:1, 0.4:1, 0.5:1, 1:1, 2:1, 2.6:1, 3:1, 4:1, 5:1, 10;1, or 20:1. In some embodiments, suitable for lyophilization, the stabilizing agent is also a lyoprotectant.

In some embodiments, liquid formulations suitable for the present invention contain amorphous materials. In some embodiments, liquid formulations suitable for the present invention contain a substantial amount of amorphous materials (e.g., sucrose-based formulations). In some embodiments, liquid formulations suitable for the present invention contain partly crystalline/partly amorphous materials.

Bulking Agents

In some embodiments, suitable formulations for lyophilization may further include one or more bulking agents. A "bulking agent" is a compound which adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, trehalose, hydroxyethyl starch. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%).

Surfactants

In some embodiments, it is desirable to add a surfactant to formulations. Exemplary surfactants include nonionic surfactants such as Polysorbates (e.g., Polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristarnidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68, etc.). Typically, the amount of surfactant added is such that it reduces aggregation of the protein and minimizes the formation of particulates or effervescences. For example, a surfactant may be present in a formulation at a concentration from about 0.001-0.5% (e.g., about 0.001-0.4%, 0.001-0.3%, 0.001-0.2%, 0.001-0.1%, 0.001-0.05%, 0.001-0.04%, 0.001-0.03%, 0.001-0.02%, 0.001-0.01%, 0.002-0.05%, 0.003-0.05%, 0.004-0.05%, 0.005-0.05%, or 0.005-0.01%). In particular, a surfactant may be present in a formulation at a concentration of approximately 0.001%, 0.002%, 0.003%, 0.004%, 0.005%, 0.006%, 0.007%, 0.008%, 0.009%, 0.01%, 0.02%, 0.03%, 0.04%, 0.05%, 0.1%, 0.2%, 0.3%, 0.4%, or 0.5%, etc. Alternatively, or in addition, the surfactant may be added to the lyophilized formulation, pre-lyophilized formulation and/or the reconstituted formulation.

Other pharmaceutically acceptable carriers, excipients or stabilizers such as those described in Remington's Pharmaceutical Sciences 16th edition, Osol, A. Ed. (1980) may be included in the formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include, but are not limited to, additional buffering agents; preservatives; co-solvents; antioxidants including ascorbic acid and methionine; chelating agents such as EDTA; metal complexes (e.g., Zn-protein complexes); biodegradable polymers such as polyesters; and/or salt-forming counterions such as sodium.

Formulations, in either aqueous, pre-lyophilized, lyophilized or reconstituted form, in accordance with the present invention can be assessed based on product quality analysis, reconstitution time (if lyophilized), quality of reconstitution (if lyophilized), high molecular weight, moisture, and glass transition temperature. Typically, protein quality and product analysis include product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC (RP-HPLC), multi-angle light scattering (MALS), fluorescence, ultraviolet absorption, nephelometry, capillary electrophoresis (CE), SDS-PAGE, and combinations thereof. In some embodiments, evaluation of product in accordance with the present invention may include a step of evaluating appearance (either liquid or cake appearance).

Generally, formulations (lyophilized or aqueous) can be stored for extended periods of time at room temperature. Storage temperature may typically range from 0° C. to 45° C. (e.g., 4° C., 20° C., 25° C., 45° C. etc.). Formulations may be stored for a period of months to a period of years. Storage time generally will be 24 months, 12 months, 6 months, 4.5 months, 3 months, 2 months or 1 month. Formulations can be stored directly in the container used for administration, eliminating transfer steps.

Formulations can be stored directly in the lyophilization container (if lyophilized), which may also function as the reconstitution vessel, eliminating transfer steps. Alternatively, lyophilized product formulations may be measured into smaller increments for storage. Storage should generally avoid circumstances that lead to degradation of the proteins, including but not limited to exposure to sunlight, UV radiation, other forms of electromagnetic radiation, excessive heat or cold, rapid thermal shock, and mechanical shock.

Lyophilization

Inventive methods in accordance with the present invention can be utilized to lyophilize any materials, in particular, therapeutic agents. Typically, a pre-lyophilization formulation further contains an appropriate choice of excipients or other components such as stabilizers, buffering agents, bulking agents, and surfactants to prevent the compound of interest from degradation (e.g., protein aggregation, deamidation, and/or oxidation) during freeze-drying and storage. The formulation for lyophilization can include one or more additional ingredients including lyoprotectants or stabilizing agents, buffers, bulking agents, isotonicity agents and surfactants.

After the substance of interest and any additional components are mixed together, the formulation is lyophilized Lyophilization generally includes three main stages: freezing, primary drying and secondary drying. Freezing is necessary to convert water to ice or some amorphous formulation components to the crystalline form. Primary drying is the process step when ice is removed from the frozen product by direct sublimation at low pressure and temperature. Secondary drying is the process step when bounded water is removed from the product matrix utilizing the diffusion of residual water to the evaporation surface. Product temperature during secondary drying is normally higher than during primary drying. See, Tang X. et al. (2004) "Design of freeze-drying processes for pharmaceuticals: Practical advice," *Pharm. Res.*, 21:191-200; Nail S. L. et al. (2002) "Fundamentals of freeze-drying," in Development and manufacture of protein pharmaceuticals. Nail S. L. editor New York: Kluwer Academic/Plenum Publishers, pp 281-353; Wang et al. (2000) "Lyophilization and development of solid protein pharmaceuticals," *Int. J. Pharm.*, 203:1-60; Williams N. A. et al. (1984) "The lyophilization of pharmaceuticals; A literature review." *J. Parenteral Sci. Technol.*, 38:48-59. Generally, any lyophilization process can be used in connection with the present invention.

In some embodiments, an annealing step may be introduced during the initial freezing of the product. The annealing step may reduce the overall cycle time. Without wishing to be bound by any theories, it is contemplated that the annealing step can help promote excipient crystallization and formation of larger ice crystals due to re-crystallization of small crystals formed during supercooling, which, in turn, improves reconstitution. Typically, an annealing step includes an interval or oscillation in the temperature during freezing. For example, the freeze temperature may be −40° C., and the annealing step will increase the temperature to, for example, −10° C. and maintain this temperature for a set period of time. The annealing step time may range from 0.5 hours to 8 hours (e.g., 0.5, 1.0 1.5, 2.0, 2.5, 3, 4, 6, and 8 hours). The annealing temperature may be between the freezing temperature and 0° C.

Lyophilization may be performed in a container, such as a tube, a bag, a bottle, a tray, a vial (e.g., a glass vial), syringe or any other suitable containers. The containers may be disposable. Lyophilization may also be performed in a large scale or small scale. In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial.

Many different freeze-dryers are available for this purpose such as Hull pilot scale dryer (SP Industries, USA), Genesis (SP Industries) laboratory freeze-dryers, or any freeze-dryers capable of controlling the given lyophilization process parameters. Freeze-drying is accomplished by freezing the formulation and subsequently subliming ice from the frozen content at a temperature suitable for primary drying. Initial freezing brings the formulation to a temperature below about −20° C. (e.g., −50° C., −45° C., −40° C., −35° C., −30° C., −25° C., etc.) in typically not more than about 4 hours (e.g., not more than about 3 hours, not more than about 2.5 hours, not more than about 2 hours). Under this condition, the product temperature is typically below the eutectic point or the collapse temperature of the formulation. Typically, the shelf temperature for the primary drying will range from about −30 to 25° C. (provided the product remains below the melting point during primary drying) at a suitable pressure, ranging typically from about 20 to 250 mTorr. The formulation, size and type of the container holding the sample (e.g., glass vial) and the volume of liquid will mainly dictate the time required for drying, which can range from a few hours to several days. A secondary drying stage is carried out at about 0-60° C., depending primarily on the type and size of container and the type of therapeutic agent employed. Again, volume of liquid will mainly dictate the time required for drying, which can range from a few hours to several days.

As a general proposition, lyophilization will result in a lyophilized formulation in which the moisture content thereof is less than about 5%, less than about 4%, less than about 3%, less than about 2%, less than about 1%, and less than about 0.5%.

Reconstitution according to the present invention may be performed in any container. Exemplary containers suitable for the invention include, but are not limited to, such as tubes, vials, syringes (e.g., single-chamber or dual-chamber), bags, bottles, and trays. Suitable containers may be made of any materials such as glass, plastics, metal. The containers may be disposable or reusable. Reconstitution may also be performed in a large scale or small scale.

In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial. In some embodiments, a suitable container for lyophilization and reconstitution is a dual chamber syringe (e.g., Lyo-Ject,® (Vetter) syringes). For example, a dual chamber syringe may contain both the lyophilized substance and the diluent, each in a separate chamber, separated by a stopper. To reconstitute, a plunger can be attached to the stopper at the diluent side and pressed to move diluent into the product chamber so that the diluent can contact the lyophilized substance and reconstitution may take place as described herein.

The pharmaceutical compositions, formulations and related methods of the invention are useful for delivering a variety of therapeutic agents to the CNS of a subject (e.g., intrathecally, intraventricularly or intracisternally) and for the treatment of the associated diseases. The pharmaceutical compositions of the present invention are particularly useful for delivering proteins and enzymes (e.g., enzyme replacement therapy) to subjects suffering from lysosomal storage disorders. The lysosomal storage diseases represent a group of relatively rare inherited metabolic disorders that result from defects in lysosomal function. The lysosomal diseases are characterized by the accumulation of undigested macromolecules within the lysosomes, which results in an increase in the size and number of such lysosomes and ultimately in cellular dysfunction and clinical abnormalities.

Intrathecal Delivery

In some embodiments, intrathecal administration is used to deliver a desired replacement enzyme (e.g., an HNS protein) into the CSF. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al. Advances in Drug Delivery Systems and Applications in Neurosurgery, 143-192 and Omaya et al., Cancer Drug Delivery, 1: 169-179, the contents of which are incorporated herein by reference.

According to the present invention, an enzyme may be injected at any region surrounding the spinal canal. In some embodiments, an enzyme is injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar IT delivery" or "lumbar IT administration." The term "cisterna magna" refers to the space around and below the cerebellum via the opening between the skull and the top of the spine. Typically, intrathecal injection via cisterna magna is also referred to as "cisterna magna delivery." The term "cerebral ventricle" refers to the cavities in the brain that are continuous with the central canal of the spinal cord. Typically, injections via the cerebral ventricle cavities are referred to as intraventricular Cerebral (ICV) delivery.

In some embodiments, "intrathecal administration" or "intrathecal delivery" according to the present invention refers to lumbar IT administration or delivery, for example, delivered between the third and fourth lumbar (lower back) vertebrae and, more inclusively, the L2-S1 region of the spine. It is contemplated that lumbar IT administration or delivery distinguishes over cisterna magna delivery in that lumbar IT administration or delivery according to our invention provides better and more effective delivery to the distal spinal canal, while cisterna magna delivery, among other things, typically does not deliver well to the distal spinal canal.

Device for Intrathecal Delivery

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. A suitable securing mechanism contains one or more nobs mounted on the surface of the hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external.

In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4).

Relative to intravenous administration, a single dose volume suitable for intrathecal administration is typically small. Typically, intrathecal delivery according to the present invention maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before IT administration. In those cases, a suitable single dose volume may be e.g., more than about 3 ml, 4 ml, 5 ml, 6 ml, 7 ml, 8 ml, 9 ml, 10 ml, 15 ml, or 20 ml.

Various other devices may be used to effect intrathecal administration of a therapeutic composition. For example, formulations containing desired enzymes may be given using an Ommaya reservoir which is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir. Other devices for intrathecal administration of therapeutic compositions or formulations to an individual are described in U.S. Pat. No. 6,217,552, incorporated herein by reference. Alternatively, the drug may be intrathecally given, for example, by a single injection, or continuous infusion. It should be understood that the dosage treatment may be in the form of a single dose administration or multiple doses.

For injection, formulations of the invention can be formulated in liquid solutions. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In one embodiment of the invention, the enzyme is administered by lateral cerebro ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger. In some embodiments, injection into the third and fourth smaller ventricles can also be made.

In yet another embodiment, the pharmaceutical compositions used in the present invention are administered by injection into the cisterna magna, or lumbar area of a subject.

In another embodiment of the method of the invention, the pharmaceutically acceptable formulation provides sustained delivery, e.g., "slow release" of the enzyme or other pharmaceutical composition used in the present invention, to a subject for at least one, two, three, four weeks or longer periods of time after the pharmaceutically acceptable formulation is administered to the subject.

As used herein, the term "sustained delivery" refers to continual delivery of a pharmaceutical formulation of the invention in vivo over a period of time following administration, preferably at least several days, a week or several weeks. Sustained delivery of the composition can be demonstrated by, for example, the continued therapeutic effect of the enzyme over time (e.g., sustained delivery of the enzyme can be demonstrated by continued reduced amount of storage granules in the subject). Alternatively, sustained delivery of the enzyme may be demonstrated by detecting the presence of the enzyme in vivo over time.

Kits

The present invention further provides kits or other articles of manufacture which contains the formulation of the present invention and provides instructions for its reconstitution (if lyophilized) and/or use. Kits or other articles of manufacture may include a container, an IDDD, a catheter and any other articles, devices or equipment useful in interthecal administration and associated surgery. Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to total enzyme dose or protein concentrations as described above. The label may further indicate that the formulation is useful or intended for, for example, IT administration. The label may further indicate, as described above, the administration interval, the administration period and/or the appropriate age of an intended recipient. In some embodiments, a container may contain a single dose of a stable formulation containing a therapeutic agent (e.g., a replacement enzyme). In various embodiments, a single dose comprises greater than 10 mg, greater than 45 mg or greater than 90 mg of total replacement enzyme (e.g., heparan N-sulfatase). In other embodiments, a single dose comprises 10 mg, 45 mg or 90 mg of total replacement enzyme (e.g., heparan N-sulfatase).

In various embodiments, a single dose is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the dose may be a multiuse vial, which allows for repeat administrations (e.g., from 2-6 administrations) of one or more dosages. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 25 mg/ml, at least 45 mg/ml, at least 50 mg/ml, at least 75 mg/ml, at least 90 mg/ml, at least 100 mg/ml). Kits or other articles of manufacture may further include other materials desirable from a commercial and user standpoint, including other buffers, diluents, filters, needles, IDDDs, catheters, syringes, and package inserts with instructions for use.

Treatment of Sanfilippo A Syndrome

Inventive methods described herein can advantageously facilitate the delivery of recombinant HNS enzyme to targeted organelles and effectively treat Sanfilippo syndrome Type A. In particular, inventive methods described herein can be used to reduce accumulation of glycosaminoglycans (GAG) in the lysosomes of affected cells and tissues and/or to improve cognitive function.

Sanfilippo syndrome, or mucopolysaccharidosis III (MPS IIIA), is a rare genetic disorder characterized by the deficiency of enzymes involved in the degradation of glycosaminoglycans (GAG). In the absence of enzyme, partially degraded GAG molecules cannot be cleared from the body and accumulate in lysosomes of various tissues, resulting in progressive widespread somatic dysfunction (Neufeld and Muenzer, 2001).

Four distinct forms of MPS III, designated MPS IIIA, B, C, and D, have been identified. Each represents a deficiency in one of four enzymes involved in the degradation of the GAG heparan sulfate. All forms include varying degrees of the same clinical symptoms, including coarse facial features, hepatosplenomegaly, corneal clouding and skeletal deformities. Most notably, however, is the severe and progressive loss of cognitive ability, which is tied not only to the accumulation of heparan sulfate in neurons, but also the subsequent elevation of the gangliosides GM2, GM3 and GD2 caused by primary GAG accumulation (Walkley 1998).

Mucopolysaccharidosis type IIIA (MPS IIIA; Sanfilippo Syndrome Type A) is the most severe form of Sanfilippo syndrome and affects approximately 1 in 100,000 people worldwide. Sanfilippo Syndrome Type A (SanA) is characterized by a deficiency of the enzyme heparan-N-sulfatase (HNS), an exosulfatase involved in the lysosomal catabolism of glycosaminoglycan (GAG) heparan sulfate (Neufeld E F, et al. The Metabolic and Molecular Bases of Inherited Disease (2001) pp. 3421-3452). In the absence of this enzyme, GAG heparan sulfate (HS) accumulates in lysosomes of neurons and glial cells, with lesser accumulation outside the brain. As a result, HS accumulates significantly in the CSF of afflicted individuals. Thus, elevated levels of GAG in CSF indicate a subject in need of treatment, and reduction in HS levels following intrathecal administration of human recombinant HNS serves as a marker of therapeutic efficacy. In some embodiments, the subject in need of treatment has a GAG level in the CSF greater than about 100 pmol/ml (e.g., about 200 pmol/ml, 300 pmol/ml, 400 pmol/ml, 500 pmol/ml, 600 pmol/ml, 700 pmol/ml, 800 pmol/ml, 900 pmol/ml, 1000 pmol/ml, 1500 pmol/ml, 2000 pmol/ml, 2500 pmol/ml, 3000 pmol/ml, or greater) before the treatment. In some embodiments, the subject in need of treatment has a GAG level in the CSF greater than 1000 pmol/ml before the treatment.

In some embodiments the GAG is total heparan sulfate and the total heparan sulfate (e.g., SPTHS) is measured using the Sensi-Pro™ HPLC assay (Zacharon). In some embodiments, the subject in need of treatment has a baseline total heparan sulfate (e.g., SPTHS) level in the CSF greater than about 10,000 pmol/ml (e.g., about 20,000 pmol/ml, about 30,000 pmol/ml, about 40,000 pmol/ml, about 50,000 pmol/ml, about 60,000 pmol/ml, about 70,000 pmol/ml, about 80,000 pmol/ml, about 90,000 pmol/ml, about 100,000 pmol/ml, about 150,000 pmol/ml, about 200,000 pmol/ml, about 250,000 pmol/ml, about 300,000 pmol/ml, or greater) before the treatment. In some embodiments, the subject in need of treatment has a GAG level in the CSF greater than about 100,000 pmol/ml before the treatment.

In some embodiments the GAG is heparan sulfate and the GAG is measured via non-reducing end identification (e.g., SPNREA) using the Sensi-Pro™ HPLC assay (Zacharon). In some embodiments, the subject in need of treatment has a baseline heparan sulfate level, as measured via non-reducing end identification (e.g., SPNREA), in the CSF greater than about 100 pmol/ml (e.g., about 200 pmol/ml, about 300 pmol/ml, about 400 pmol/ml, about 500 pmol/ml, about 600 pmol/ml, about 700 pmol/ml, about 800 pmol/ml, about 900 pmol/ml, about 1000 pmol/ml, about 1500 pmol/ml, about 2000 pmol/ml, about 2500 pmol/ml, about 3000 pmol/ml, or greater) before the treatment. In some embodiments, the subject in need of treatment has a GAG level in the CSF greater than about 1000 pmol/ml before the treatment.

A defining clinical feature of this disorder is central nervous system (CNS) degeneration, which results in loss of, or failure to attain, major developmental milestones. The progressive cognitive decline culminates in dementia and premature mortality. The disease typically manifests itself in young children, and the lifespan of an affected individual generally does not extend beyond late teens to early twenties.

Compositions and methods of the present invention may be used to effectively treat individuals suffering from or susceptible to Sanfilippo Syndrome Type A. The terms, "treat" or "treatment," as used herein, refers to amelioration of one or more symptoms associated with the disease, prevention or delay of the onset or progression of one or more symptoms of the disease, and/or lessening of the severity or frequency of one or more symptoms of the disease.

In some embodiments, treatment refers to partial or complete alleviation, amelioration, relief, inhibition, delaying onset, reducing severity and/or incidence of neurological impairment in a San A patient. As used herein, the term "neurological impairment" includes various symptoms associated with impairment of the central nervous system (e.g., the brain and spinal cord). Symptoms of neurological impairment may include, for example, developmental delay, progressive cognitive impairment, hearing loss, impaired speech development, deficits in motor skills, hyperactivity, aggressiveness and/or sleep disturbances, among others.

In some embodiments, treatment refers to improved or stabilized cognitive functions (i.e. cognitive status or performance) as compared to untreated subjects or pretreatment levels (e.g, baseline levels). In some embodiments, treatment refers to a reduced or lessened decline in cognitive functions (i.e. cognitive status or performance) as compared to untreated subjects or pre-treatment levels. In some embodiments, cognitive functions (i.e. cognitive status or performance) are assessed by standardized tests and expressed as a developmental quotient (DQ). In some embodiments, cognitive functions (i.e. cognitive status or performance) are assessed by one or more scales. Any cognitive scale known to those of skill in the art may be used in embodiments of the invention as appropriate for the age and/or developmental status of the subject (as discussed in greater detail below). Exemplary cognitive scales include, but are not limited to, the Bayley Scales of Infant Development and the Kaufman Assessment Battery for Children. Data obtained from scales used in embodiments of the invention may be used to ascertain the DQ score calculated from mental age equivalent of the child in months divided by the calendar age in months (multiplied by 100 to give percentage points). Additional measurements of cognitive ability that may be used in embodiments of the invention include the Woodcock-Johnson Psycho Educational Battery (WJPEB), which is an individual test of educational achievement in reading, writing, spelling and math. Standard scores are derived that compare the test-taker against US norms and can be expressed as an age or grade-level equivalency. The Scales of Independent Behavior-Revised (SIB-R), a subtest of WJPEB, which measures a subject's adaptive behavior and is expressed as a raw score similar to subjects IQ, may also be used. Some embodiment of the invention may utilize the general conceptual ability (GCA) score, which is an indicator of general cognitive ability. In some embodiments, DAS-II (Differential Ability Scales—Second Edition) IQ test may be used. DAS-II is a comprehensive, individually administered, clinical instrument for assessing the cognitive abilities that are important to learning. In some particular embodiments, the subject has a pre-treatment DQ score, measured by any method, at or greater than 60.

In some embodiments, treatment refers to decreased lysosomal storage (e.g., of GAG) in various tissues. In some embodiments, treatment refers to decreased lysosomal storage in brain target tissues, spinal cord neurons, and/or peripheral target tissues. In certain embodiments, lysosomal storage is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, lysosomal storage is decreased by at least 1-fold, 2-fold, 3-fold, 4-fold, 5-fold, 6-fold, 7-fold, 8-fold, 9-fold or 10-fold as compared to a control. In some embodiments, lysosomal storage is measured by the presence of lysosomal storage granules (e.g., zebra-striped morphology).

In some embodiments, treatment refers to decreased GAG levels in cerebrospinal fluid (CSF). In some embodiments, CSF GAG levels are decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to pretreatment (e.g., baseline) or control levels. In some embodiments, CSF GAG levels are decreased by at least 1-fold, 2-fold, 3-fold, 4-fold, 5-fold, 6-fold, 7-fold, 8-fold, 9-fold or 10-fold as compared to pretreatment (e.g., baseline) or control levels.

In particular embodiments, the intrathecal administration of the recombinant HNS enzyme at a therapeutically effective dose and an administration interval results in the GAG level in the CSF lower than 6000 pmol/ml (e.g., lower than about 5000, 4000, 3000, 2000, 1000 pmol/ml). In some embodiments, CSF GAG levels are decreased to lower than about 1000 pmol/ml (e.g., lower than about 900 pmol/ml, 800 pmol/ml, 700 pmol/ml, 600 pmol/ml, 500 pmol/ml, 400 pmol/ml, 300 pmol/ml, 200 pmol/ml, 100 pmol/ml, 50 pmol/ml, 10 pmol/ml, or less). In particular embodiments, the GAG is heparan sulfate (HS). In some embodiments, GAG levels are measured by methods known to those of skill in the art, including but not limited to, electro-spray ionization-tandem mass spectrometry (with and without liquid chromatography), HPLC or LC-MS based assays as described in Lawrence R. et al. Nat. Chem. Biol.; 8(2):197-204.

In particular embodiments, the intrathecal administration of the recombinant HNS enzyme at a therapeutically effective dose and an administration interval results in a GAG level (e.g., total heparan sulfate (e.g., SPTHS) is measured using the Sensi-Pro™ HPLC assay (Zacharon)), in the CSF lower than 70,000 pmol/ml (e.g., lower than about 60,000 pmol/ml, about 50,000 pmol/ml, about 40,000 pmol/ml, about 30,000 pmol/ml, about 20,000 pmol/ml, or about 10,000 pmol/ml). In some embodiments, CSF GAG levels are decreased to lower than about 5000 pmol/ml (e.g., lower than about 4000 pmol/ml, about 3000 pmol/ml, about 2000 pmol/ml, about 1000 pmol/ml or about 500 pmol/ml, or less).

In particular embodiments, the intrathecal administration of the recombinant HNS enzyme at a therapeutically effective dose and an administration interval results in a GAG level (e.g., GAG measured via non-reducing end identification (e.g., SPNREA) using the Sensi-Pro™ HPLC assay (Zacharon)), in the CSF lower than about 1500 pmol/ml (e.g., lower than about 1250 pmol/ml, about 1000 pmol/ml, about 900 pmol/ml, about 800 pmol/ml, about 700 pmol/ml or about 600 pmol/ml). In some embodiments, CSF GAG levels are decreased to lower than about 500 pmol/ml (e.g., lower than about 400 pmol/ml, about 300 pmol/ml, about 200 pmol/ml, about 100 pmol/ml or about 50 pmol/ml, or less).

In some embodiments, treatment refers to decreased progression of loss of cognitive ability, performance or function. In certain embodiments, progression of loss of cognitive ability, performance or function is decreased by about 1%, 2%, 5%, 10%, 15%, 20%, 25%, 30%, 35%, 40%, 45%, 50%, 55%, 60%, 65%, 70%, 75%, 80%, 85%, 90%, 95%, 100% or more as compared to a control or as compared to pretreatment (e.g., baseline levels). In some embodiments, treatment refers to decreased developmental delay. In certain embodiments, developmental delay is decreased by about 1%, 2%, 5%, 10%, 15%, 20%, 25%, 30%, 35%, 40%, 45%, 50%, 55%, 60%, 65%, 70%, 75%, 80%, 85%, 90%, 95%, 100% or more as compared to a control or as compared to pretreatment (e.g., baseline levels).

In some embodiments, treatment refers to decreased progression of total disability. In certain embodiments, progression of total disability is decreased by about 1%, 2%, 5%, 10%, 15%, 20%, 25%, 30%, 35%, 40%, 45%, 50%, 55%, 60%, 65%, 70%, 75%, 80%, 85%, 90%, 95%, 100% or more as compared to a control or as compared to pretreatment (e.g., baseline levels). In some embodiments, treatment refers to improvement, or reduction, in total disability. In certain embodiments, total disability is improved by about 1%, 2%, 5%, 10%, 15%, 20%, 25%, 30%, 35%, 40%, 45%, 50%, 55%, 60%, 65%, 70%, 75%, 80%, 85%, 90%, 95%, 100% or more as compared to a control or as compared to pretreatment (e.g., baseline levels).

In some embodiments, treatment refers to decreased progression of undesirable behaviors. In certain embodiments, progression of undesirable behaviors is decreased by about 1%, 2%, 5%, 10%, 15%, 20%, 25%, 30%, 35%, 40%, 45%, 50%, 55%, 60%, 65%, 70%, 75%, 80%, 85%, 90%, 95%, 100% or more as compared to a control or as compared to pretreatment (e.g., baseline levels). In some embodiments, treatment refers to improvement, or reduction, in undesirable behaviors. In certain embodiments, undesirable behaviors are improved by about 1%, 2%, 5%, 10%, 15%, 20%, 25%, 30%, 35%, 40%, 45%, 50%, 55%, 60%, 65%, 70%, 75%, 80%, 85%, 90%, 95%, 100% or more as compared to a control or as compared to pretreatment (e.g., baseline levels).

In some embodiments, treatment refers to decreased progression of loss of quality of life. In certain embodiments, progression of loss of quality of life is decreased by about 1%, 2%, 5%, 10%, 15%, 20%, 25%, 30%, 35%, 40%, 45%, 50%, 55%, 60%, 65%, 70%, 75%, 80%, 85%, 90%, 95%, 100% or more as compared to a control or as compared to pretreatment (e.g., baseline levels). In some embodiments, treatment refers to improvement in quality of life. In certain embodiments, quality of life is improved by about 1%, 2%, 5%, 10%, 15%, 20%, 25%, 30%, 35%, 40%, 45%, 50%, 55%, 60%, 65%, 70%, 75%, 80%, 85%, 90%, 95%, 100% or more as compared to a control or as compared to pretreatment (e.g., baseline levels).

In some embodiments, treatment refers to decreased progression of loss of grey matter volume. In certain embodiments, progression of loss of grey matter volume is decreased by about 1%, 2%, 5%, 10%, 15%, 20%, 25%, 30%, 35%, 40%, 45%, 50%, 55%, 60%, 65%, 70%, 75%, 80%, 85%, 90%, 95%, 100% or more as compared to a control or as compared to pretreatment (e.g., baseline levels). In some embodiments, treatment refers no loss in grey matter volume as compared to a control or as compared to pretreatment (e.g., baseline levels).

In some embodiments, treatment refers to decreased progression of loss of white matter volume. In certain embodiments, progression of loss of grey matter volume is decreased by about 1%, 2%, 5%, 10%, 15%, 20%, 25%, 30%, 35%, 40%, 45%, 50%, 55%, 60%, 65%, 70%, 75%, 80%, 85%, 90%, 95%, 100% or more as compared to a control or as compared to pretreatment (e.g., baseline levels). In some embodiments, treatment refers no loss in white matter volume as compared to a control or as compared to pretreatment (e.g., baseline levels).

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with Sanfilippo Syndrome Type A, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having Sanfilippo Syndrome Type A or having the potential to develop Sanfilippo Syndrome Type A. The individual can have residual endogenous HNS expression and/or activity, or no measurable activity. For example, the individual having Sanfilippo Syndrome Type A may have HNS expression levels that are less than about 30-50%, less than about 25-30%, less than about 20-25%, less than about 15-20%, less than about 10-15%, less than about 5-10%, less than about 0.1-5% of normal HNS expression levels.

Compositions and methods of the present invention may be used to effectively treat subjects of a variety of ages. In certain embodiments of the present invention the subject is approximately 3 years to 22 years in age. In certain embodiments of the present invention, the subject is less than about 10 years in age. In certain embodiments of the present invention, the subject is approximately 3 years to 10 years in age. In certain embodiments, the subject approximately 10 years in age. In certain embodiments of the invention, the subject is less than 3 years of age. In certain embodiments of the invention, the subject is approximately 1 year to 3 years of age. In some embodiments, the median age of a subject is about 3 years. In some embodiments, the median age of a subject is about 1 year of age. In some embodiments, the subject is at least 3 years old. In certain embodiments, the subject is younger than 4 years old. In certain embodiments, the subject is approximately 2 years to 11 years in age. In other embodiments, the subject is approximately 12 years to 17 years in age. In yet another embodiment, the subject is approximately 18 years to 64 years in age. In some embodiments, the subject is at least 1 year old; i.e., at least 12 months old. It is contemplated that early treatment is important to maximize the benefits of treatment.

Immune Tolerance

Generally, intrathecal administration of a therapeutic agent (e.g., a replacement enzyme) according to the present invention does not result in severe adverse effects in the subject. As used herein, severe adverse effects induce, but are not limited to, substantial immune response, toxicity, or death. As used herein, the term "substantial immune response" refers to severe or serious immune responses, such as adaptive T-cell immune responses.

Thus, in many embodiments, inventive methods according to the present invention do not involve concurrent immunosuppressant therapy (i.e., any immunosuppressant therapy used as pre-treatment/preconditioning or in parallel to the method). For example, intrathecal administration according to embodiments disclosed herein may not require an immunosuppressant. In some embodiments, inventive methods according to the present invention do not involve an immune tolerance induction in the subject being treated. In some embodiments, inventive methods according to the present invention do not involve a pre-treatment or preconditioning of the subject using T-cell immunosuppressive agent.

In some embodiments, intrathecal administration of therapeutic agents can mount an immune response against these agents. Thus, in some embodiments, it may be useful to render the subject receiving the replacement enzyme tolerant to the enzyme replacement therapy. Immune tolerance may be induced using various methods known in the art. For example, an initial 30-60 day regimen of a T-cell immunosuppressive agent such as cyclosporin A (CsA) and an antiproliferative agent, such as, azathioprine (Aza), combined with weekly intrathecal infusions of low doses of a desired replacement enzyme may be used.

Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor ($\alpha$-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

Administration

Inventive methods of the present invention contemplate single as well as multiple administrations of a therapeutically effective amount of the therapeutic agents (e.g., replacement enzymes) described herein. Therapeutic agents (e.g., replacement enzymes) can be administered at regular intervals, depending on the nature, severity and extent of the subject's condition (e.g., a lysosomal storage disease). In some embodiments, a therapeutically effective amount of the therapeutic agents (e.g., replacement enzymes) of the present invention may be administered intrathecally periodically at regular intervals (e.g., once every year, once every six months, once every five months, once every four months, once every three months, bimonthly (once every two months), monthly (once every month), once every four weeks, once every three weeks, biweekly (once every two weeks), or weekly (once every week)). In one embodiment, monthly administration is once every 28 days +/−7 days. In one embodiment, a biweekly dose is once every 14 days +/−2 days.

In some embodiments, the therapeutic agent(s) can be administered as a total monthly dose. For example, a subject may receive a total monthly dose of 90 mg by biweekly administration of a 45 mg dose. More specifically, the 45 mg dose may be administered every 14 days +/−2 days.

In some embodiments, intrathecal administration may be used in conjunction with other routes of administration (e.g., intravenous, subcutaneously, intramuscularly, parenterally, transdermally, or transmucosally (e.g., orally or nasally)). In some embodiments, those other routes of administration (e.g., intravenous administration) may be performed no more frequent than biweekly, monthly, once every two months, once every three months, once every four months, once every five months, once every six months, annually administration.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

In some embodiments, the therapeutically effective dose is defined by total enzyme administered per dose. In some embodiments, the therapeutically effective total enzyme dose ranges from about 10 mg to about 100 mg, e.g., from about 10 mg to about 90 mg, from about 10 mg to about 80 mg, from about 10 mg to about 50 mg, from about 10 mg to about 40 mg, from about 10 mg to about 30 mg, and from about 10 mg to about 20 mg. In some embodiments, the total enzyme dose is from about 40 mg to about 50 mg. In some embodiments, the therapeutically effective dose is or greater than about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg per dose. In some embodiments, the therapeutically effective dose is or greater than about 10 mg per dose. In some embodiments, the therapeutically effective dose is or greater than about 45 mg per dose. In some embodiments, the therapeutically effective dose is or greater than about 90 mg per dose.

In some embodiments, the therapeutically effective dose ranges from about 0.005 mg/kg brain weight to 500 mg/kg brain weight, e.g., from about 0.005 mg/kg brain weight to 400 mg/kg brain weight, from about 0.005 mg/kg brain weight to 300 mg/kg brain weight, from about 0.005 mg/kg brain weight to 200 mg/kg brain weight, from about 0.005 mg/kg brain weight to 100 mg/kg brain weight, from about 0.005 mg/kg brain weight to 90 mg/kg brain weight, from about 0.005 mg/kg brain weight to 80 mg/kg brain weight, from about 0.005 mg/kg brain weight to 70 mg/kg brain weight, from about 0.005 mg/kg brain weight to 60 mg/kg brain weight, from about 0.005 mg/kg brain weight to 50 mg/kg brain weight, from about 0.005 mg/kg brain weight to 40 mg/kg brain weight, from about 0.005 mg/kg brain weight to 30 mg/kg brain weight, from about 0.005 mg/kg brain weight to 25 mg/kg brain weight, from about 0.005 mg/kg brain weight to 20 mg/kg brain weight, from about 0.005 mg/kg brain weight to 15 mg/kg brain weight, from about 0.005 mg/kg brain weight to 10 mg/kg brain weight.

In some embodiments, the therapeutically effective dose is or greater than about 5 mg/kg brain weight, about 10 mg/kg brain weight, about 15 mg/kg brain weight, about 20 mg/kg brain weight, about 25 mg/kg brain weight, about 30 mg/kg brain weight, about 35 mg/kg brain weight, about 40 mg/kg brain weight, about 45 mg/kg brain weight, about 50 mg/kg brain weight, about 55 mg/kg brain weight, about 60 mg/kg brain weight, about 65 mg/kg brain weight, about 70 mg/kg brain weight, about 75 mg/kg brain weight, about 80 mg/kg brain weight, about 85 mg/kg brain weight, about 90 mg/kg brain weight, about 95 mg/kg brain weight, about 100 mg/kg brain weight, about 200 mg/kg brain weight, about 300 mg/kg brain weight, about 400 mg/kg brain weight, or about 500 mg/kg brain weight.

In some embodiments, the therapeutically effective dose may also be defined by mg/kg body weight. As one skilled in the art would appreciate, the brain weights and body weights can be correlated. Dekaban A S. "Changes in brain weights during the span of human life: relation of brain weights to body heights and body weights," Ann Neurol 1978; 4:345-56. Thus, in some embodiments, the dosages can be converted as shown in Table 3.

TABLE 3

Change in Brain Wight During Early Human Development

| Age Group | Age (yr) | No. of Brains | Brain Weight (kg) | | | | Body Height (m) | | | | Body Weight (kg) | | | |
|---|---|---|---|---|---|---|---|---|---|---|---|---|---|---|
| | | | Mean | SD | SEM | % Change | Mean | SD | SEM | % Change | Mean | SD | SEM | % Change |
| 1 | NB (0-10 d) | 241 | 0.38 | 0.09 | 0.00 | ... | 0.5 | 0.05 | 0.00 | ... | 2.95 | 0.47 | 0.03 | ... |
| 2 | 0.5 (4-8 mo) | 87 | 0.64 | 0.16 | 0.01 | 66.8 | 0.59 | 0.09 | 0.01 | 18.6 | 5.88 | 3.06 | 0.32 | 99.4 |
| 3 | 1 (9-18 mo) | 33 | 0.97 | 0.16 | 0.02 | 50.6 | 0.76 | 0.11 | 0.02 | 28.5 | 9.47 | 2.37 | 0.41 | 61.2 |
| 4 | 2 (19-30 mo) | 53 | 1.12 | 0.20 | 0.02 | 16.2 | 0.85 | 0.12 | 0.01 | 11.7 | 13.20 | 3.57 | 0.49 | 39.3 |
| 5 | 3 (31-43 mo) | 19 | 1.27 | 0.21 | 0.04 | 12.8 | 0.94 | 0.09 | 0.02 | 11 | 15.55 | 3.43 | 0.78 | 17.9 |
| 6 | 4-5 | 29 | 1.30 | 0.02 | 0.00 | 2.3 | 1.06 | 0.03 | 0.00 | 12.8 | 19.46 | 1.21 | 0.22 | 25.1 |

In some embodiments, the therapeutically effective dose may also be defined by mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14; 5:10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

In accordance with embodiments described herein, the present invention provides, in part, therapeutically effective and appropriately timed dosing regimens (i.e., administration schedules) for enzyme replacement therapies to treat lysosomal storage diseases with maximum efficacy. For example, a replacement enzyme (e.g., heparan N-sulfatase (HNS)) for a lysosomal storage disease (e.g., Sanfilippo A Syndrome) can be directly introduced into the cerebrospinal fluid (CSF) of a subject in need of treatment at a total enzyme dose (e.g., about 10-100 mg per dose) such that the enzyme effectively and extensively reduces GAG levels in CSF. Stated another way, embodiments of the present invention are based on the discovery, disclosed for the first time herein, that a therapeutically effective dose is optimally determined by total enzyme content rather than by concentration or mg/kg brain weight. Although these measurements may be utilized in some embodiments, the present inventors have discovered that total enzyme per dose is one of the most important determinants of therapeutic efficacy.

In some embodiments, the intrathecal administration is used in conjunction with intravenous administration. In some embodiments, the intravenous administration is no more frequent than once every week. In some embodiments, the intravenous administration is no more frequent than once every two weeks. In some embodiments, the intravenous administration is no more frequent than once every month. In some embodiments, the intravenous administration is no more frequent than once every two months. In certain embodiments, the intravenous administration is more frequent than monthly administration, such as twice weekly, weekly, every other week, or twice monthly.

In some embodiments, the treatment regimen is continued until results indicative of therapeutic efficacy (e.g., reduction in CSF HNS levels) are observed. The present inventors have discovered the period over which the therapeutically effective dosages and accompanying administration levels described herein should be continued in order to observe optimal effect on CSF and urine GAG levels. For example, treatment may be administered at a therapeutically effective dose and at an administration interval for a period sufficient to decrease glycosaminoglycan (GAG) heparan sulfate level in the cerebrospinal fluid (CSF). In some embodiments, the period is at least 1, 2, 3, 4, 5, 6, 7, 8, 9, 10, 11, 12, 18, 24, 30, 36, 48, 54 months or more. In some embodiments, therapeutically effective doses (e.g., total enzyme dose) may be administered according to any one of the above intervals for at least six weeks; e.g., at least ten weeks, at least fourteen weeks, at least twenty weeks, at least twenty-four weeks, at least thirty weeks or more (e.g., indefinitely). In some embodiments, a recombinant heparan N-sulfatase (HNS) enzyme is administered at a therapeutically effective dose and an administration interval for a period sufficient to improve, stabilize or reduce declining of one or more cognitive functions relative to a control.

It is contemplated that starting treatment before the onset of significant cognitive decline is important for measurable improvements, stabilizations or reduced declines in cognitive functions relative to baseline (e.g, prior to treatment). For example, in patients with MPS IIIA, intrathecal enzyme replacement therapy may have to be initiated before one or more cognitive parameters have declined by more than 50%.

In some embodiments, a treatment regimen of enzyme replacement therapy (e.g., HNS) is initiated before cognitive status has substantially declined. For example, treatment may be particularly beneficial if initiated before cognitive status has declined by no more than 60% relative to baseline or control levels, e.g. by no more than 50%, by no more than 40%, by no more than 30%, by no more than 20% or by no more than 10%. Cognitive status may be qualitatively or quantitatively assessed by the tests disclosed herein. For example, in a particular embodiment, treatment is most effective if administered before a subject's developmental quotient (DQ) has declined by about 50% relative to baseline levels. In particular embodiments, treatment is particularly effective if begun before a subject's DQ score has declined to less than about 30; e.g., the subject's DQ score is about 30 or higher, about 40 or higher, about 50 or higher, about 60 or higher, about 70 or higher, etc.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention. Thus, some embodiments of the invention further comprise a step of adjusting the dose and/or administration interval for intrathecal administration based on the GAG level in the CSF. For example, the therapeutic effective dose for intrathecal administration may be adjusted if the GAG level in the CSF fails to decrease relative to the control after 4 doses.

In some embodiments, optimal ages at which intrathecal administration of human recombinant sulfatases (e.g., HNS) should be initiated to maintain cognitive status, stabilize cognitive decline or improve cognitive performance is or younger than 5, 4, 3, 2, 1 years old.

Cognitive Performance

Among other things, the present invention may be used to effectively treat various cognitive and physical impairments associated with, or resulting from, Sanfilippo Type A. In some embodiments, treatment according to the present invention results in improved cognitive performance of a patient suffering from Sanfilippo Type A. As used herein, cognitive performance includes, but is not limited to, cognitive, adaptive, motor, and/or executive functions. Thus, in some embodiments, a treatment marker may be used to monitor improvement, stabilization, reduction or enhancement of one or more cognitive, adaptive, motor, and/or executive functions relative to a control or relative to baseline (e.g., prior to treatment with recombinant HNS).

Assessment of Cognitive Performance

Typically, cognitive performance may be assessed using a cognitive performance test, such as a cognitive performance instrument. As used herein, the term "cognitive performance instrument" includes a cognitive performance test that can be used to evaluate, classify and/or quantify one or more cognitive, adaptive motor and/or executive functions in a subject. As will be understood by those skilled in the art, such a test may be questionnaire or survey filled out by a patient, caregiver, parent, teacher, therapist or psychologist.

Exemplary cognitive performance instruments suitable for assessing cognitive, adaptive motor and/or executive functions are described below.

Differential Abilities Scale (DAS-II)

In some specific embodiments, the cognitive performance instrument is the Differential Ability Scale. The Differential Ability Scale, as the name implies, was developed specifically to be suitable for patients with various types of impairment. The DAS-II is a cognitive test that is designed primarily as a profile test which yields scores for a wide range of abilities, measured either by subtests or composites. However, it has been used as a general test of cognitive ability, including in severely affected populations. The DAS-II comprises 2 overlapping batteries. The Early Years battery is designed for children ages 2 years 6 months through 6 years 11 months. The School-Age Battery is designed for children ages 7 years 0 months through 17 years 11 months. A key feature of these batteries is that they were fully co-normed for ages 5 years 0 months through 8 years 11 months. In consequence, children ages 7 years 0 months through 8 years 11 months can be given the Early Years battery if that is considered more developmentally appropriate for an individual than the School-Age Battery. Similarly, more able children ages 5 years 0 months through 6 years 11 months can be given the School-Age Battery. As a result, the test accommodates all 5 to 8 year old children (i.e., 5 years 0 months through 8 years 11 months) at the extremes of the ability range.

The DAS-II has been validated and normed in the US population and in the British population (as the BAS, or British Abilities Scales). A Spanish version, intended for use in Spain and Spanish-speaking Latin America, is expected to become available in the fall of 2012. The DAS-II incorporates "tailored testing" to enable examiners to select the most appropriate items for a child. This has two major advantages. First, it enables the measure to be both accurate and very time-efficient, which is a major advantage for the examiner. Second, it makes testing shorter and less tiring for the child and often enables the child to discontinue a subtest before having experienced a string of consecutive failures— an advantage for the child, as the tests are more enjoyable and motivating. Without being a limiting example, Table 4 discloses a plurality of subtest capable of measuring different cognitive abilities, for a subject undergoing enzyme replacement therapy.

TABLE 4

List of Cognitive Performance Instruments

| Subtest | Abbreviation | Abilities Measured |
|---|---|---|
| Copying | Copy | Visual-perceptual matching and fine-motor coordination in copying line drawings |
| Early number concepts | ENC | Knowledge of pre-numerical and numerical concepts |
| Matching letter-like forms | MLLF | Visual discrimination among similar shapes |
| Matrices | Mat | Nonverbal reasoning: perception and application of relationships among abstract figures |
| Naming vocabulary | NVoc | Expressive language; knowledge of names |
| Pattern construction | PCon | Visual-perceptual matching, especially of spatial orientation, in copying block patterns. Nonverbal reasoning and spatial visualization in reproducing designs with colored blocks |
| Pattern Construction (alt) | PCon(A) | The same abilities for Pattern construction without a time constraint |
| Phonological processing | PhP | Knowledge of sound structure of the English language and the ability to manipulate sound |
| Picture similarities | PSim | Nonverbal reasoning shown by matching pictures that have a common element or concept |
| Rapid naming | RNam | Automaticity of integration of visual symbols with phonologically referenced naming |
| Recall of designs | RDes | Short-term recall of visual and spatial relationships through reproduction of abstract figures |
| Recall of digits forward | DigF | Short-term auditory memory and oral recall of sequences of numbers |
| Recall of digits backward | DigB | Short-term auditory memory and oral recall of sequences of numbers |
| Recall of objects - Immediate | RObI | Short-term recall of verbal and pictorial information |
| Recall of objects - Delayed | RObD | Intermediate-term recall of verbal and pictorial information |
| Recall of sequential order | SeqO | Short-term recall of verbal and pictorial information |
| Recognition of pictures | RPic | Short-term, nonverbal visual memory measure through recognition of familiar objects |
| Sequential and quantitative reasoning | SQR | Detection of sequential patterns in figures or numbers |
| Speed of information processing | SIP | Quickness in performing simple mental operations |
| Verbal comprehension | VCom | Receptive language: understanding of oral instructions involving basic language concepts |
| Verbal similarities | VSim | Verbal reasoning and verbal knowledge |
| Word definitions | WDef | Knowledge of word meanings as demonstrated through spoken language |

Scales of Independent Behavior-Revised (SIB-R)

In some specific embodiments, the cognitive performance instrument is the scales of independent behavior-revised. The Scales of Independent Behavior-Revised (SIB-R) is a measure of adaptive behavior comprising 14 subscales organized into 4 adaptive behavior clusters: (1) Motor skills, (2) Social Interaction/Communication, (3) Personal Living skills and (4) Community and Living skills. For each item, the rater is presented with statements that ask them to evaluate the ability and frequency with which the individual being rated can or does perform, in its entirety, a particular task without help or supervision. The individual's performance is rated on a 4-point Likert scale, with responses including (0): Never or Rarely—even if asked; (1) Does, but not Well—or about one quarter of the time-may need to be asked; (2) does fairly well—or about three quarters of the time—may need to be asked; (3) does very well—always or almost always without being asked.

It also measures 8 areas of problem behavior. The SIB-R provides norms from infancy through to the age of 80 and above. It has been used in children with autism and intellectual disability. Some experts consider that one of the strengths of the SIB-R is that has application for basic adaptive skills and problem behaviors of children with significant cognitive or autistic spectrum disorders and can map to American Association of Mental Retardation levels of support. The SIB-R is considered to be much less vulnerable to exaggeration than some other measures of adaptive behaviors.

Bayley Scales of Infant Development

In some embodiments, the evaluation of developmental function may be performed using one or more developmental performance instruments. In some embodiments, the developmental performance instrument is the Bayley Scales of Infant Development (BSID-III). The Bayley Scales of Infant Development is a standard series of measurements used primarily to assess the motor (fine and gross), language (receptive and expressive), and cognitive development of infants and toddlers, ages 0-3. This measure consists of a series of developmental play tasks and takes between 45-60 minutes to administer. Raw scores of successfully completed items are converted to scale scores and to composite scores. These scores are used to determine the child's performance compared with norms taken from typically developing children of their age (in months). The assessment is often used in conjunction with the Social-Emotional Adaptive Behavior Questionnaire. Completed by the parent or caregiver, this questionnaire establishes the range of adaptive behaviors that the child can currently achieve and enables comparison with age norms.

In some embodiments, the developmental quotient (DQ) is determined by the Bayley Scales of Infant Development Third Edition (BSID-III). The DQ was calculated from BSID-III mental age equivalent of the child in months divided by the calendar age in months (multiplied by 100 to give percentage points). In some embodiments, the assessment of DQ by BSID-III is performed at baseline (e.g., before treatment with recombinant HNS) and the results compared to the assessment of DQ by BSID-III following treatment with recombinant HNS.

Kaufman Assessment Battery for Children Second Edition (KABC-II)

In some embodiments, the Kaufman Assessment Battery for Children Second Edition (KABC-II) may be performed. KABC-II measures the processing and reasoning ability of children and adolescents between the ages of three and 18 years and is an alternative to BSID-III. In some embodiments, the developmental quotient (DQ) is determined by the KABC-II. The DQ was calculated from KABC-II mental age equivalent of the child in months divided by the calendar age in months (multiplied by 100 to give percentage points). In some embodiments, the assessment of DQ by KABC-II is performed at baseline (e.g., before treatment with recombinant HNS) and the results compared to the assessment of DQ by KABC-II following treatment with recombinant HNS.

Wechsler Intelligence Scale for Children (WISC)

In some embodiments, the Wechsler Intelligence Scale for Children (WISC) may be performed. Typically, the WISC test is an individually administered intelligence test for children, in particular, children between the ages of 6 and 16 inclusive. In some embodiments, the WISC test can be completed without reading or writing. A WISC score generally represents a child's general cognitive ability.

Vineland Adaptive Behavior Scales

In some embodiments, a Vineland Adaptive Behavior Scales assessment is performed. Typically, Vineland Adaptive Behavior Scales measure a person's adaptive level of functioning. The adaptive behaviors include the ability to cope with environmental changes, to learn new everyday skills and to demonstrate independence. Typically, the content and scales of Vineland Adaptive Behavior Scales are organized within a three domain structure: Communication, Daily Living, and Socialization. This structure corresponds to the three broad Domains of adaptive functioning recognized by the American Association of Mental Retardation (AAMR, 2002): Conceptual, Practical, and Social. In addition, Vineland Adaptive Behavior Scales offer a Motor Skills Domain and an optional Maladaptive Behavior Index to provide more in-depth information.

The Vineland Adaptive Behavior Scales Second Edition (VABS-II) test measures five key domains: communication, daily living skills, socialization, motor skills, and the adaptive behavior composite (a composite of the other four domains). An overall developmental quotient (DQ) can be calculated from the mean age-equivalent score obtained by averaging the age equivalent scores for all the sub-domains except for gross and fine motor skills.

In some embodiments, the developmental quotient (DQ) is determined by the Vineland Adaptive Behavior Scales Second Edition (VABS-II). In some embodiments, the assessment of DQ by VABS-II is performed at baseline (e.g., before treatment with recombinant HNS) and the results compared to the assessment of DQ by VABS-II following treatment with recombinant HNS.

Disability Score

Among other things, the present invention may be used to effectively treat various physical impairments associated with, or resulting from, Sanfilippo Type A. In some embodiments, treatment according to the present invention results in an improved disability score of a patient suffering from Sanfilippo Type A. As used herein, a disability score includes, but is not limited to, motor function, expressive/speech language and cognitive function. Thus, in some embodiments, a treatment marker may be used to monitor improvement, stabilization, reduction or enhancement of one or more motor functions, expressive/speech language and cognitive functions relative to a control, or relative to baseline (e.g., prior to treatment with recombinant HNS).

Assessment of Disability Score

Typically, disability score may be assessed using a disability score test, such as a disability score instrument. As used herein, the term "disability score instrument" includes a disability score test that can be used to evaluate, classify and/or quantify one or more disabilities in a subject. As will be understood by those skilled in the art, such a test may be questionnaire or survey filled out by a patient, caregiver, parent, teacher, therapist or psychologist. Exemplary disability score instruments suitable for assessing disability are described below.

Four Point Scoring System/Total Disability Score (FPSS/TDS)

In some specific embodiments, the disability score instrument is the Four Point Scoring System/Total Disability Score (FPSS/TDS) which is specific to Sanfilippo disabilities. The assessment is by parental questionnaire. Total disability score (TDS) is the average of the motor skills, speech abilities and cognitive function scores. In some embodiments, a lower score indicates developmental regression. In some embodiments, the assessment of disability by FPSS/TDS is performed at baseline (e.g., before treatment with recombinant HNS) and the results compared to the assessment of disability by FPSS/TDS following treatment with recombinant HNS.

Behavior

Among other things, the present invention may be used to effectively treat various behavioral impairments associated with, or resulting from, Sanfilippo Type A. In some embodiments, treatment according to the present invention results in improved behavioral performance of a patient suffering from Sanfilippo Type A. As used herein, behavioral performance includes, but is not limited to, comprehensive and expressive language skills, tantrums, mood, and emotion. Thus, in some embodiments, a treatment marker may be used to monitor improvement, stabilization, reduction or enhancement of one or more behaviors relative to a control, or relative to baseline (e.g., prior to treatment with recombinant HNS).

Assessment of Behavior

Typically, behavioral performance may be assessed using a behavioral performance test, such as a behavioral performance instrument. As used herein, the term "behavioral performance instrument" includes a behavioral performance test that can be used to evaluate, classify and/or quantify one or more behaviors in a subject. As will be understood by those skilled in the art, such a test may be a questionnaire or survey filled out by a patient, caregiver, parent, teacher, therapist or psychologist. Exemplary behavioral performance instruments suitable for assessing behavior are described below.

Sanfilippo Behavior Rating Scale (SBRS)

In some specific embodiments, the behavioral performance instrument is the Sanfilippo Behavior Rating Scale (SBRS) which is specific to behaviors characteristic of Sanfilippo Type A. The behaviors assessed include: current communication, past communication, body movements, interaction with objects, activity and routines, emotional function, safety-consciousness, social interaction, eye contact, comfort seeking, self-control/compliance, mood, anger/aggression and self-gratification. In some embodiments, a higher summary score indicates undesirable behavior. In some embodiments, the assessment of behaviors by SBRS is performed at baseline (e.g., before treatment with recombinant HNS) and the results compared to the assessment of behaviors by SBRS following treatment with recombinant HNS.

Quality of Life

Among other things, the present invention may be used to effectively treat the quality of life status associated with, or resulting from, Sanfilippo Type A. In some embodiments, treatment according to the present invention results in improved quality of life status of a patient suffering from Sanfilippo Type A. As used herein, quality of life status includes, but is not limited to, physical, emotional, and social functions. Thus, in some embodiments, a treatment marker may be used to monitor improvement, stabilization, reduction or enhancement of one or more physical, emotional, and social functions relative to a control, or relative to baseline (e.g., prior to treatment with recombinant HNS).

Assessment of Quality of Life

Typically, quality of life status may be assessed using a quality of life test, such as a quality of life instrument. As used herein, the term "quality of life instrument" includes a quality of life test that can be used to evaluate, classify and/or quantify one or more physical, emotional, and social functions in a subject. As will be understood by those skilled in the art, such a test may be a questionnaire or survey filled out by a patient, caregiver, parent, teacher, therapist or psychologist. Exemplary quality of life status instruments suitable for assessing quality of life are described below.

Child Health Questionnaire™ Parent Form 50 (CHQ 50)

In some specific embodiments, the quality of life status instrument is the Child Health Questionnaire™ Parent Form 50 (CHQ 50). CHQ-PF50 was designed to measure the physical and psychosocial well-being of children 5 years to 18 years of age, and consists of 13 health concepts including 11 multi-item and 2 single item scales: physical function, role/social-emotional/behavioral, role/social-physical, bodily pain, general behavior, mental health, self-esteem, general health perceptions, change in health, parental impact-emotional, parental impact-time, family activities, and family cohesion. Transformed scores for all subscales range from 0 to 100. In some embodiments a higher score indicates better health. In some embodiments, the assessment of quality of life by CHQ-PF50 is performed at baseline (e.g., before treatment with recombinant HNS) and the results compared to the assessment of quality of life by CHQ-PF50 following treatment with recombinant HNS.

Infant Toddler Quality of Life Questionnaire™ (ITQOL)

In some specific embodiments, the quality of life status instrument is the Infant Toddler Quality of Life Questionnaire™ (ITQOL). ITQOL was developed for children at least 2 months of age, up to 5 years of age, and assesses the physical, mental, and social well-being of the child and assesses the quality of the parent/guardian's life. The instrument measures overall health, physical abilities, growth and development, bodily pain, temperament and moods, general behavior, global behavior, getting along, general health perceptions, PI-emotion, PI-time and family cohesion. In some embodiments, the assessment of quality of life by ITQOL is performed at baseline (e.g., before treatment with recombinant HNS) and the results compared to the assessment of quality of life by ITQOL following treatment with recombinant HNS.

Children's Sleep Habits Rating Scale

In some specific embodiments, the quality of life status instrument is the Children's Sleep Habits Rating Scale. The Children's Sleep Habits Rating Scale consisting of 35 items that yield a Total Sleep Disturbance score (TSDS), as well as eight subscale scores (bedtime resistance, sleep duration, parasomnias, sleep disordered breathing, night waking, daytime sleepiness, sleep anxiety, and sleep onset delay). The questionnaire is designed for children aged 4 through 12 years. In some embodiments, the assessment of quality of life by Children's Sleep Habits Rating Scale is performed at baseline (e.g., before treatment with recombinant HNS) and the results compared to the assessment of quality of life by Children's Sleep Habits Rating Scale following treatment with recombinant HNS.

Biomarkers

Alternatively, biomarkers of Sanfilippo Type A may also be used. Suitable biomarkers for the present invention may include any substances (e.g., proteins or nucleic acids) that can be used as an indicator of a disease state of Sanfilippo Type A, the severity of the syndrome, or responses to a therapeutic intervention. Typically, a suitable biomarker has a characteristic that can be objectively measured and evaluated as an indicator. Typically, a suitable biomarker for Sanfilippo Type A syndrome is differentially expressed between Sanfilippo Type A syndrome patients and normal healthy individuals. Such biomarkers may be used alone or in combination as an indicator to evaluate risk for Sanfilippo Type A, detect the presence of Sanfilippo Type A, monitor progression or abatement of Sanfilippo Type A, and/or monitor treatment response or optimization. In some embodiments, individual biomarkers described herein may be used. In some embodiments, at least two, three, four, five, six, seven, eight, nine, ten, eleven, twelve, thirteen, fourteen, fifteen, sixteen, seventeen, eighteen, or nineteen biomarkers may be used in combination as a panel. Thus, in some embodiments, one or more biomarkers described herein (e.g., those provided in Table 5), may be used in conjunction with additional markers, such as, for example, glycosaminoglycan (GAG) heparan sulfate (HS), beta-hexosaminidase, LAMP1, LAMP2, to name but a few. Additional exemplary molecular treatment markers suitable for using in diagnosing, evaluating severity, monitoring treatment or adjusting ERT treatment of Sanfilippo Type A are described in International Application PCT/US12/63935, entitled "BIOMARKERS FOR SANFILIPPO SYNDROME AND USES THEREOF," the contents of which are hereby incorporated by reference.

TABLE 5

Exemplary Treatment Markers for Sanfilippo Type A

| Biomarker | Abbreviation | Linear Analysis | Quadratic Analysis | Nearest-Neighbor |
|---|---|---|---|---|
| Alpha-1-Antitrypsin | AAT | — | — | 0.0750 |
| Alpha-2-Macroglobulin | Alpha-2-M | 0.0667 | 0.0000 | 0.0500 |
| Apolipoprotein B | Apo B | — | — | 0.1000 |
| Calbindin | | 0.1000 | 0.0333 | 0.0500 |
| Complement C3 | C3 | — | 0.0583 | 0.0583 |
| Fatty Acid-Binding Protein, heart | H-FABP | — | 0.0583 | 0.0333 |
| Heparin-Binding EGF-Like Growth Factor | HB-EGF | 0.1000 | | |
| Hepatocyte Growth Factor | HGF | — | 0.0417 | 0.0167 |
| Kallikrein-7 | KLK-7 | — | 0.0500 | 0.1000 |
| Lysosomal-Associated Membrane Protein 2 | LAMP2 | 0.1000 | 0.1000 | 0.0750 |
| Macrophage Colony-Stimulating Factor 1 | M-CSF | — | 0.1000 | 0.0667 |
| Monocyte Chemotactic Protein 1 | MCP-1 | — | 0.0750 | 0.0500 |
| Sex Hormone-Binding Globulin | SHBG | 0.0667 | 0.0250 | 0.0000 |
| Tau | | — | 0.0333 | 0.0667 |
| Thyroxine-Binding Globulin | TBG | — | 0.0917 | 0.0667 |
| Tumor Necrosis Factor Receptor-Like 2 | TNFR2 | 0.0500 | 0.0833 | 0.0333 |
| Vascular Endothelial Growth Factor Receptor 1 | VEGFR-1 | | 0.0750 | 0.0583 |
| Vitronectin | | — | — | 0.0500 |
| pTau(181) | | | 0.0917 | 0.0667 |

Neuroanatomical Markers

In some embodiments, a suitable biomarker is associated with neuroanatomical structures and/or their function and is thus classified as a neuroanatomical marker. In some embodiments, neuroanatomical markers include, but are not limited to, total brain volume, total brain size, brain tissue composition, grey matter volume, white matter volume, cortical volume, cortical thickness, ventricular and CSF volume, cerebella volume, basal ganglia size, basal ganglia volume, frontal lobe volume, parietal lobe volume, occipital lobe volume, and/or temporal lobe volume. In some embodiments, neuroanatomical markers include, but are not limited to, electrical impulse, synaptic firing, neuro-kinetics and/or cerebral blood flow. One skilled in the art will appreciate that a large number of analytical tests may be used to assay any of the structural or functional biomarkers described above. For example, in some embodiments, neuroanatomical biomarkers may be assayed using X-rays, Positron Emission Tomography (PET), PIB-PET, F18 PET, Single Photon Emission Computed Tomography (SPECT), Magnetic Resonance Imaging (MRI), Functional Magnetic Resonance Imaging (fMRI), Difusion-tensor MRI (DTMRI), Diffusion-weighted MRI (DWMRI), Perfusion-weighted MRI (PWMRI), Diffusion-Perfusion-weighted MRI (DPW-MRI), Magnetic Resonance Spectroscopy (MRS), electroencephalography (EEG), magnetoencephalography (MEG), Transcranial magnetic stimulation (TMS), Deep brain stimulation (DBS), Laser Doppler Ultrasound, Optical tomographic imaging, Computer Assisted Tomography (CT) and/or Structural MRI (sMRI). The assay methods described above may be used with or without a contrast reagent, such as a fluorescent or radio labeled compound, antibody, oligonucleotide, protein or metabolite.

In some embodiments, MRI is used to measure grey matter volume, white matter volume and/or intracranial CSF volume. In some embodiments, the MRI measurements are made at baseline (e.g., prior to treatment with recombinant HNS). In some embodiments, grey matter volume is measured at baseline and the results compared to grey matter volume following treatment with recombinant HNS. In some embodiments, white matter volume is measured at baseline and the results compared to white matter volume following treatment with recombinant HNS. In some embodiments, intracranial CSF volume is measured at baseline and the results compared to intracranial CSF volume following treatment with recombinant HNS.

Auditory Brainstem Response

Among other things, the present invention may be used to effectively treat auditory brainstem response (ABR) associated with, or resulting from, Sanfilippo Type A. In some embodiments, treatment according to the present invention results in improved ABR of a patient suffering from Sanfilippo Type A. As used herein, ABR includes, but is not limited to, ABR latencies, ABR amplitude, ABR amplitude ratio, ABR log transformed latencies, ABR log transformed amplitude, ABR square-root transformed latencies, ABR square root transformed amplitude. Thus, in some embodiments, a treatment marker may be used to monitor improvement, stabilization, reduction or enhancement of one or more ABR parameters relative to a control, or relative to baseline (e.g., prior to treatment with recombinant HNS). Typically, ABR may be assessed under anesthesia and measured as the electrical response evoked by acoustic stimuli as sound is processed along the auditory pathway.

EXAMPLES

Example 1: Clinical Trial of MPS IIIA Patients to Assess Efficacy

As discussed above, mucopolysaccharidosis III (MPS-III), also known as Sanfilippo Syndrome Type A, is a rare autosomal recessive lysosomal storage disease, caused by a deficiency in one of the enzymes needed to break down the glycosaminoglycan, heparan sulfate (HS). Heparan sulfate is an important cell surface glycoprotein and a critical component in forming and maintaining the extra-cellular matrix. Four different types of MPS-III (Sanfilippo Syndrome) have been identified: MPS-III A, B, C and D (i.e., Sanfilippo syndrome A, B, C and D). While each of the four MPS-III types display substantially similar clinical symptoms, they are each distinguished by a different enzyme deficiency. MPS-III A (Sanfilippo Syndrome A) has been shown to occur as a result of 70 different possible mutations in the heparan N-sulfatase gene, which reduce enzyme function. As a result, each of the enzyme defects causes accumulation of heparan sulfate in Sanfilippo Syndrome patients.

Although the pathological cascade for the disease is poorly understood, it has been shown that primary accumulation of heparan sulfate triggers secondary accumulation of toxic metabolites, neuroinflammation, disrupts growth factor signaling and leads to dysregulated cell death. Clinical features in Sanfilippo Syndrome patients are overwhelmingly neurological. Typically, a Sanfilippo Syndrome patient has a normal early infancy. Developmental delays often are first manifestations of the disease. Several behavioral disturbances are a prominent feature of mild childhood, such as progressive dementia which can lead to a "quiet phase" of withdrawal and developmental regression. Typically, a Sanfilippo Syndrome patient survives to late teens or early 20s.

A clinical trial was conducted using a recombinant human heparan-N-sulfatase (rhHNS) administered intrathecally (IT) via a surgically implanted intrathecal drug delivery device (IDDD) to subjects with MPS-IIIA. The primary objective of the study was to determine the safety and tolerability of the rhHNS. Secondary objectives of the study included the assessment of cognitive performance, disability, behavior, HNS levels, and its derivatives in CSF, brain imaging and auditory brainstem activity.

For the study, 12 subjects with MPS-IIIA were enrolled. The subjects were grouped by age with 7 subjects ranging in age from 2-11 years, 3 subjects ranging in age from 12-17 years and 2 subjects ranging in age from 18-64 years. Four subjects were included in each of three dosing groups. Group I received 10 mg of rhHNS via an IDDD monthly (i.e., every 28 days +/−7 days) for a total of six months. Group II received 45 mg of rhHNS via an IDDD monthly (i.e., every 28 days +/−7 days) for a total of six months. Group III received 45 mg of rhHNS via an IDDD every 14 days +/−2 days for a monthly total dose of 90 mg for a total of six months.

The demographic details of the study subjects are provided below in Table 6.

TABLE 6

Study Subject Demographics and Baseline Characteristics

| Reporting group values | Group I (10 mg) | Group II (45 mg) | Group III (90 mg) |
|---|---|---|---|
| Number of subjects Age categorical Units: Subjects | 4 | 4 | 4 |
| Less than equal to (<=) 18 years | 3 | 3 | 4 |
| Between 18 and 65 years Age continuous Units: years arithmetic | 1 | 1 | 0 |
| mean standard deviation Gender, Male/Female Units: 0x | 9.15 ± 4.7 | 9.07 ± 9.8 | 10.64 ± 8.7 |
| Female | 1 | 2 | 1 |
| Male | 3 | 2 | 3 |

| Reporting group values | Total |
|---|---|
| Number of subjects Age categorical Units: Subjects | 12 |
| Less than equal to (<=) 18 years | 10 |
| Between 18 and 65 years Age continuous Units: years arithmetic | 2 |
| mean standard deviation | — |

TABLE 6-continued

Study Subject Demographics and Baseline Characteristics

Gender, Male/Female
Units: 0x

| | |
|---|---|
| Female | 4 |
| Male | 8 |

Pharmacokinetic Assessment

Figure 1B:
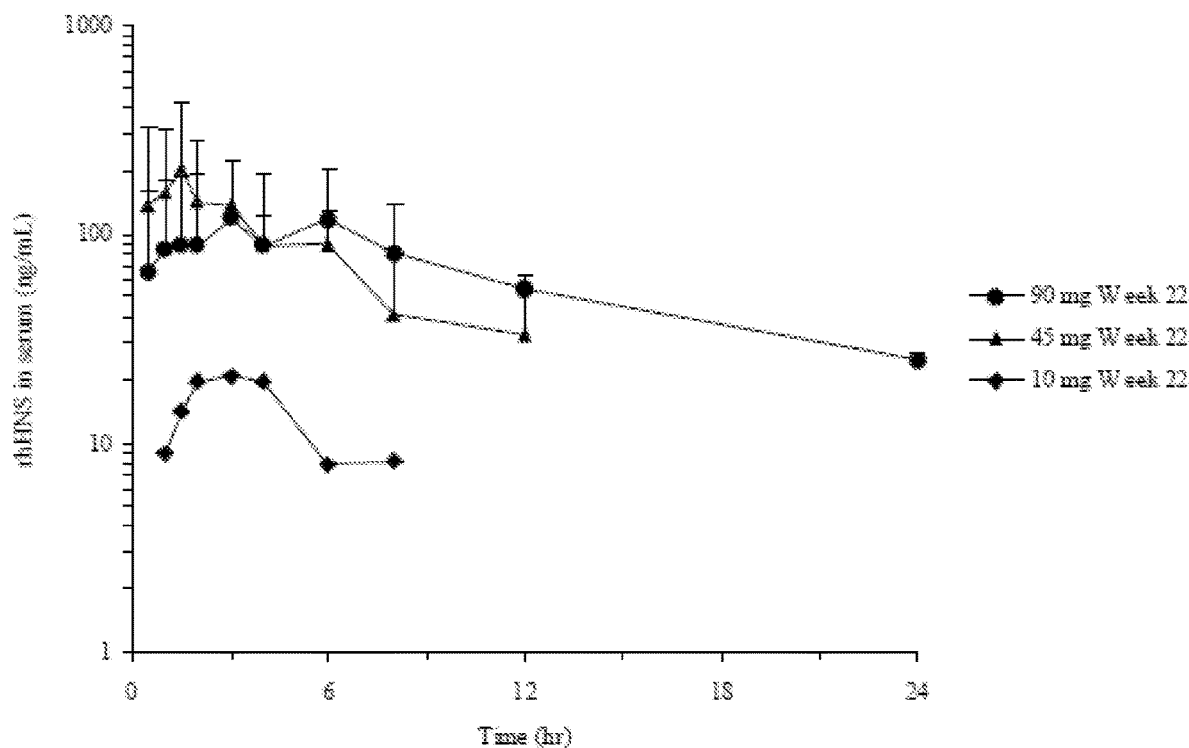
FIG. 1B shows dose dependent serum rhHNS concentration collected at Week 22 immediately prior to IT injection and over 24 hours following completion of IT injection.

Pharmacokinetic (PK) variables collected included the concentration of rhHNS in serum and cerebrospinal fluid and other standard PK variables over the course of the study. Pharmacokinetic exposure parameters were determined by using serum samples collected at Week 2 (Baseline) immediately prior to IT injection and Week 22, drawn at 0.5, 1, 1.5, 2, 3, 4, 6, 8, 12, 24, 48 (Day 2), and 72 (Day 3) hours following completion of IT injection. At Week 2 following IT administration, rhHNS exhibited biphasic serum concentration-time profiles across the 10, 45, and 90 mg IT dose groups. FIGS. 1A and 1B show dose-dependent serum PK after IT injection.

Immunogenicity

The anti-rhHNS antibody status in the cerebrospinal fluid (CSF) of study subjects was determined at base line and at week 26 of the study (Table 7). Subjects were either positive or negative for the presence of anti-rhHNS antibodies. If the anti-rhHNS antibody status was not determined the subject's status was reported as "missing."

TABLE 7 anti-rhHNS Antibody Status (CSF)

| End point values | Group I (10 mg) | Group II (45 mg) | Group III (90 mg) |
|---|---|---|---|
| Number of subjects analyzed | 4 | 4 | 4 |
| Negative (Baseline) | 4 | 4 | 4 |
| Positive (Baseline) | 0 | 0 | 0 |
| Missing (Baseline) | 0 | 0 | 0 |
| Negative (Week 26) | 1 | 1 | 2 |
| Positive (Week 26) | 0 | 0 | 0 |
| Missing (Week 26) | 3 | 3 | 2 |

The anti-rhHNS antibody status is the serum of study subjects was determined at base line and at week 26 of the study (Table 8). Subjects were either positive or negative for the presence of anti-rhHNS antibodies. If the anti-rhHNS antibody status was not determined the subject's status was reported as "missing."

TABLE 8 anti-rhHNS Antibody Status (CSF)

| End point values | Group I (10 mg) | Group II (45 mg) | Group III (90 mg) |
|---|---|---|---|
| Number of subjects analyzed | 4 | 4 | 4 |
| Negative (Baseline) | 4 | 3 | 3 |
| Positive (Baseline) | 0 | 1 | 1 |
| Missing (Baseline) | 0 | 0 | 0 |
| Negative (Week 26) | 1 | 2 | 2 |
| Positive (Week 26) | 2 | 0 | 0 |
| Missing (Week 26) | 1 | 2 | 2 |

Assessment of Cognitive Performance

The change from baseline in development quotient (DQ) using Bayley Scales of Infant Development Third Edition (BSID-III) and Kaufman Assessment Battery for Children Second Edition (KABC-II) was determined at week 22 of the study (Table 9). BSID-III was used to assess the cognitive development, language (receptive and expressive), and motor development (fine and gross), of infants and toddlers, ages 0-42 months. KABC-II was an individually administered measure of the processing and reasoning abilities of children and adolescents between the ages of 3 and 18 years and is an alternative to BSID-III. BSID-III DQ score is based on the cognitive domain. The DQ score was calculated from the data obtained from either BSID-III/KABC-II mental age equivalent of the child in months divided by the calendar age in months (multiplied by 100 to give percentage points). The data are expressed as units as measured on the rating scale+/−standard deviation.

TABLE 9

Change from Baseline in DQ using BSID-III or KABC-II

| End point values (units on scale +/− SD) | Group I (10 mg) | Group II (45 mg) | Group III (90 mg) |
|---|---|---|---|
| Number of subjects analyzed | 4 | 4 | 4 |
| Baseline (n = 2, 4, 4) | 51.91 (±27.292) | 43.24 (±23.112) | 51.87 (±36.095) |
| Change at Week 22 (n = 2, 4, 4) | −13.6 (±8.886) | −0.89 (±4.341) | −4.91 (±7.769) |

The change from baseline in development quotient (DQ) using Vineland Adaptive Behavioral Scales Second Edition (VABS-II) was determined at week 22 of the study (Table 10). VABS-II measures adaptive behaviors, including the ability to cope with environmental changes, to learn new everyday skills, and to demonstrate independence. This test measures 5 key domains: communication, daily living skills, socialization, motor skills, and the adaptive behavior composite (a composite of the other four domains). The Overall DQ score was calculated from the mean age-equivalent score obtained by averaging the age equivalent scores for all the sub-domains except for Gross and Fine motor skills. The data are expressed as units as measured on the rating scale+/−standard deviation.

TABLE 10

Change from Baseline in DQ using VABS-II

| End point values (units on scale +/− SD) | Group I (10 mg) | Group II (45 mg) | Group III (90 mg) |
|---|---|---|---|
| Number of subjects analyzed | 4 | 4 | 4 |
| Baseline (n = 4, 4, 4) | 44.78 (±24.747) | 47.24 (±26.612) | 47.71 (±33.687) |
| Change at Week 22 (n = 2, 2, 2) | −11.38 (±12.478) | −23.96 (±10.014) | −10.18 (±13.333) |

Disability Assessment

Figure 2:
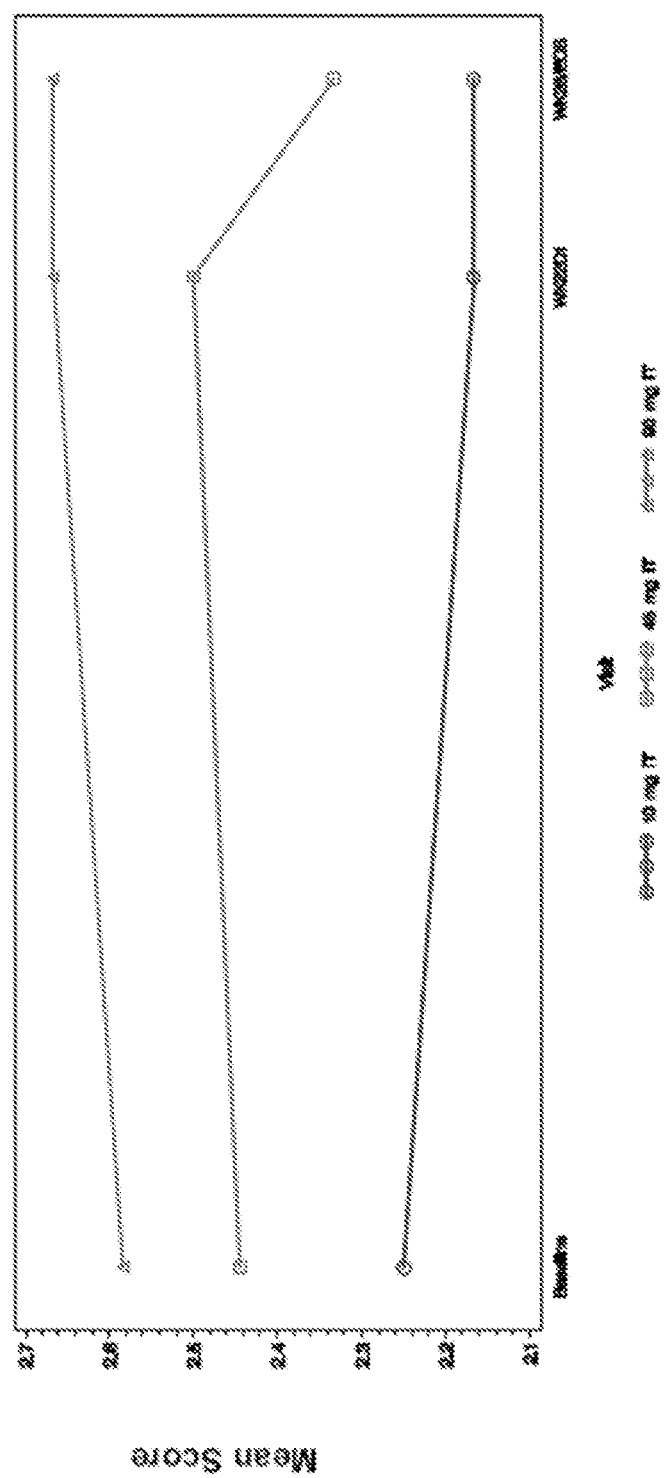
FIG. 2 shows mean total disability score for FPSS over time by dose group.

An assessment of Sanfilippo-specific disabilities was performed for all subjects using a Four Point Scoring System/Total Disability Score (FPSS/TDS) (Table 11). The parameters assessed by a parent questionnaire included motor function, expressive/speech language, and cognitive function. The Total Disability Score (TDS) is the average of the motor skills (MS), speech abilities (SA), and cognitive function (CF) scores. A lower score indicates developmental regression. Subjects were assessed at baseline, week 22 and week 26 of the study. The data are expressed as units as measured on the rating scale+/−standard deviation. FIG. 2 shows mean total disability score for FPSS over time by dose group.

TABLE 11

Change from Baseline in FPSS/TDS

| End point values (units on scale +/− SD) | Group I (10 mg) | Group II (45 mg) | Group III (90 mg) |
|---|---|---|---|
| Number of subjects analyzed | 4 | 4 | 4 |
| MS: Baseline (n = 4, 3, 4) | 2.5 (±0.58) | 3 (±0) | 3 (±0) |
| MS: Change at Week 22 (n = 4, 3, 4) | 0.3 (±0.5) | 0 (±0) | 0 (±0) |
| MS: Change at Week 26/EOS (n = 2, 2, 3) | 0 (±0) | 0 (±0) | 0 (±0) |
| SA: Baseline (n = 4, 3, 4) | 2 (±0.82) | 2 (±0) | 2 (±0.82) |
| SA: Change at Week 22 (n = 4, 3, 4) | −0.5 (±0.58) | 0.3 (±0.58) | 0.3 (±0.5) |
| SA: Change at Week 26/EOS (n = 2, 2, 3) | −0.5 (±0.71) | 0 (±0) | 0.3 (±0.58) |
| CF: Baseline (n = 4, 3, 4) | 2.3 (±0.5) | 2.3 (±0.58) | 2.8 (±0.5) |
| CF: Change at Week 22 (n = 4, 3, 4) | 0 (±0) | 0 (±0) | 0 (±0) |
| CF: Change at Week 26/EOS (n = 2, 2, 3) | 0 (±0) | 0 (±0) | 0 (±0) |
| TDS: Baseline (n = 4, 3, 4) | 2.25 (±0.569) | 2.44 (±0.192) | 2.58 (±0.319) |
| TDS: Change at Week 22 (n = 4, 3, 4) | −0.08 (±0.319) | 0.11 (±0.192) | 0.08 (±0.167) |
| TDS: Change at Week 26/EOS (n = 2, 2, 3) | −0.17 (±0.236) | 0 (±0) | 0.11 (±0.192) |

Behavioral Assessment

The change from baseline in Sanfilippo Behavior Rating Scale (SBRS) was determined for the study subjects at week 22 and week 26 (Table 12). The Sanfilippo Behavior Rating Scale is a parent-scored behavioral inventory that measures comprehensive language skills, expressive language skills, tantrums, mood and emotions, and other behaviors not otherwise classified. The summary of each score is the sum of the responses, within a given domain, for a given subject. The higher summary score indicates undesirable behavior. Behaviors that were assessed included Current Communication (CC), Past Communication (PC), Body Movements (BM), Interaction with Objects (IWO), Activity and Routines (AAR), Emotional Function (EF), Safety-consciousness (SC), Social Interaction (SI), Eye Contact (EC), Comfort Seeking (CS), Self-control/Compliance (SCC), Mood, Anger/Aggression (MAA), Self-gratification (SG). The data are expressed as units as measured on the rating scale+/−standard deviation.

TABLE 12

Change from Baseline in SBRS

| End point values (units on scale +/− SD) | Group I (10 mg) | Group II (45 mg) | Group III (90 mg) |
|---|---|---|---|
| Number of subjects analyzed | 4 | 4 | 4 |
| CC: Baseline (n = 4, 4, 2) | 8 (±5.48) | 6.3 (±6.85) | 10 (±5.66) |
| CC: Change at Week 22 (n = 4, 4, 2) | 5 (±13.44) | −0.3 (±1.26) | 1.5 (±2.12) |
| CC: Change at Week 26/EOS (n = 3, 2, 2) | 1.3 (±12.5) | −1 (±1.41) | 1.5 (±2.12) |
| PC: Baseline (n = 3, 2, 4) | 7.3 (±6.03) | 8.5 (±12.02) | 11 (±11.37) |
| PC: Change at Week 22 (n = 1, 0, 1) | −8 (±99999)[a] | 99999 (±99999) | 0 (±99999) |
| PC: Change at Week 26/EOS (n = 0, 0, 0) | 99999[b] (±99999) | 99999 (±99999) | 99999 (±99999) |
| Orality: Baseline (n = 2, 3, 3) | 7 (±9.9) | 10.3 (±2.08) | 17.3 (±10.26) |

TABLE 12-continued

Change from Baseline in SBRS

| End point values (units on scale +/− SD) | Group I (10 mg) | Group II (45 mg) | Group III (90 mg) |
|---|---|---|---|
| Orality: Change at Week 22 (n = 2, 3, 1) | 2 (±2.83) | 6 (±5.29) | 4 (±99999) |
| Orality: Change at Week 26/EOS (n = 1, 1, 1) | 0 (±99999) | 5 (±99999) | 4 (±99999) |
| BM: Baseline (n = 4, 4, 2) | 5 (±4.55) | 2.5 (±2.08) | 12 (±2.83) |
| BM: Change at Week 22 (n = 3, 4, 2) | 2.3 (±3.51) | 2 (±2.45) | −2 (±2.83) |
| BM: Change at Week 26/EOS (n = 3, 2, 2) | 0.3 (±1.53) | 0 (±0) | −2 (±2.83) |
| IWO: Baseline (n = 4, 3, 4) | 4.5 (±3.11) | 10.3 (±2.08) | 8.5 (±7.9) |
| IWO: Change at Week 22 (n = 4, 3, 3) | 3.3 (±4.27) | −2 (±4.58) | −2 (±3.46) |
| IWO: Change at Week 26/EOS (n = 2, 1, 3) | 1 (±1.41) | −1 (±99999) | −2 (±3.46) |
| AAR: Baseline (n = 1, 3, 4) | 6 (±99999) | 14.3 (±3.06) | 12.3 (±9.46) |
| AAR: Change at Week 22 (n = 1, 3, 4) | 8 (±99999) | 0.7 (±0.58) | −1.3 (±6.08) |
| AAR: Change at Week 26/EOS (n = 0, 1, 3) | 99999 (±99999) | 0 (±99999) | 1.7 (±2.08) |
| EF: Baseline (n = 3, 4, 4) | 2 (±3.46) | 2.5 (±3.11) | 7.5 (±5) |
| EF: Change at Week 22 (n = 3, 4, 4) | 5.3 (±1.15) | 0 (±1.41) | −2.3 (±3.5) |
| EF: Change at Week 26/EOS (n = 2, 2, 3) | 5 (±1.41) | 0.5 (±0.71) | −1.31 (±3.06) |
| SC: Baseline (n = 4, 4, 4) | 7.8 (±5.44) | 9.5 (±1.91) | 11.5 (±7.9) |
| SC: Change at Week 22 (n = 4, 4, 4) | 0.5 (±1) | 1.8 (±5.74) | −0.8 (±2.5) |
| SC: Change at Week 26/EOS (n = 3, 2, 3) | −1 (±2.65) | −3 (±2.83) | −1 (±3) |
| Fearfulness: Baseline (n = 3, 3, 3) | 7 (±7.81) | 10.3 (±8.74) | 11 (±6.08) |
| Fearfulness: Change at Week 22 (n = 3, 3, 3) | 2.7 (±1.15) | −1 (±5.2) | 2 (±1.73) |
| Fearfulness: Change at Week 26/EOS (n = 2, 1, 3) | 2.5 (±2.12) | −5 (±99999) | 2.3 (±1.53) |
| SI: Baseline (n = 4, 4, 4) | 11 (±3.37) | 12.5 (±2.38) | 14.5 (±6.76) |
| SI: Change at Week 22 (n = 4, 3, 4) | 3 (±4.76) | 0.3 (±4.04) | −0.5 (±3.7) |
| SI: Change at Week 26/EOS (n = 3, 2, 3) | 0 (±8) | −3.5 (±4.95) | −0.7 (±4.62) |
| EC: Baseline (n = 4, 4, 3) | 2.8 (±3.59) | 5.5 (±3.7) | 6.7 (±5.77) |
| EC: Change at Week 22 (n = 4, 4, 3) | 1.5 (±1.73) | 0 (±3.27) | −1 (±2.65) |
| EC: Change at Week 26/EOS (n = 3, 2, 3) | 0.3 (±0.58) | −2 (±2.83) | −0.7 (±3.06) |
| EE: Baseline (n = 2, 4, 4) | 8.5 (±4.95) | 7.3 (±1.71) | 8.3 (±3.3) |
| EE: Change at Week 22 (n = 1, 4, 4) | 2 (±99999) | −0.5 (±1.29) | −0.8 (±2.87) |
| EE: Change at Week 26/EOS (n = 0, 2, 3) | 99999 (±99999) | −1 (±1.41) | 0.7 (±1.15) |
| CS: Baseline (n = 4, 3, 4) | 10.3 (±5.32) | 10.3 (±3.06) | 16.5 (±6.56) |
| CS: Change at Week 22 (n = 3, 3, 3) | 1.7 (±4.73) | −1.7 (±3.06) | −2.3 (±3.21) |
| CS: Change at Week 26/EOS (n = 2, 1, 3) | 0 (±1.41) | −1 (±99999) | −2.3 (±3.21) |
| Attention: Baseline (n = 4, 4, 4) | 8.3 (±4.65) | 8.8 (±1.26) | 10.5 (±7.72) |
| Attention: Change at Week 22 (n = 4, 4, 4) | 1 (±3.16) | 2.5 (±2.38) | 2.3 (±1.71) |
| Attention: Change at Week 26/EOS (n = 2, 2, 3) | 1.5 (±2.12) | 0.5 (±0.71) | 3.3 (±1.15) |
| SCC: Baseline (n = 4, 4, 4) | 8 (±4.97) | 7.3 (±2.22) | 10 (±7.3) |
| SCC: Change at Week 22 (n = 3, 4, 4) | 0.3 (±4.51) | 3.3 (±3.2) | 2 (±1.83) |
| SCC: Change at Week 26/EOS (n = 3, 2, 3) | 0.7 (±4.04) | 0.5 (±0.71) | 2.7 (±1.53) |
| MAA: Baseline (n = 4, 3, 4) | 5.3 (±4.11) | 9.7 (±3.51) | 17.3 (±15.65) |
| MAA: Change at Week 22 (n = 2, 3, 4) | 5.5 (±7.78) | 3.3 (±5.13) | −0.3 (±2.5) |
| MAA: Change at Week 26/EOS (n = 3, 1, 3) | 1.7 (±3.06) | 4 (±99999) | −0.7 (±2.89) |
| SG: Baseline (n = 4, 3, 4) | 0.5 (±1) | 0.3 (±0.58) | 4.5 (±5.26) |
| SG: Change at Week 22 (n = 3, 3, 4) | −0.7 (±1.15) | 2 (±1) | −1 (±4.08) |
| SG: Change at Week 26/EOS (n = 3, 1, 3) | 0.3 (±0.58) | 1 (±99999) | 1 (±1) |

[a]99999 = SD not available;
[b]99999 = data not available.

Quality of Life Assessments

The change from baseline in Quality of Life (QoL) was determined using the Child Health Questionnaire™ Parent Form 50 (CHQ-PF50) for the study subjects at week 22 and week 26 (Table 13). CHQ-PF50 was designed to measure the physical and psychosocial well-being of children 5 years to 18 years of age, and consists of 13 health concepts, including 11 multi-item and two single item scales: Physical Function (PF), Role/Social-Emotional/Behavioral (REB), Role/Social-Physical (RP), bodily pain (BP), General Behavior (BE), Mental Health (MH), Self Esteem (SE), General Health Perceptions (GH), Change in Health (CH), Parental Impact-Emotional (PE), Parental Impact-Time (PT), Family Activities (FA), and Family Cohesion (FC).

Transformed scores for all subscales range from 0 to 100, with a higher score indicating better health. Physical and Psychosocial Summary measures (SM) were scored with the use of norm-based methods that standardize the scores to a mean (±Standard Deviation) of 50±10 on the basis of an assessment of the general United States population. The data are expressed as units as measured on the rating scale+/− standard deviation.

TABLE 13

Change from Baseline in CHQ-PF50

| End point values (units on scale +/− SD) | Group I (10 mg) | Group II (45 mg) | Group III (90 mg) |
|---|---|---|---|
| Number of subjects analyzed | 4 | 4 | 4 |
| PF: Baseline (n = 2, 4, 2) | 66.67 (±47.14) | 80.28 (±35.141) | 66.67 (±23.57) |
| PF: Change at Week 22 (n = 2, 4, 2) | −8.33 (±51.069) | −16.39 (±23.047) | 5.56 (±15.713) |
| PF: Change at Week 26/EOS (n = 1, 2, 1) | 33.33 (±99999)[a] | −24.44 (±34.57) | −11.11 (±99999) |

TABLE 13-continued

Change from Baseline in CHQ-PF50

| End point values (units on scale +/− SD) | Group I (10 mg) | Group II (45 mg) | Group III (90 mg) |
|---|---|---|---|
| RP: Baseline (n = 2, 4, 2) | 66.67 (±47.14) | 50 (±57.735) | 66.67 (±47.14) |
| RP: Change at Week 22 (n = 2, 4, 2) | 8.33 (±11.785) | 8.33 (±16.667) | 0 (±0) |
| RP: Change at Week 26/EOS (n = 1, 2, 1) | 33.33 (±99999) | 0 (±0) | 0 (±99999) |
| BP: Baseline (n = 2, 4, 2) | 90 (±14.14) | 67.5 (±29.86) | 30 (±0) |
| BP: Change at Week 22 (n = 2, 4, 2) | −20 (±56.57) | 7.5 (±15) | 45 (±7.07) |
| BP: Change at Week 26/EOS (n = 1, 2, 1) | 20 (±99999) | 0 (±0) | 50 (±99999) |
| GH: Baseline (n = 2, 4, 2) | 45.42 (±2.946) | 27.92 (±21.457) | 33.33 (±23.57) |
| GH: Change at Week 22 (n = 2, 4, 2) | −7.75 (±38.537) | −5.21 (±10.417) | 11.25 (±15.91) |
| GH: Change at Week 26/EOS(n = 1, 2, 1) | 17.5 (±99999) | 0 (±0) | 0 (±99999) |
| REB: Baseline (n = 2, 4, 2) | 66.67 (±47.14) | 41.67 (±50) | 50 (±70.711) |
| REB: Change at Week 22 (n = 2, 4, 2) | −38.89 (±86.424) | 11.11 (±64.788) | 0 (±0) |
| REB: Change at Week 26/EOS (n = 1, 2, 1) | 22.22 (±99999) | 0 (±0) | 0 (±99999) |
| BE: Baseline (n = 2, 4, 2) | 62.5 (±17.678) | 61.04 (±15.296) | 45.83 (±11.785) |
| BE: Change at Week 22 (n = 2, 4, 2) | 12.08 (±8.839) | −2.92 (±15.716) | −2.08 (±2.946) |
| BE: Change at Week 26/EOS (n = 1, 2, 1) | 30.83 (±99999) | −14.37 (±14.437) | −8.33 (±99999) |
| MH: Baseline (n = 2, 4, 2) | 75 (±7.07) | 68.8 (±10.31) | 10 (±14.14) |
| MH: Change at Week 22 (n = 2, 4, 2) | 0 (±21.21) | −2.5 (±16.58) | 17.5 (±17.68) |
| MH: Change at Week 26/EOS (n = 1, 2, 1) | 15 (±99999) | −5 (±7.07) | 5 (±99999) |
| SE: Baseline (n = 2, 4, 2) | 62.5 (±5.893) | 61.46 (±18.122) | 47.92 (±14.731) |
| SE: Change at Week 22 (n = 2, 4, 2) | 0 (±11.785) | −3.13 (±7.116) | −4.17 (±5.893) |
| SE: Change at Week 26/EOS (n = 1, 2, 1) | 16.67 (±99999) | 8.33 (±11.785) | −8.33 (±99999) |
| PE: Baseline (n = 2, 4, 2) | 66.67 (±47.14) | 27.08 (±22.948) | 20.83 (±17.678) |
| PE: Change at Week 22 (n = 2, 4, 2) | −8.33 (±82.496) | −2.08 (±14.232) | 4.17 (±5.893) |
| PE: Change at Week 26/EOS (n = 1, 2, 1) | 16.67 (±99999) | −4.17 (±5.893) | 0 (±99999) |
| PT: Baseline (n = 2, 4, 2) | 50 (±70.711) | 33.33 (±28.689) | 5.56 (±7.857) |
| PT: Change at Week 22 (n = 2, 4, 2) | 11.11 (±62.854) | −5.56 (±26.45) | 16.67 (±23.57) |
| PT: Change at Week 26/EOS (n = 1, 2, 1) | 44.44 (±99999) | −5.56 (±23.57) | 0 (±99999) |
| FA: Baseline (n = 2, 4, 2) | 56.25 (±61.872) | 42.71 (±13.767) | 10.42 (±14.731) |
| FA: Change at Week 22 (n = 2, 4, 2) | 0 (±58.926) | −7.29 (±13.767) | 0 (±0) |
| FA: Change at Week 26/EOS (n = 1, 2, 1) | 16.67 (±99999) | −6.25 (±2.946) | 0 (±99999) |
| FC: Baseline (n = 2, 4, 2) | 57.5 (±38.89) | 72.5 (±14.43) | 15 (±21.21) |
| FC: Change at Week 22 (n = 2, 4, 2) | 27.5 (±38.89) | −6.3 (±12.5) | 15 (±21.21) |
| FC: Change at Week 26/EOS (n = 1, 2, 1) | 55 (±99999) | 0 (±0) | 30 (±99999) |
| SM Physical: Baseline (n = 2, 4, 2) | 38.44 (±23.545) | 31.62 (±23.071) | 31.27 (±18.193) |
| SM Physical: Change at Week 22 (n = 2, 4, 2) | −4.63 (±29.276) | −1.82 (±6.112) | 9.21 (±5.095) |
| SM Physical: Change at Week 26/EOS (n = 1, 2, 1) | 17.25 (±99999) | −4.99 (±8.195) | 4.96 (±99999) |
| SM Psychosocial: Baseline (n = 2, 4, 2) | 42.16 (±14.06) | 33.8 (±10.879) | 17.57 (±2.418) |
| SM Psychosocial: Change at Week 22 (n = 2, 4, 2) | −1.18 (±23.341) | −0.26 (±14.004) | 2.27 (±4.972) |
| SM Psychosocial: Change at Week 26/EOS (n = 1, 2, 1) | 13.64 (±99999) | −1.58 (±2.584) | −2.29 (±99999) |

$^a$99999 = SD not available.

The change from baseline in Quality of Life (QoL) was determined using the Infant Toddler Quality of Life Questionnaire™ (ITQOL) for the study subjects at week 22 and week 26 (Table 14). ITQOL was developed for children at least 2 months of age up to 5 years and assesses the physical, mental, and social well-being of the child and assesses the quality of the parent/guardian's life. Parameters measured included: Overall Health (OH), Physical Abilities (PA), Growth And Development (GAD), Bodily Pain (BP), Temperament And Moods (TAM), General Behavior (GEB), Global Behavior (GLB), Getting Along (GA), General Health Perceptions (GHP), PI-Emotion (PIE), PI-Time (PIT), Family Cohesion (FC). The data are expressed as units as measured on the rating scale+/−standard deviation.

TABLE 14

Change from Baseline in ITQOL

| End point values (units on scale +/− SD) | Group I (10 mg) | Group II (45 mg) | Group III (90 mg) |
|---|---|---|---|
| Number of subjects analyzed | 4 | 4 | 4 |
| OH: Baseline (n = 2, 3, 2) | 80 (±28.28) | 56.7 (±49.07) | 65 (±49.5) |
| OH: Change at Week 22 (n = 2, 2, 2) | 0 (±0) | −12.5 (±17.68) | 15 (±21.21) |
| OH: Change at Week 26/EOS (n = 1, 0, 0) | 0 (±99999)$^a$ | 99999 (±99999) | 99999 (±99999) |
| PA: Baseline (n = 2, 3, 2) | 83.35 (±9.405) | 75.57 (±39.496) | 93.35 (±4.738) |
| PA: Change at Week 22 (n = 2, 2, 2) | 5 (±11.738) | 1.65 (±11.809) | −1.7 (±2.404) |
| PA: Change at Week 26/EOS (n = 1, 0, 0) | −3.3 (±99999) | 99999 (±99999) | 99999 (±99999) |
| GAD: Baseline (n = 2, 3, 2) | 57.2 (±18.102) | 60.83 (±25.658) | 56.8 (±6.081) |
| GAD: Change at Week 22 (n = 2, 2, 2) | −14.7 (±28.709) | −22.5 (±7.071) | 18.2 (±0.99) |
| GAD: Change at Week 26/EOS (n = 1, 0, 0) | 3.1 (±99999) | 99999 (±99999) | 99999 (±99999) |
| BP: Baseline (n = 2, 3, 2) | 95.85 (±5.869) | 58.33 (±36.294) | 62.5 (±29.416) |
| BP: Change at Week 22 (n = 2, 2, 2) | −29.2 (±17.678) | 25 (±11.738) | 12.5 (±41.154) |

TABLE 14-continued

Change from Baseline in ITQOL

| End point values (units on scale +/− SD) | Group I (10 mg) | Group II (45 mg) | Group III (90 mg) |
|---|---|---|---|
| BP: Change at Week 26/EOS (n = 1, 0, 0) | −16.7 (±99999) | 99999 (±99999) | 99999 (±99999) |
| TAM: Baseline (n = 2, 3, 2) | 72.2 (±17.678) | 68.97 (±21.731) | 52.8 (±15.698) |
| TAM: Change at Week 22 (n = 2, 2, 2) | −23.6 (±21.637) | −2.75 (±33.446) | −5.6 (±19.658) |
| TAM: Change at Week 26/EOS (n = 1, 0, 0) | −12.8 (±99999) | 99999 (±99999) | 99999 (±99999) |
| GEB: Baseline (n = 2, 3, 2) | 58.35 (±32.456) | 34.73 (±17.465) | 12.5 (±5.94) |
| GEB: Change at Week 22 (n = 2, 2, 2) | −12.5 (±8.91) | 7.25 (±25.102) | 18.75 (±0.071) |
| GEB: Change at Week 26/EOS (n = 1, 0, 0) | −8.3 (±99999) | 99999 (±99999) | 99999 (±99999) |
| GLB: Baseline (n = 2, 3, 2) | 57.5 (±38.89) | 40 (±34.64) | 0 (±0) |
| GLB: Change at Week 22 (n = 2, 2, 2) | −15 (±21.21) | 0 (±42.43) | 0 (±0) |
| GLB: Change at Week 26/EOS (n = 1, 0, 0) | 0 (±99999) | 99999 (±99999) | 99999 (±99999) |
| GA: Baseline (n = 2, 3, 2) | 62.5 (±17.678) | 55 (±15) | 35.85 (±1.202) |
| GA: Change at Week 22 (n = 2, 2, 2) | −22.5 (±10.607) | −2.5 (±22.345) | −1.65 (±16.476) |
| GA: Change at Week 26/EOS (n = 1, 0, 0) | −16.7 (±99999) | 99999 (±99999) | 99999 (±99999) |
| GHP: Baseline (n = 2, 3, 2) | 48.9 (±4.808) | 31.8 (±20.178) | 57.95 (±36.982) |
| GHP: Change at Week 22 (n = 2, 2, 2) | −18.2 (±22.486) | −5.7 (±1.556) | −3.8 (±11.879) |
| GHP: Change at Week 26/EOS (n = 1, 0, 0) | 0 (±99999) | 99999 (±99999) | 99999 (±99999) |
| PIE: Baseline (n = 2, 3, 2) | 78.55 (±30.335) | 48.83 (±33.024) | 41.65 (±23.547) |
| PIE: Change at Week 22 (n = 2, 2, 2) | −35.7 (±25.314) | −3.6 (±25.314) | 4.75 (±3.323) |
| PIE: Change at Week 26/EOS (n = 1, 0, 0) | −17.8 (±99999) | 99999 (±99999) | 99999 (±99999) |
| PIT: Baseline (n = 2, 3, 2) | 73.8 (±37.052) | 49.2 (±26.264) | 45.25 (±63.993) |
| PIT: Change at Week 22 (n = 2, 2, 2) | −33.35 (±6.718) | 7.2 (±23.617) | 23.8 (±20.223) |
| PIT: Change at Week 26/EOS (n = 1, 0, 0) | −28.6 (±99999) | 99999 (±99999) | 99999 (±99999) |
| FC: Baseline (n = 2, 3, 2) | 85 (±0) | 76.7 (±14.43) | 42.5 (±60.1) |
| FC: Change at Week 22 (n = 2, 2, 2) | −12.5 (±17.68) | −12.5 (±17.68) | −27.5 (±99999) |
| FC: Change at Week 26/EOS (n = 1, 0, 0) | −25 (±99999) | 99999 (±99999) | 99999 (±99999) |

[a]99999 signifies standard deviation not reported as there was only 1 evaluable subject and data was not available for the specific measure.

The change from baseline in Quality of Life (QoL) was also determined using the Children's Sleep Habits Rating Scale for the study subjects at week 22 and week 26 (Table 15). The Children's Sleep Habits rating scale consists of 35 parameters that yield a Total Sleep Disturbance score (TSDS), as well as eight subscale scores (Bedtime Resistance (BR), Sleep Duration (SD), Parasomnias (P), Sleep Disordered Breathing (SDB), Night Waking (NW), Daytime Sleepiness (DS), Sleep Anxiety (SA), and Sleep Onset Delay (SOD)). The questionnaire was designed for children aged 4 through 12 years. The data are expressed as units as measured on the rating scale+/−standard deviation.

TABLE 15

Change from Baseline in Children's Sleep Habits Rating Scale

| End point values (units on scale +/− SD) | Group I (10 mg) | Group II (45 mg) | Group III (90 mg) |
|---|---|---|---|
| Number of subjects analyzed | 4 | 4 | 4 |
| BR: Baseline (n = 4, 4, 4) | 8.8 (±1.89) | 7.3 (±2.5) | 11.5 (±4.65) |
| BR: Change at Week 22 (n = 4, 4, 4) | −1.3 (±1.89) | 1.3 (±0.96) | −0.8 (±0.96) |
| BR: Change at Week 26/EOS (n = 3, 2, 2) | −1 (±1) | 1 (±1.41) | 0 (±0) |
| SOD: Baseline (n = 4, 4, 4) | 1.5 (±1) | 1.8 (±0.96) | 2.3 (±0.96) |
| SOD: Change at Week 22 (n = 4, 4, 4) | 0 (±0.82) | 0 (±0.82) | 0 (±0.82) |
| SOD: Change at Week 26/EOS (n = 3, 2, 2) | −0.3 (±0.58) | −0.5 (±0.71) | 0 (±1.41) |
| SD: Baseline (n = 4, 4, 4) | 5.3 (±2.22) | 6.5 (±2.65) | 6 (±2.16) |
| SD: Change at Week 22 (n = 4, 4, 4) | −0.8 (±2.99) | −0.5 (±1.29) | 1.3 (±1.5) |
| SD: Change at Week 26/EOS (n = 3, 2, 2) | −1.7 (±2.89) | −1 (±1.41) | 1 (±1.41) |
| SA: Baseline (n = 4, 4, 4) | 7 (±1.15) | 6 (±1.41) | 8.3 (±3.3) |
| SA: Change at Week 22 (n = 4, 4, 3) | −1.5 (±1.91) | 0.8 (±1.71) | −0.3 (±0.58) |
| SA: Change at Week 26/EOS (n = 3, 2, 2) | −0.7 (±1.15) | 0 (±1.41) | −0.5 (±0.71) |
| NW: Baseline (n = 4, 4, 4) | 4.3 (±1.5) | 5.5 (±1.91) | 5.8 (±2.5) |
| NW: Change at Week 22 (n = 4, 4, 4) | −0.3 (±2.06) | 0 (±1.63) | −0.5 (±0.58) |
| NW: Change at Week 26/EOS (n = 3, 2, 2) | −1 (±1.73) | −0.5 (±0.71) | 0 (±0) |
| P: Baseline (n = 2, 4, 4) | 8.5 (±0.71) | 10 (±2.31) | 12 (±2.94) |
| P: Change at Week 22 (n = 2, 4, 4) | −1 (±0) | 0.3 (±3.4) | −0.3 (±2.87) |
| P: Change at Week 26/EOS (n = 1, 2, 2) | −1 (±99999) | −1 (±0) | −0.5 (±0.71) |
| SDB: Baseline (n = 4, 4, 4) | 3.3 (±0.5) | 4.3 (±0.5) | 5.8 (±3.2) |
| SDB: Change at Week 22 (n = 4, 4, 3) | 0.8 (±0.96) | 0.5 (±1.73) | −1.7 (±2.89) |
| SDB: Change at Week 26/EOS (n = 3, 2, 2) | 0.7 (±1.15) | −0.5 (±0.71) | 0 (±0) |
| DS: Baseline (n = 4, 4, 4) | 9.5 (±1.29) | 11.5 (±3.87) | 11.3 (±3.4) |
| DS: Change at Week 22 (n = 4, 4, 4) | −0.3 (±0.5) | 0.5 (±0.58) | 0.5 (±2.65) |
| DS: Change at Week 26/EOS (n = 3, 2, 2) | 0.7 (±1.15) | 1 (±0) | 1 (±1.41) |
| TSDS: Baseline (n = 2, 4, 4) | 42.5 (±2.12) | 50.3 (±12.28) | 58.8 (±16.82) |
| TSDS: Change at Week 22 (n = 2, 4, 2) | 1.5 (±4.95) | 2 (±5.83) | 2 (±5.66) |
| TSDS: Change at Week 26/EOS (n = 1, 2, 2) | −2 (±99999) | −2 (±4.24) | 1 (±2.83) |

Biomarkers

Figure 3:
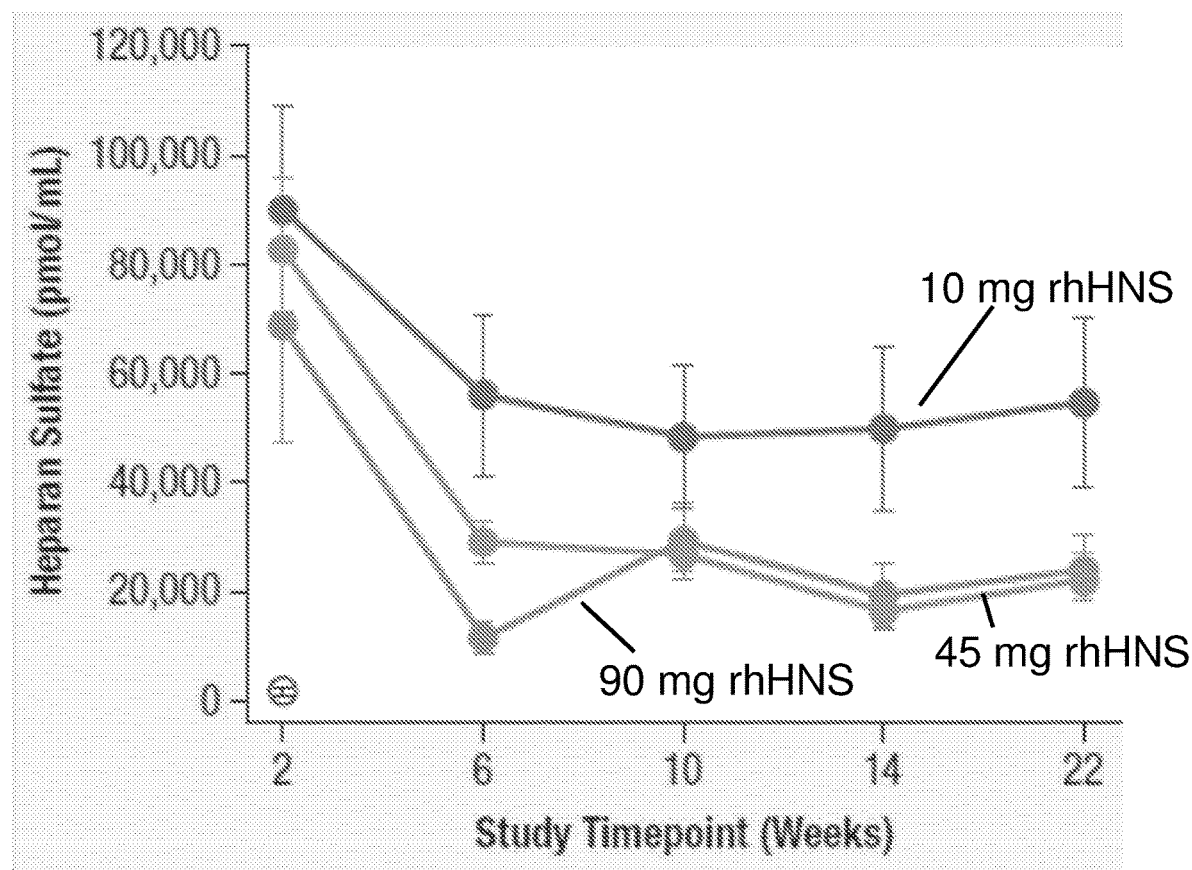
FIG. 3 shows the total heparan sulfate (HS) concentrations in the cerebrospinal fluid (CSF) of study subjects at weeks 2, 6, 10, 14, and 22. The data are expressed as pmol analyte/mL+/−standard deviation.

Heparan sulfate (HS) is the primary accumulating metabolite in Sanfilippo Syndrome Type A. The level of the glycosaminoglycan (GAG) heparan sulfate in CSF was measured at various time points during the study as an important biomarker to indicate in vivo activity of rhHNS in the central nervous system. The change in total heparan sulfate (HS) and heparan sulfate derivatives (HSD) concentrations from baseline were measured in the cerebrospinal fluid (CSF) of study subjects at weeks 6, 10, 14, 18, and 22. Levels of total heparan sulfate (SPTHS) and its GAG derivatives (i.e., by a non-reducing end assay, SPNREA) were evaluated using a Sensi-Pro (SP) high performance lipid chromatography based assay (Zacharon). The data are expressed as pmol analyte/mL+/−standard deviation. (FIG. 3)

As shown in Table 16, mean total GAG levels were reduced at each of the three dose levels over the course of the study.

TABLE 16

Change from Baseline in HS and HSD in CSF

| End point values (pmol/mL +/− SD) | Group I (10 mg) | Group II (45 mg) | Group III (90 mg) |
|---|---|---|---|
| Number of subjects analyzed | 4 | 4 | 4 |
| SPTHS: Baseline (n = 4, 4, 4) | 90570.5 (±38088.67) | 69049.7 (±42659.28) | 83287 (±26012.16) |
| SPTHS: Change at Week 6 (n = 4, 2, 2) | −34167.7 (±20439.34) | −41331.4 (±38967.66) | −65862.6 (±23010.52) |
| SPTHS: Change at Week 10 (n = 4, 4, 3) | −41825.4 (±13482.5) | −39441.8 (±29771.14) | −54343.7 (±25891.78) |
| SPTHS: Change at Week 14 (n = 4, 3, 3) | −40309 (±15107.94) | −32249.2 (±21862.89) | −64763.9 (±25285.97) |
| SPTHS: Change at Week 22 (n = 4, 4, 4) | −35469.5 (±20922.54) | −44669.5 (±38360.07) | −60931.7 (±20699.36) |
| SPNREA: Baseline (n = 4, 4, 4) | 1255.93 (±471.403) | 1198.34 (±627.436) | 1487.67 (±329.79) |
| SPNREA: Change at Week 6 (n = 4, 2, 2) | −213.25 (±330.836) | −677.79 (±393.281) | −1022.53 (±163.905) |
| SPNREA: Change at Week 10 (n = 4, 4, 3) | −411.77 (±268.961) | −533.38 (±476.259) | −788.65 (±390.761) |
| SPNREA: Change at Week 14 (n = 4, 3, 3) | −359.15 (±272.695) | −491.24 (±177.701) | −1033.58 (±371.566) |
| SPNREA: Change at Week 22 (n = 4, 4, 4) | 254.07 (±333.649) | −686.13 (±517.558) | −877.84 (±435.044) |

Figure 4:
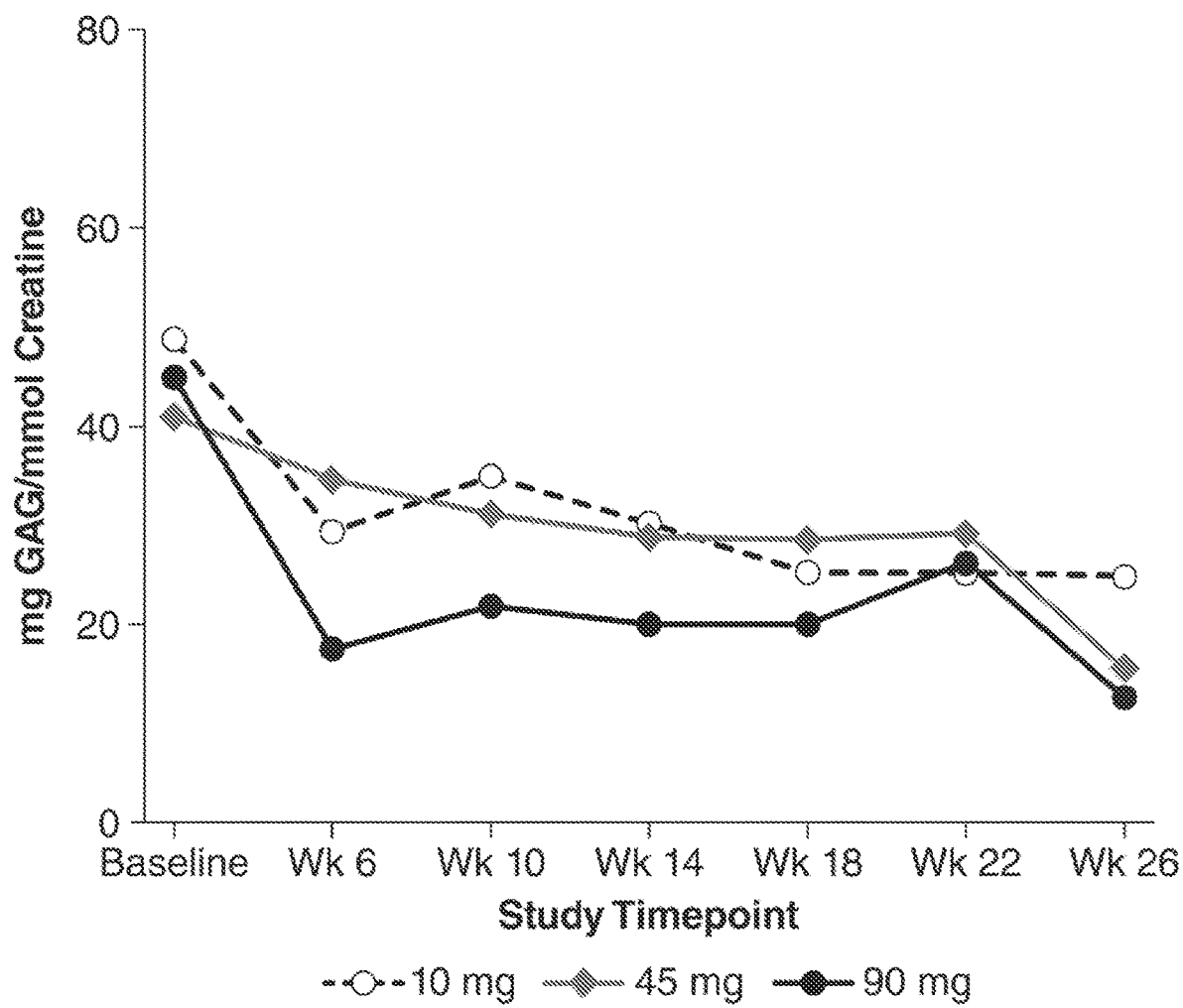
FIG. 4 shows urine glycosaminoglycan (GAG) levels (mg), normalized for mmol of urine creatinine. The mean values of urine GAG are displayed over time and by dose group.

Urine glycosaminoglycan (GAG) levels (mg) were normalized for mmol of urine creatinine. The mean values of urine GAG are displayed over time and by dose group in FIG. 4. Mean urinary GAG levels were reduced at each of the 3 dose levels, with the decline evident after the first dose of IT rhHNS (ie, observed at Week 6, with the sample taken immediately before the second dose).

Brain Imaging Assessment

The change from baseline in brain Magnetic Resonance Imaging (MRI) of study subjects was determined at week 22 (Table 17). Brain MRI was used to measure grey matter volume (GMV), white matter volume (WMV) and intracranial cerebrospinal fluid volume (ICSFV). The ICSFV includes the ventricular space and additional CSF spaces. The data are expressed in mL+/−the standard deviation.

TABLE 17

Change from Baseline in Brain MRI

| End point values (average mL +/− SD) | Group I (10 mg) | Group II (45 mg) | Group III (90 mg) |
|---|---|---|---|
| Number of subjects analyzed | 4 | 4 | 4 |
| GMV: Baseline | 550.5 (±111.043) | 534.25 (±117.291) | 600.28 (±67.884) |
| GMV: Change at Week 22 | −42.84 (±36.793) | −33.7 (±24.161) | −32.87 (±36.862) |
| WMV: Baseline | 403.72 (±105.575) | 348.28 (±76.854) | 442.45 (±79.814) |
| WMV: Change at Week 22 | −2.86 (±13.997) | 3.33 (±11.419) | −0.44 (±9.793) |
| ICSFV: Baseline | 26.152 (±9.2975) | 22.904 (±20.8459) | 20.925 (±15.9681) |
| ICSFV: Change at Week 22 | 4.739 (±4.6455) | 2.886 (±3.9153) | 7.375 (±6.6573) |

Auditory Brainstem Assessments

The change from baseline in mean Auditory Brainstem Response (ABR) of study subjects was determined at week 22 (Table 18). ABR assessments were conducted under anesthesia and measured the electrical response evoked by acoustic stimuli as sound is processed along the auditory pathway. Mean ABR air and bone conduction threshold were assessed. The data are expressed as decibels above normal adult hearing level+/−standard deviation.

TABLE 18

Change from Baseline in ABR

| End point values | Group I (10 mg) | Group II (45 mg) | Group III (90 mg) |
| --- | --- | --- | --- |
| Number of subjects analysed | 4 | 4 | 4 |
| Right Ear: Baseline (n = 1, 2, 3) | 62.5 (±99999)[a] | 56.25 (±8.839) | 49.17 (±14.216) |
| Right Ear: Change at Week 22 (n = 1, 2, 3) | −10 (±99999) | −3.75 (±15.91) | −0.83 (±22.407) |
| Left Ear: Baseline (n = 2, 2, 4) | 52.5 (±10.607) | 55 (±7.071) | 44.38 (±24.696) |
| Left Ear: Change at Week 22 (n = 2, 2, 4) | 5 (±7.071) | −5 (±14.142) | 3.13 (±10.68) |

[a]99999 signifies standard deviation not reported as there was only 1 evaluable subject.

The change from baseline in mean Auditory Brainstem Response (ABR) Latencies of study subjects was determined at week 22 (Table 19). ABR assessments were conducted under anesthesia and measured the electrical response evoked by acoustic stimuli as sound is processed along the auditory pathway. The Inter-peak Latencies (IPL) were calculated by subtracting the Absolute Latencies (AL). The Inter-aural latencies (IAL) were calculated by subtracting the absolute wave V latencies of the right and left ear. IAL, IPL and AL were reported. The data are expressed as milliseconds+/−standard deviation for either the right ear (RE) or the left ear (LE).

TABLE 19

Change from Baseline in ABR: Latencies

| End point values (ms +/− SD) | Group I (10 mg) | Group II (45 mg) | Group III (90 mg) |
| --- | --- | --- | --- |
| Number of subjects analyzed | 4 | 4 | 4 |
| RE, IPL I-III: Baseline (n = 3, 3, 3) | 2.29 (±0.257) | 2.53 (±0.153) | 2.33 (±0.193) |
| RE, IPL I-III: Change at Week 22 (n = 3, 3, 2) | −0.09 (±0.147) | −0.11 (±0.183) | 0.07 (±0.014) |
| RE, IPL III-V: Baseline (n = 3, 3, 3) | 2.04 (±0.24) | 2.17 (±0.261) | 1.96 (±0.119) |
| RE, IPL III-V: Change at Week 22 (n = 3, 3, 2) | −0.08 (±0.185) | −0.06 (±0.304) | 0.06 (±0.085) |
| RE, IPL I-V: Baseline (n = 3, 3, 3) | 4.34 (±0.047) | 4.71 (±0.352) | 4.29 (±0.238) |
| RE, IPL I-V: Change at Week 22 (n = 3, 3, 3) | −0.17 (±0.269) | −0.17 (±0.187) | 0.2 (±0.131) |
| LE, IPL I-III: Baseline (n = 3, 3, 4) | 2.32 (±0.206) | 2.53 (±0.153) | 2.4 (±0.303) |
| LE, IPL I-III: Change at Week 22 (n = 3, 3, 3) | −0.01 (±0.129) | −0.24 (±0.065) | 0.11 (±0.219) |
| LE, IPL III-V: Baseline (n = 3, 3, 4) | 2.06 (±0.255) | 2.15 (±0.225) | 2.09 (±0.311) |
| LE, IPL III-V: Change at Week 22 (n = 3, 3, 3) | −0.02 (±0.075) | 0.09 (±0.091) | 0.06 (±0.04) |
| LE, IPL I-V: Baseline (n = 3, 3, 4) | 4.39 (±0.264) | 4.68 (±0.33) | 4.48 (±0.394) |
| LE, IPL I-V: Week 22 (n = 3, 3, 3) | −0.03 (±0.185) | −0.15 (±0.07) | 0.17 (±0.191) |
| IAL: Baseline (n = 3, 3, 3) | −0.05 (±0.061) | −0.07 (±0.058) | 0.07 (±0.081) |
| IAL: Change at Week 22 (n = 3, 3, 3) | 0.04 (±0.301) | 0.28 (±0.312) | 0.46 (±0.849) |
| AL-RE, WI: Baseline (n = 3, 3, 3) | 1.73 (±0.237) | 1.59 (±0.156) | 1.76 (±0.012) |
| AL-RE, WI: Change at Week 22 (n = 3, 3, 3) | 0 (±0.466) | 0.46 (±0.54) | 0.47 (±0.987) |
| AL-RE, WIII: Baseline (n = 3, 3, 2) | 4.02 (±0.45) | 4.12 (±0.197) | 4.09 (±0.181) |
| AL-RE, WIII: Change at Week 22 (n = 3, 3, 2) | −0.09 (±0.355) | 0.35 (±0.687) | −0.03 (±0.042) |
| AL-RE, WV: Baseline (n = 3, 3, 3) | 6.06 (±0.283) | 6.3 (±0.454) | 6.06 (±0.227) |
| AL-RE, WV: Change at Week 22 (n = 3, 3, 3) | −0.17 (±0.478) | 0.29 (±0.633) | 0.67 (±1.109) |
| AL-LE, WI: Baseline (n = 3, 3, 4) | 1.73 (±0.13) | 1.68 (±0.144) | 1.78 (±0.233) |
| AL-LE, WI: Change at Week 22 (n = 3, 3, 3) | −0.18 (±0.111) | 0.16 (±0.33) | 0.04 (±0.16) |
| AL-LE, WIII: Baseline (n = 3, 3, 4) | 4.05 (±0.323) | 4.22 (±0.189) | 4.18 (±0.504) |
| AL-LE, WIII: Change at Week 22 (n = 3, 3, 3) | −0.19 (±0.165) | −0.08 (±0.266) | 0.15 (±0.306) |
| AL-LE, WV: Baseline (n = 3, 3, 4) | 6.12 (±0.278) | 6.36 (±0.412) | 6.26 (±0.612) |
| AL-LE, WV: Change at Week 22 (n = 3, 3, 4) | −0.21 (±0.178) | 0.01 (±0.324) | 0.24 (±0.227) |

The change from baseline in mean Auditory Brainstem Response (ABR) Amplitude of study subjects was determined at week 22 (Table 20). ABR assessments were conducted under anesthesia and measured the electrical response evoked by acoustic stimuli as sound is processed along the auditory pathway. The change from baseline in ABR amplitudes by left ear (LE) and right ear (RE) was recorded. The data are expressed as microvolt (mcV)+/− standard deviation.

TABLE 20

Change from Baseline in ABR: Amplitude

| End point values (mcV +/_SD) | Group I (10 mg) | Group II (45 mg) | Group III (90 mg) |
|---|---|---|---|
| Number of subjects analyzed | 4 | 4 | 4 |
| RE, Wave I: Baseline (n = 2, 3, 3) | 0.49 (±0.042) | 0.42 (±0.118) | 0.26 (±0.097) |
| RE, Wave I: Change at Week 22 (n = 2, 3, 3) | −0.23 (±0.042) | −0.17 (±0.147) | −0.03 (±0.216) |
| RE, Wave III: Baseline (n = 2, 3, 3) | 0.33 (±0.156) | 0.35 (±0.195) | 0.24 (±0.113) |
| RE, Wave III: Change at Week 22 (n = 2, 3, 2) | −0.05 (±0.099) | −0.12 (±0.117) | −0.16 (±0.156) |
| RE, Wave V: Baseline (n = 2, 3, 3) | 0.64 (±0.403) | 0.47 (±0.144) | 0.32 (±0.101) |
| RE, Wave V: Change at Week 22 (n = 2, 3, 3) | −0.28 (±0.354) | −0.09 (±0.145) | −0.14 (±0.201) |
| LE, Wave I: Baseline (n = 2, 3, 4) | 0.4 (±0.028) | 0.44 (±0.199) | 0.26 (±0.133) |
| LE, Wave I: Change at Week 22 (n = 2, 3, 3) | −0.1 (±0.17) | 0.02 (±0.221) | −0.01 (±0.135) |
| LE, Wave III: Baseline (n = 2, 3, 4) | 0.22 (±0.106) | 0.38 (±0.194) | 0.21 (±0.102) |
| LE, Wave III: Change at Week 22 (n = 2, 3, 3) | 0.05 (±0.057) | −0.09 (±0.188) | 0.02 (±0.047) |
| LE, Wave V: Baseline (n = 2, 3, 4) | 0.52 (±0.269) | 0.48 (±0.123) | 0.29 (±0.17) |
| LE, Wave V: Change at Week 22 (n = 2, 3, 4) | −0.13 (±0.24) | −0.02 (±0.134) | −0.01 (±0.085) |

The change from baseline in mean Auditory Brainstem Response (ABR) Amplitude Ratio of study subjects was determined at week 22 (Table 21). ABR assessments were conducted under anesthesia and measured the electrical response evoked by acoustic stimuli as sound is processed along the auditory pathway. Data for change from baseline in ABR amplitudes (A), log-transformed amplitudes (LTA), square-root transformed amplitudes (STA) by left ear (LE) and right (RE) wave V/I in ratio was reported. The data are expressed as a ratio+/−standard deviation.

TABLE 21

Change from Baseline in ABR: Amplitude Ratio

| End point values (ratio +/− SD) | Group I (10 mg) | Group II (45 mg) | Group III (90 mg) |
|---|---|---|---|
| Number of subjects analyzed | 4 | 4 | 4 |
| A-RE, Wave V/I: Baseline (n = 2, 2, 2) | 1.34 (±0.94) | 1.09 (±0.057) | 1.83 (±0.403) |
| A-RE, Wave V/I: Change at Week 22 (n = 2, 1, 1) | 0.14 (±0.269) | 0.42 (±99999) | −1.48 (±99999)[a] |
| A-LE, Wave V/I: Baseline (n = 2, 2, 2) | 1.33 (±0.764) | 1.26 (±0.014) | 2.43 (±2.341) |
| A-LE, Wave V/I: Change at Week 22 (n = 2, 1, 1) | 0.37 (±0.453) | 0.28 (±99999) | −0.15 (±99999) |
| LTA-RE, Wave V/I: Baseline (n = 2, 2, 2) | 0.146 (±0.7733) | 0.086 (±0.0519) | 0.589 (±0.2227) |
| LTA-RE, Wave V/I: Change at Week 22 (n = 2, 1, 1) | 0.188 (±0.3011) | 0.336 (±99999) | −3.245 (±99999) |
| LTA-LE, Wave V/I: Baseline (n = 2, 2, 2) | 0.195 (±0.6093) | 0.231 (±0.0112) | 0.572 (±1.1791) |
| LTA-LE, Wave V/I: Change at Week 22 (n = 2, 1, 1) | 0.188 (±0.1787) | 0.202 (±99999) | −0.217 (±99999) |
| STA-RE, Wave V/I: Baseline (n = 2, 2, 2) | 1.116 (±0.4212) | 1.044 (±0.0271) | 1.347 (±0.1496) |
| STA-RE, Wave V/I: Change at Week 22 (n = 2, 1, 1) | 0.082 (±0.1409) | 0.188 (±99999) | −0.996 (±99999) |
| STA-LE, Wave V/I: Baseline (n = 2, 2, 2) | 1.128 (±0.3385) | 1.122 (±0.0063) | 1.449 (±0.8078) |
| STA-LE, Wave V/I: Change at Week 22 (n = 2, 1, 1) | 0.13 (±0.1448) | 0.119 (±99999) | −0.09 (±99999) |

[a]99999 signifies standard deviation not reported as there was only 1 evaluable subject The change from baseline in mean Auditory Brainstem Response (ABR) Log Transformed Latencies of study subjects was determined at week 22 (Table 22). ABR assessments were conducted under anesthesia and measured the electrical response evoked by acoustic stimuli as sound is processed along the auditory pathway. Data for change from baseline in ABR log-transformed latencies (LTL) by left and right ear were reported. The data are expressed as log transformed (latency [ms])+/−standard deviation.

TABLE 22

Change from Baseline in ABR: Log Transformed Latencies

| End point values (log transformed (latency [ms]) +/− SD | Group I (10 mg) | Group II (45 mg) | Group III (90 mg) |
|---|---|---|---|
| Number of subjects analyzed | 4 | 4 | 4 |
| LTL-RE, Wave I: Baseline (n = 3, 3, 3) | 0.54 (±0.1326) | 0.461 (±0.0956) | 0.567 (±0.0066) |
| LTL-RE, Wave I: Change at Week 22 (n = 3, 3, 3) | −0.006 (±0.2585) | 0.242 (±0.2791) | 0.179 (±0.4104) |
| LTL-RE, Wave III: Baseline (n = 3, 3, 3) | 1.387 (±0.1121) | 1.416 (±0.0483) | 1.409 (±0.0439) |
| LTL-RE, Wave III: Change at Week 22 (n = 3, 3, 2) | −0.019 (±0.0882) | 0.074 (±0.148) | −0.008 (±0.0108) |
| LTL-RE, Wave V: Baseline (n = 3, 3, 3) | 1.802 (±0.0461) | 1.838 (±0.0731) | 1.801 (±0.0374) |
| LTL-RE, Wave V: Change at Week 22 (n = 3, 3, 3) | −0.028 (±0.0794) | 0.044 (±0.0963) | 0.093 (±0.1529) |
| LTL-LE, Wave I: Baseline (n = 3, 3, 4) | 0.546 (±0.0769) | 0.518 (±0.0838) | 0.57 (±0.1268) |
| LTL-LE, Wave I: Change at Week 22 (n = 3, 3, 3) | −0.106 (±0.0653) | 0.088 (±0.1812) | 0.019 (±0.0927) |
| LTL-LE, Wave III: Baseline (n = 3, 3, 4) | 1.397 (±0.0804) | 1.438 (±0.0455) | 1.424 (±0.1213) |
| LTL-LE, Wave III: Change at Week 22 (n = 3, 3, 3) | −0.046 (±0.0394) | −0.02 (±0.0624) | 0.032 (±0.0657) |
| LTL-LE, Wave V: Baseline (n = 3, 3, 4) | 1.81 (±0.045) | 1.849 (±0.0658) | 1.831 (±0.0955) |
| LTL-LE, Wave V: Change at Week 22 (n = 3, 3, 4) | −0.034 (±0.0281) | 0.002 (±0.0494) | 0.036 (±0.0338) |

The change from baseline in mean Auditory Brainstem Response (ABR) Log Transformed Amplitude of study subjects was determined at week 22 (Table 23). ABR assessments were conducted under anesthesia and measured the electrical response evoked by acoustic stimuli as sound is processed along the auditory pathway. Data for change from baseline in ABR log-transformed amplitude (LTA) by left and right ear were reported. The data are expressed as log transformed (amplitude [mcV])+/−standard deviation.

TABLE 23

Change from Baseline in ABR: Log Transformed Amplitude

| End point values (log transformed (amplitude [mcV]) +/− SD) | Group I (10 mg) | Group II (45 mg) | Group III (90 mg) |
|---|---|---|---|
| Number of subjects analyzed | 4 | 4 | 4 |
| LTA-RE, Wave I: Baseline (n = 2, 3, 3) | −0.715 (±0.0867) | −0.893 (±0.2741) | −1.379 (±0.3627) |
| LTA-RE, Wave I: Change at Week 22 (n = 2, 3, 3) | −0.659 (±0.2456) | −0.76 (±0.8475) | −0.24 (±1.018) |
| LTA-RE, Wave III: Baseline (n = 2, 3, 3) | −1.168 (±0.4901) | −1.17 (±0.6224) | −1.527 (±0.589) |
| LTA-RE, Wave III: Change at Week 22 (n = 2, 3, 2) | −0.116 (±0.2867) | −0.549 (±0.4627) | −1.239 (±1.5038) |
| LTA-RE, Wave V: Baseline (n = 2, 3, 3) | −0.567 (±0.6834) | −0.792 (±0.2929) | −1.19 (±0.3631) |
| LTA-RE, Wave V: Change at Week 22 (n = 2, 3, 3) | −0.474 (±0.5435) | −0.214 (±0.3107) | −1.237 (±1.5458) |
| LTA-LE, Wave I: Baseline (n = 2, 3, 4) | −0.918 (±0.0708) | −0.875 (±0.4212) | −1.445 (±0.5468) |
| LTA-LE, Wave I: Change at Week 22 (n = 2, 3, 3) | −0.409 (±0.6445) | −0.268 (±0.8163) | 0.078 (±0.5695) |
| LTA-LE, Wave III: Baseline (n = 2, 3, 4) | −1.602 (±0.5149) | −1.057 (±0.4761) | −1.643 (±0.5086) |
| LTA-LE, Wave III: Change at Week 22 (n = 2, 3, 3) | 0.265 (±0.3271) | −0.374 (±0.7773) | 0.053 (±0.151) |
| LTA-LE, Wave V: Baseline (n = 2, 3, 4) | −0.726 (±0.5418) | −0.748 (±0.2486) | −1.372 (±0.5377) |
| LTA-LE, Wave V: Change at Week 22 (n = 2, 3, 4) | −0.217 (±0.4692) | −0.066 (±0.2771) | 0.006 (±0.3379) |

The change from baseline in mean Auditory Brainstem Response (ABR) Square-root Transformed Latencies of study subjects was determined at week 22 (Table 24). ABR assessments were conducted under anesthesia and measured the electrical response evoked by acoustic stimuli as sound is processed along the auditory pathway. Data for change from baseline in ABR square-root transformed latency (STL) by left and right ear were reported. The data are expressed as square-root transformed (latency [ms])+/−standard deviation.

TABLE 24

Change from Baseline in ABR: Square-root Transformed Latencies

| End point values (square-root transformed (latency [ms]) +/− SD) | Group I (10 mg) | Group II (45 mg) | Group III (90 mg) |
|---|---|---|---|
| Number of subjects analyzed | 4 | 4 | 4 |
| STL-RE, Wave I: Baseline (n = 3, 3, 3) | 1.312 (±0.0886) | 1.260 (±0.061) | 1.328 (±0.0044) |
| STL-RE, Wave I: Change at Week 22 (n = 3, 3, 3) | −0.002 (±0.1734) | 0.166 (±0.1935) | 0.145 (±0.3167) |
| STL-RE, Wave III: Baseline (n = 3, 3, 3) | 2.003 (±0.1123) | 2.030 (±0.0487) | 2.023 (±0.0446) |
| STL-RE, Wave III: Change at Week 22 (n = 3, 3, 2) | −0.021 (±0.0884) | 0.080 (±0.1593) | −0.008 (±0.0107) |
| STL-RE, Wave V: Baseline (n = 3, 3, 3) | 2.462 (±0.0571) | 2.508 (±0.091) | 2.461 (±0.0461) |
| STL-RE, Wave V: Change at Week 22 (n = 3, 3, 3) | −0.035 (±0.0974) | 0.056 (±0.1233) | 0.125 (±0.2057) |
| STL-LE, Wave I: Baseline (n = 3, 3, 4) | 1.315 (±0.05) | 1.297 (±0.055) | 1.332 (±0.0858) |
| STL-LE, Wave I: Change at Week 22 (n = 3, 3, 3) | −0.068 (±0.0425) | 0.059 (±0.1223) | 0.014 (±0.0608) |
| STL-LE, Wave III: Baseline (n = 3, 3, 4) | 2.012 (±0.0805) | 2.053 (±0.0464) | 2.04 (±0.1236) |
| STL-LE, Wave III: Change at Week 22 (n = 3, 3, 3) | −0.047 (±0.0403) | −0.019 (±0.0644) | 0.035 (±0.0709) |
| STL-LE, Wave V: Baseline (n = 3, 3, 4) | 2.473 (±0.0559) | 2.522 (±0.0824) | 2.5 (±0.1208) |
| STL-LE, Wave V: Change at Week 22 (n = 3, 3, 4) | −0.042 (±0.0354) | 0.002 (±0.0633) | 0.047 (±0.0438) |

The change from baseline in mean Auditory Brainstem Response (ABR) Square-root Transformed Amplitude of study subjects was determined at week 22 (Table 25). ABR assessments were conducted under anesthesia and measured the electrical response evoked by acoustic stimuli as sound is processed along the auditory pathway. Data for change from baseline in ABR square-root transformed amplitude (STA) by left and right ear were reported. The data are expressed as square-root transformed (amplitude [mcV])+/− standard deviation.

TABLE 25

Change from Baseline in ABR: Square-root Transformed Amplitude

| End point values (square-root transformed(amplitude [mcV]) +/− SD) | Group I (10 mg) | Group II (45 mg) | Group III (90 mg) |
|---|---|---|---|
| Number of subjects analyzed | 4 | 4 | 4 |
| STA-RE, Wave I: Baseline (n = 2, 3, 3) | 0.7 (±0.0303) | 0.644 (±0.0896) | 0.507 (±0.0933) |
| STA-RE, Wave I: Change at Week 22 (n = 2, 3, 3) | −0.193 (±0.0535) | −0.172 (±0.1615) | −0.044 (±0.2298) |
| STA-RE, Wave III: Baseline (n = 2, 3, 3) | 0.566 (±0.1374) | 0.575 (±0.171) | 0.479 (±0.1274) |
| STA-RE, Wave III: Change at Week 22 (n = 2, 3, 2) | −0.038 (±0.0838) | −0.122 (±0.0927) | −0.211 (±0.2317) |
| STA-RE, Wave V: Baseline (n = 2, 3, 3) | 0.775 (±0.2599) | 0.678 (±0.1022) | 0.557 (±0.0954) |
| STA-RE, Wave V: Change at Week 22 (n = 2, 3, 3) | −0.18 (±0.2183) | −0.069 (±0.1049) | −0.197 (±0.2547) |
| STA-LE, Wave I: Baseline (n = 2, 3, 4) | 0.632 (±0.0224) | 0.655 (±0.1437) | 0.499 (±0.133) |
| STA-LE, Wave I: Change at Week 22 (n = 2, 3, 3) | 0.101 (±0.1638) | −0.028 (±0.1961) | 0.006 (±0.1365) |
| STA-LE, Wave III: Baseline (n = 2, 3, 4) | 0.456 (±0.1162) | 0.601 (±0.1508) | 0.45 (±0.1131) |
| STA-LE, Wave III: Change at Week 22 (n = 2, 3, 3) | 0.057 (±0.068) | −0.085 (±0.1798) | 0.015 (±0.0422) |
| STA-LE, Wave V: Baseline (n = 2, 3, 4) | 0.709 (±0.1896) | 0.692 (±0.0873) | 0.518 (±0.1488) |
| STA-LE, Wave V: Change at Week 22 (n = 2, 3, 4) | −0.084 (±0.167) | −0.019 (±0.0956) | −0.004 (±0.0832) |

Example 2: Extended Clinical Trial of MPS IIIA Patients

A clinical trial was conducted using a recombinant human heparan-N-sulfatase (rhHNS) administered intrathecally (IT) via a surgically implanted intrathecal drug delivery device (IDDD) to subjects with MPS-IIIA to assess safety, tolerability, ascending dose and dose frequency. Subjects that completed the study described in Example 1 were invited to participate in the study described in the present example. Briefly, 12 subjects with MPS-IIIA were grouped by age; 7 subjects ranging in age from 2-11 years, 3 subjects ranging in age from 12-17 years and 2 subjects ranging in age from 18-64 years. Four subjects were included in each of three dosing groups. Group I received 10 mg of rhHNS via an IDDD monthly (i.e., every 28 days +/−7 days). Group II received 45 mg of rhHNS via an IDDD monthly (i.e., every 28 days +/−7 days). Group III received 45 mg of rhHNS via an IDDD every 14 days +/−2 days for a monthly total dose of 90 mg. Two subjects discontinued the study, within 70 weeks of treatment.

Immunogenicity

Figure 5A:
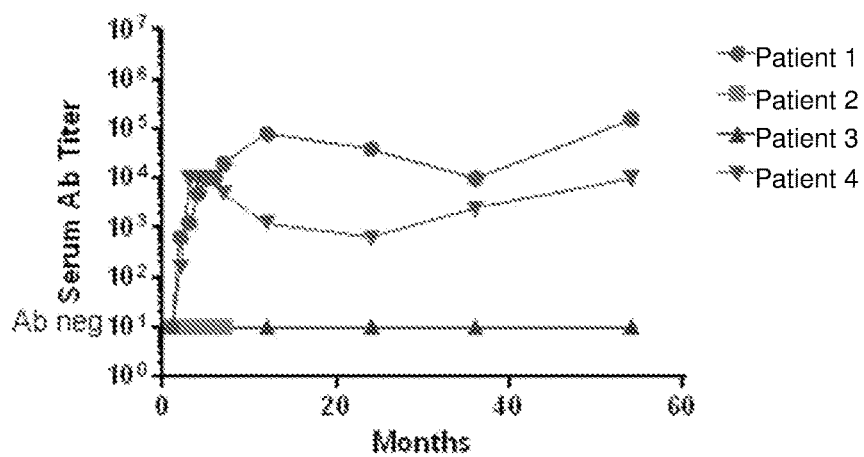
FIG. 5A shows the per patient anti-rhHNS antibody status in the cerebrospinal fluid (CSF) of study subjects receiving 10-45 mg/month. For plot purposes, Ab negative is assigned an artificial titer of 10.
Figure 5B:
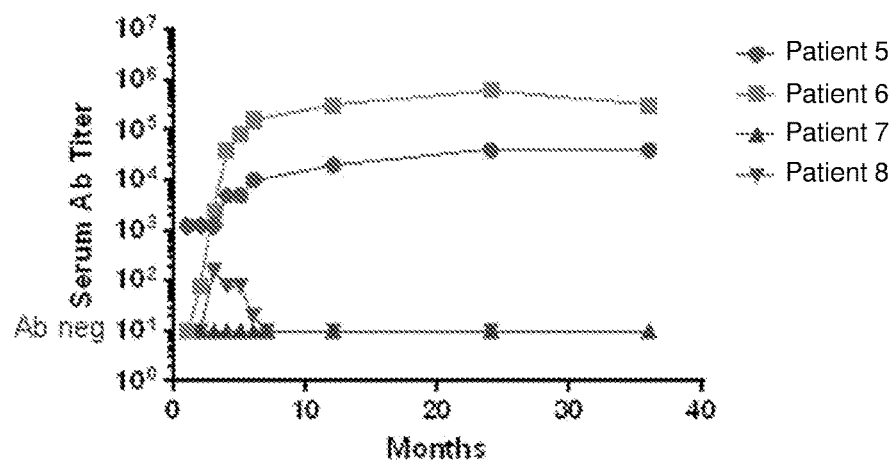
FIG. 5B shows the per patient anti-rhHNS antibody status in the cerebrospinal fluid (CSF) of study subjects receiving 45 mg/month. For plot purposes, Ab negative is assigned an artificial titer of 10.
Figure 5C:
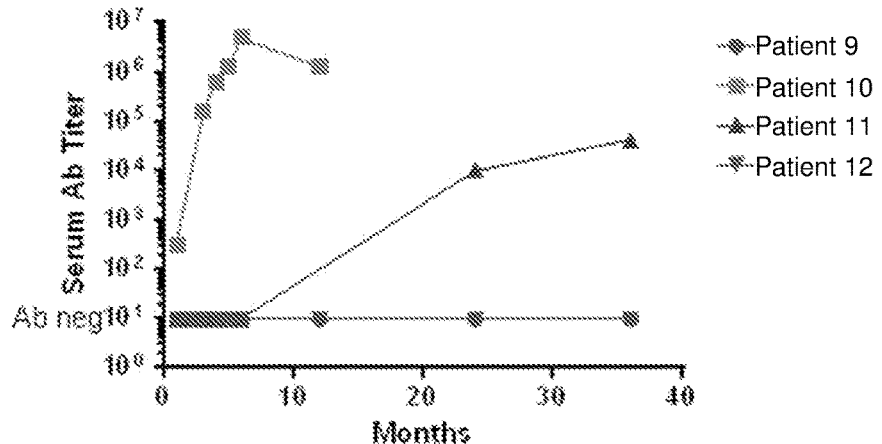
FIG. 5C shows the per patient anti-rhHNS antibody status in the cerebrospinal fluid (CSF) of study subjects receiving 90 mg/month. For plot purposes, Ab negative is assigned an artificial titer of 10.

The anti-rhHNS antibody status in the cerebrospinal fluid (CSF) of study subjects was determined periodically throughout the study (FIG. 5A-C). 50% patients (5/10) remain serum Ab negative after 36 to 54 months 2/12 patients are positive for CSF anti-rhHNS. For plot purposes, Ab negative is assigned an artificial titer of 10. Interestingly, the presence of anti-HNS antibodies was observed in each treatment group independent of the treatment dose (10-45 mg/month—FIG. 5A, 45 mg/month—FIG. 5B, 90 mg/month—FIG. 5C).

Assessment of Cognitive Performance

The change from baseline in development quotient (DQ) using Bayley Scales of Infant Development Third Edition (BSID-III) and Kaufman Assessment Battery for Children Second Edition (KABC-II) was determined at month 54 of the study (Table 26). BSID-III was used to assess the cognitive development, language (receptive and expressive), and motor development (fine and gross), of infants and toddlers, ages 0-42 months. KABC-II was an individually administered measure of the processing and reasoning abilities of children and adolescents between the ages of 3 and 18 years and is an alternative to BSID-III. BSID-III DQ score is based on the cognitive domain. The DQ score was calculated from the data obtained from either BSID-III/KABC-II mental age equivalent of the child in months divided by the calendar age in months (multiplied by 100 to give percentage points). The data are expressed as units as measured on the rating scale+/−standard deviation. Table 27 summarizes the changes from baseline in BSID-III/KABC-II Age-equivalent scores by rhHNS dose group after 54 months of treatment exposure.

TABLE 26

BSID-III/KABC-II DQ scores

| Time-point | Statistic | 10 mg (N = 4) | | 45 mg (N = 4) | | 90 mg (N = 4) | |
| --- | --- | --- | --- | --- | --- | --- | --- |
| | | Observed Value | Change from Baseline | Observed Value | Change from Baseline | Observed Value | Change from Baseline |
| Baseline | n | 2 | | 4 | | 4 | |
| | Mean | 51.91 | | 43.24 | | 51.87 | |
| | Std. Dev. | 27.292 | | 23.112 | | 36.095 | |
| | Median | 51.91 | | 40.28 | | 42.36 | |
| | Q1-Q3 | 32.61-71.21 | | 27.43-59.06 | | 29.65-74.08 | |
| | Min-Max | 32.6-71.2 | | 18.5-73.9 | | 19.3-103.4 | |
| Month54WK1D1 | n | 3 | 2 | 4 | 4 | 2 | 2 |
| | Mean | 25.63 | −17.97 | 24.25 | −18.99 | 55.20 | −16.50 |
| | Std. Dev. | 33.460 | 15.427 | 19.688 | 11.232 | 62.770 | 17.913 |
| | Median | 9.01 | −17.97 | 15.35 | −22.00 | 55.20 | −16.50 |
| | Q1-Q3 | 3.73-64.14 | −28.88--7.06 | 13.91-34.59 | −26.36--11.62 | 1081-99.58 | −29.17-3.83 |
| | Min-Max | 3.7-64.1 | −28.9--7.1 | 12.6-53.7 | −28.9--3.0 | 10.8-99.6 | −29.2--3.8 |

TABLE 27

BSID-III/KABC-II Age-equivalent scores

| Time-point | Statistic | 10 mg (N = 4) | | 45 mg (N = 4) | | 90 mg (N = 4) | |
| --- | --- | --- | --- | --- | --- | --- | --- |
| | | Observed Value | Change from Baseline | Observed Value | Change from Baseline | Observed Value | Change from Baseline |
| Baseline | n | 2 | | 4 | | 4 | |
| | Mean | 66.00 | | 35.17 | | 60.90 | |
| | Std. Dev. | 66.468 | | 21.678 | | 60.210 | |
| | Median | 66.00 | | 35.75 | | 37.00 | |
| | Q1-Q3 | 19.00-113.00 | | 16.50-53.83 | | 21.50-100.30 | |
| | Min-Max | 19.0-113.0 | | 14.0-55.2 | | 21.0-148.6 | |
| Month54 WK1D1 | n | 3 | 2 | 4 | 4 | 2 | 2 |
| | Mean | 52.07 | 2.60 | 35.33 | 0.17 | 101.10 | 16.30 |
| | Std. Dev. | 70.663 | 24.890 | 26.977 | 6.632 | 127.421 | 37.194 |
| | Median | 19.00 | 2.60 | 32.67 | −2.08 | 101.10 | 16.30 |
| | Q1-Q3 | 4.00-133.20 | −15.00-20.20 | 12.50-58.17 | −4.00-4.33 | 11.00-191.20 | −10.00-42.60 |
| | Min-Max | 4.0-133.2 | −15.0-20.2 | 11.0-65.0 | −5.0-9.8 | 11.0-191.2 | −10.0-42.6 |

Figure 6A:
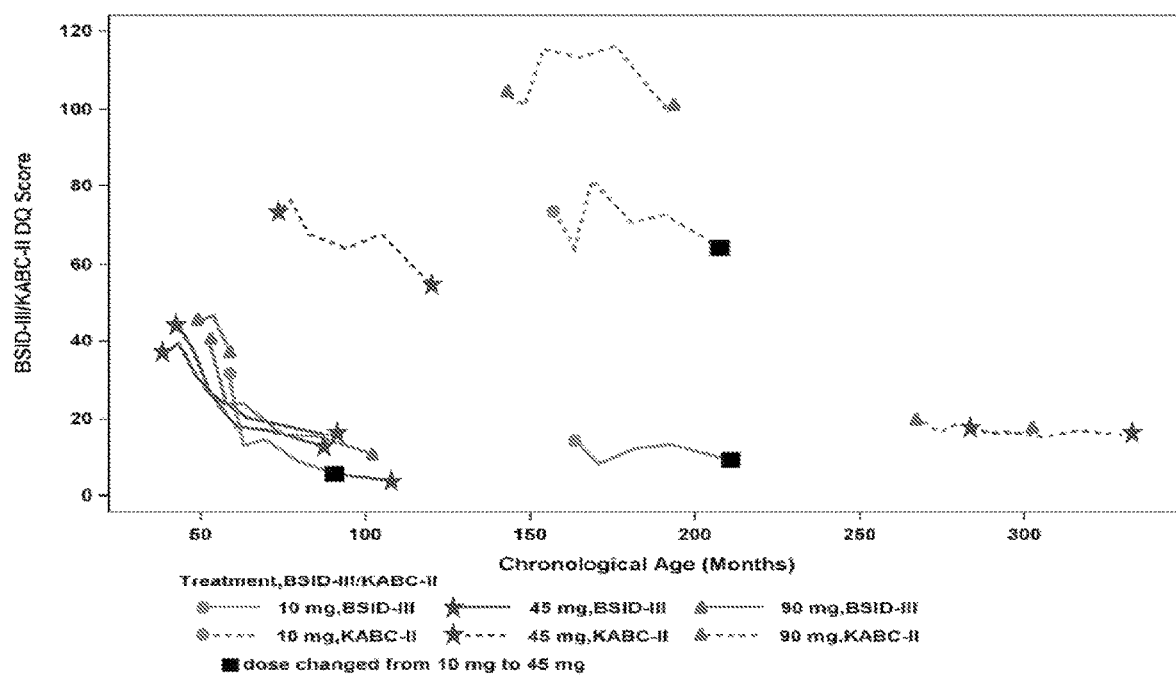
FIG. 6 shows BSID-III/KABC-II spaghetti plots of cognitive DQ (FIG. 6A) and age-equivalent (FIG. 6B) score by chronological age demonstrating time trends of individual subjects within the same plot. The treatment groups show a stabilization or reduction of decline over time.
Figure 6B:
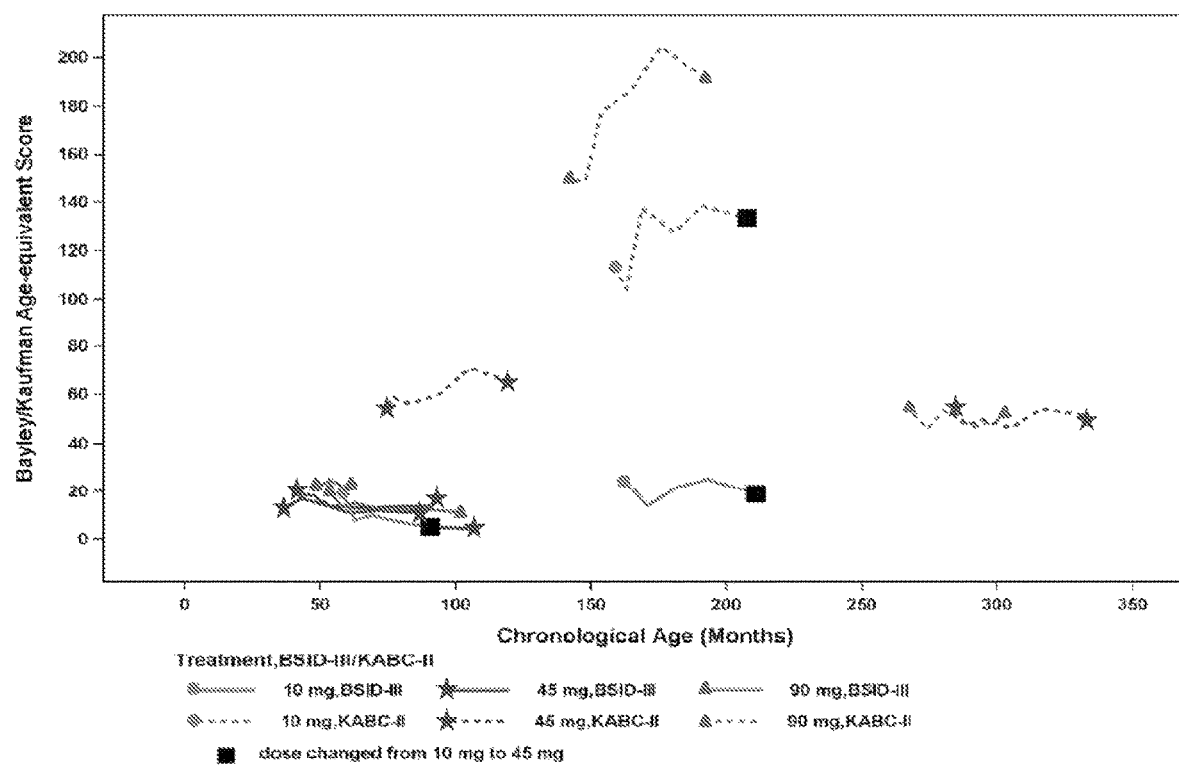
Figure 7A:
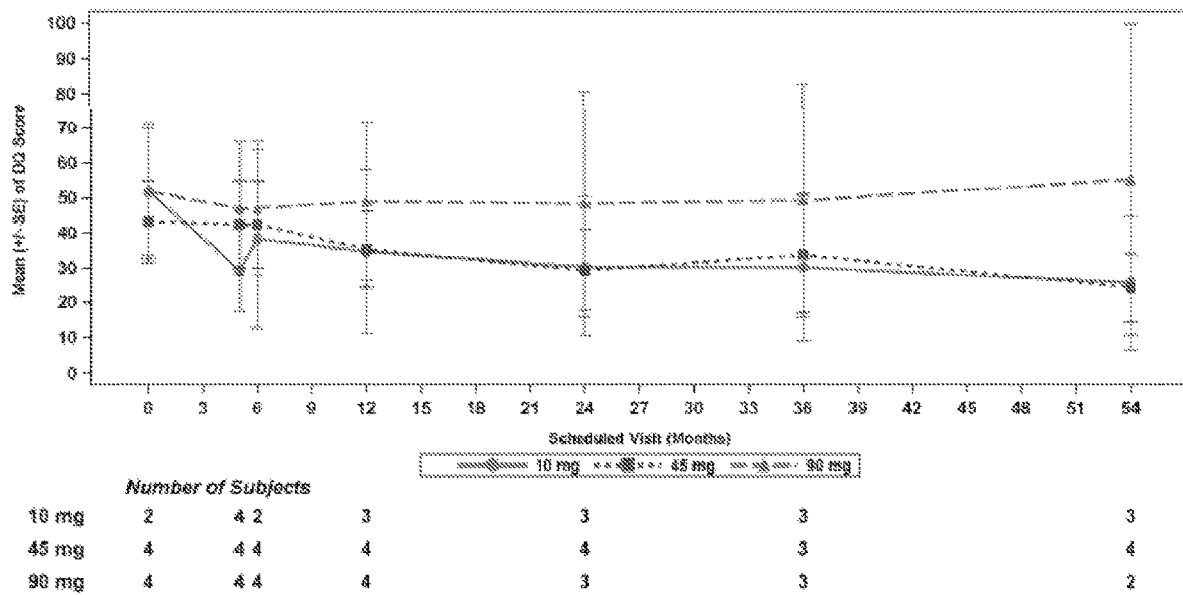
FIG. 7 shows the mean DQ (FIG. 7A) and AE (FIG. 7B) of all subjects over 54 months demonstrating the long term stability of cognitive function with rhHNS treatment.
Figure 7B:
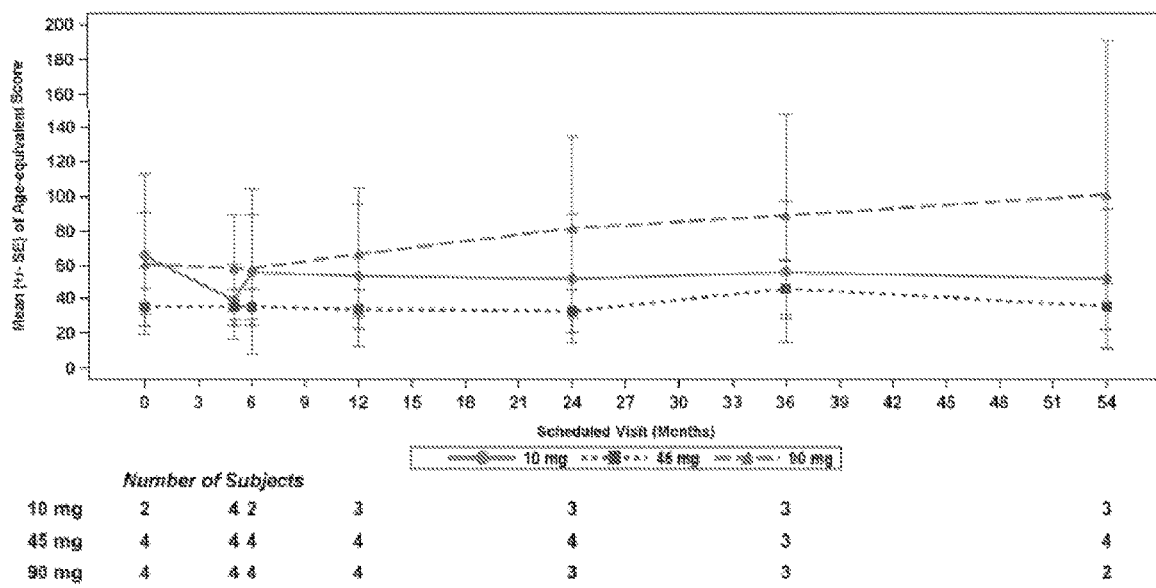

The BSID-III/KABC-II spaghetti plots of cognitive DQ (FIG. 6A) and age-equivalent (AE) score by chronological age help to visualize the trajectories or time trends of six individual subjects within the same plot. As shown in FIGS. 6A and 6B, the treatment groups show a stabilization or reduction of decline over time. The mean DQ (FIG. 7A) and AE (FIG. 7B) of all subjects over 54 months demonstrates the long term stability of cognitive function with rhHNS treatment.

Biomarkers

Figure 8:
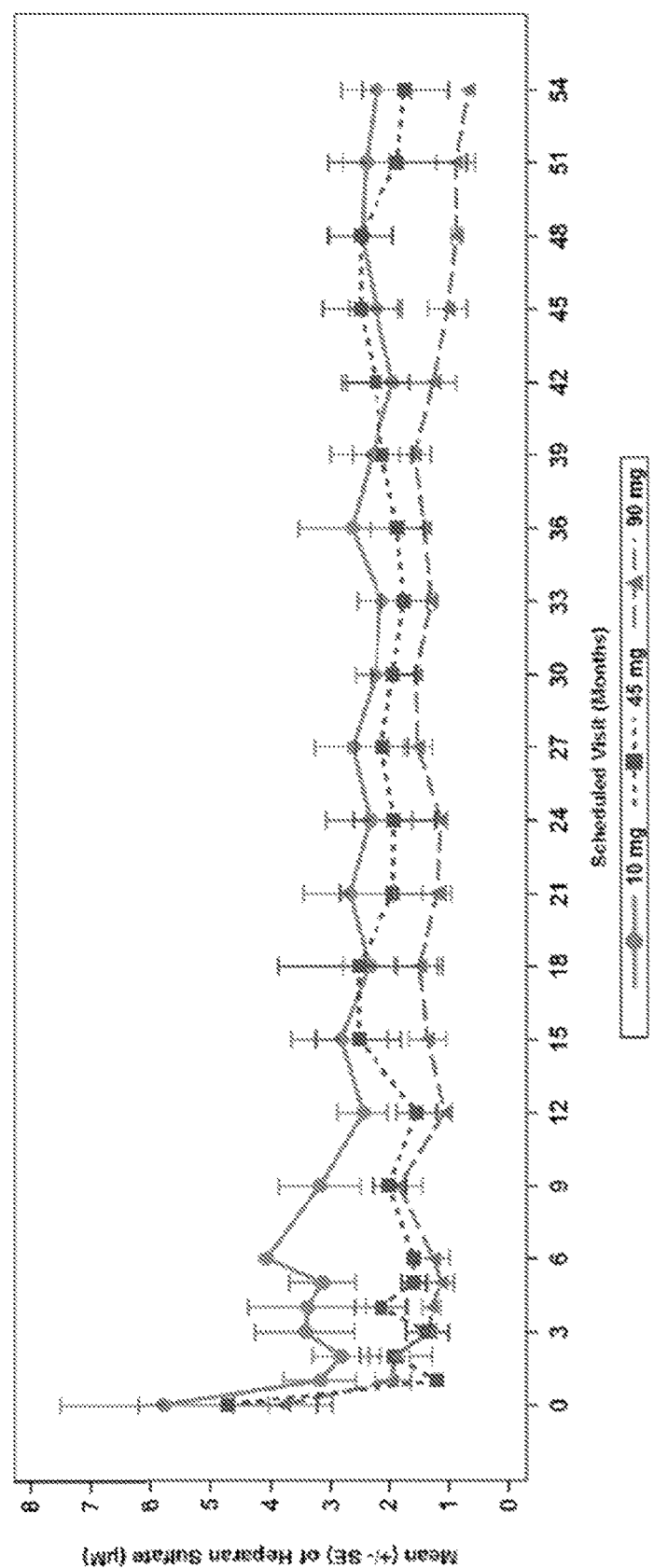
FIG. 8 shows cerebrospinal HS levels averaged by treatment group. The data are expressed as HS concentration (μM)+/−standard error.

Heparan sulfate (HS) is the primary accumulating metabolite in Sanfilippo Syndrome Type A. The level of the glycosaminoglycan (GAG) heparan sulfate in CSF was measured at various time points during the study as an important biomarker to indicate in vivo activity of rhHNS in the central nervous system. The change in total heparan sulfate (HS) and heparan sulfate derivatives (HSD) concentrations from baseline were measured in the cerebrospinal fluid (CSF) of study subjects at three month intervals for a total of 54 months. Levels of total heparan sulfate (SPTHS) and its GAG derivatives (i.e., by a non-reducing end assay, SPNREA) were evaluated using a Sensi-Pro (SP) high performance lipid chromatography based assay (Zacharon). As shown in FIG. 8, all treatment groups showed a decrease in HS levels in the CSF. The data are expressed as HS concentration (μM)+/−standard error.

Figure 9A:
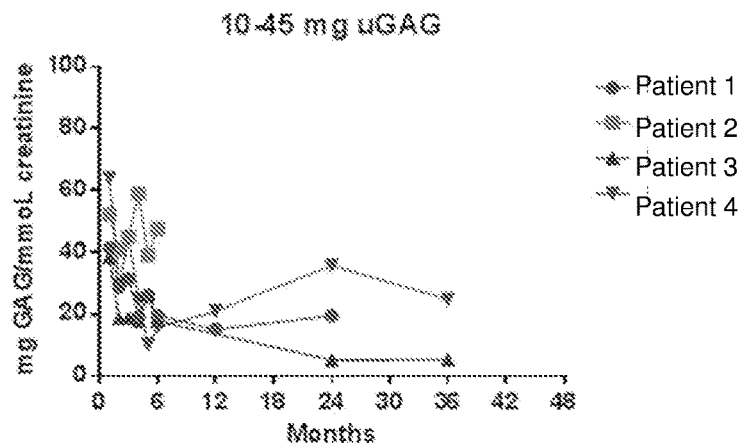
FIG. 9 shows urinary glycosaminoglycan (GAG) levels (mg) normalized for mmol of urine creatinine. The mean values of urine GAG are displayed over time and by dose group i (10-45 mg/month—FIG. 9A, 45 mg/month—FIG. 9B, 90 mg/month—FIG. 9C). By patient urine GAG levels were assessed by dye binding colorimetric assay to detect total GAG.
Figure 9B:
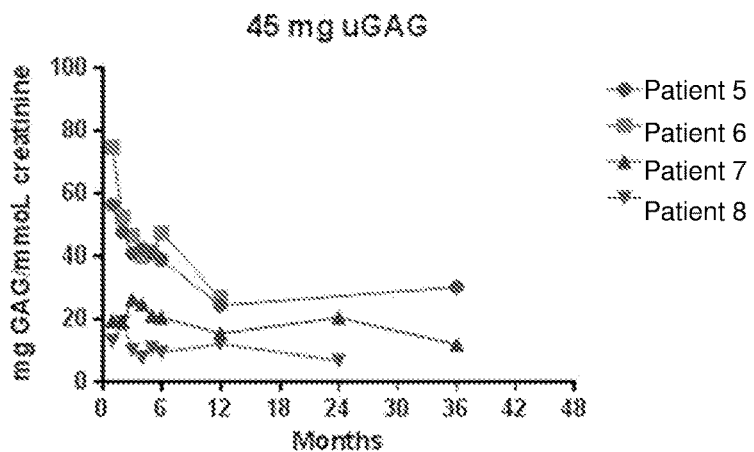
Figure 9C:
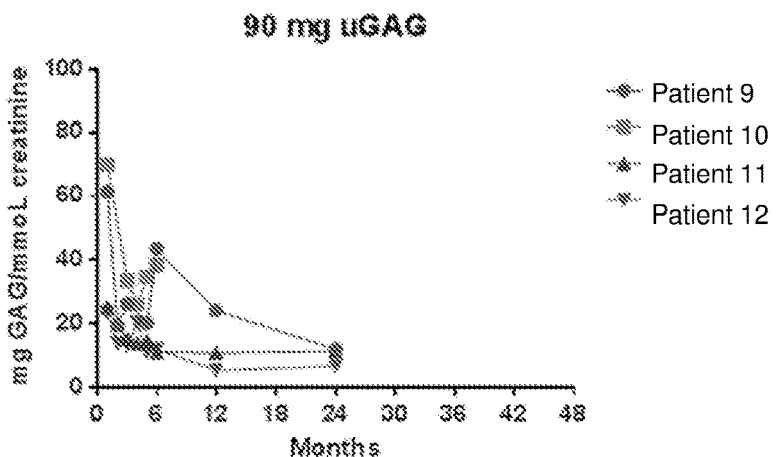

Urine glycosaminoglycan (GAG) levels (mg) were normalized for mmol of urine creatinine. The mean values of urine GAG are displayed over time and by dose group in FIG. 9 (10-45 mg/month—FIG. 9A, 45 mg/month—FIG. 9B, 90 mg/month—FIG. 9C). By patient urine GAG levels were assessed by dye binding colorimetric assay to detect total GAG. After 24-36 months of treatment, reduction in urinary GAG levels was observed for individual subjects in all treatment groups.

Biomarker Profile Analysis was performed to evaluate an initial exploratory neurological and inflammatory biomarker profile by multiplex immunoassay platform and aptamer-based technology. 15 CSF biomarker candidates were assessed using a multiplex immunoassay panel including 119 biomarkers. 8/15 biomarkers were significantly higher in San A patients compared to age-matched surrogate controls.

CSF HS levels were markedly reduced after ERT and remain reduced in all treated patients, including patients with high Ab titers. Urinary GAG levels were reduced in most patients CSF pTau levels were slightly reduced after ERT (data not shown). Exploratory biomarker studies identify eight CSF biomarkers were elevated in San A patients.

Example 3: Clinical Trial of MPS IIIA Patients to Assess Dosing Regimen

A clinical trial was conducted using a recombinant human heparan-N-sulfatase (rhHNS) administered intrathecally (IT) via a surgically implanted intrathecal drug delivery device (IDDD) to human subjects with MPS-IIIA at a dose of 45 mg administered every 2 weeks (Q2W) (ie, every 14 days) or 45 mg administered every 4 weeks (Q4W) (ie, every 28 days) for 48 weeks. rhHNS was administered intrathecally (IT) by an indwelling intrathecal drug delivery device (IDDD) or via lumbar puncture (LP). Subjects were divided into three treatment groups as follows; Group 1 included seven subjects receiving 45 mg rhHNS every 2 weeks; Group 2 included seven subjects receiving 45 mg rhHNS every 4 weeks.

This open-label, randomized, parallel group, controlled, multicenter study was designed to evaluate the efficacy and safety of 45 mg rhHNS administered IT Q2W and 45 mg of rhHNS administered IT Q4W via an IDDD versus no treatment in patients at a relatively early stage of MPS IIIA disease. Cognitive assessments, which support the primary objective of the trial, were performed by assessors who were blinded to the treatment assignment of the subject. The primary objective of this study was to assess the potential clinical efficacy of rhHNS administered via a surgically implanted IDDD in patients with MPS IIIA. Efficacy was measured as a meaningful amelioration in the progression of cognitive decline, and will be measured using the Bayley Scales of Infant and Toddler Development, 3rd Edition (BSID-III).

The secondary objectives were to evaluate the safety and tolerability of rhHNS. Assess the effect of rhHNS administration on BSID-III age-equivalent and development quotient (DQ) scores. The effect of rhHNS on adaptive behavioral function was assessed by Vineland Adaptive Behavior Scales, Second Edition (VABS-II). Furthermore, the effect of rhHNS treatment on the total cortical grey matter volume was assessed by volumetric MRI of the brain. Additionally, the effect of rhHNS treatment on biomarkers such as concentration of glycosaminoglycans (GAG) in CSF and urine was evaluated. The pharmacokinetics of rhHNS in cerebrospinal fluid (CSF) and serum was also investigated.

Pharmacokinetic Assessment

Figure 10A:
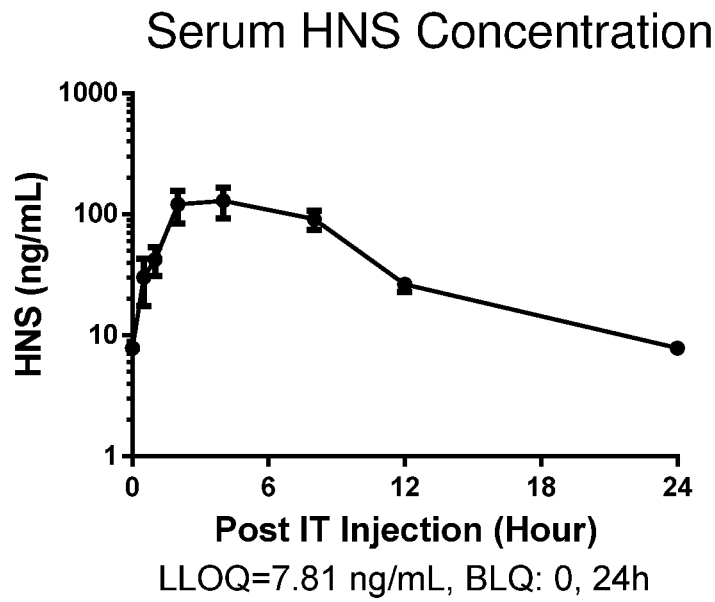
FIG. 10 shows pharmacokinetic dose-dependent serum (FIG. 10A) and CSF (FIG. 10B) HNS concentration after 45 mg rhHNS IT injection.
Figure 10B:
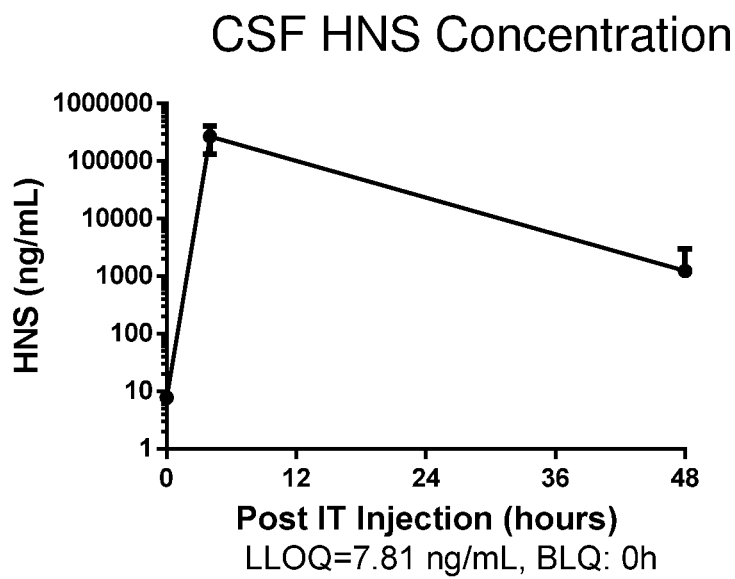

The determination of rhHNS concentration in serum and CSF for subjects randomized to receive rhHNS, blood samples were collected and determination of PK parameters after intrathecal administration was performed. CSF samples were collected immediately prior to IT dosing and times for measurement of CSF concentrations of rhHNS. CSF samples from some latter time points will also be assayed for GAGs, to permit assessment of the early PD response. FIGS. 10A and 10B show dose-dependent serum and CSF PK after IT injection. Serum peak HNS concentration is ~1000 folds less than CSF HNS concentration. Serum HNS levels were below 7.8 ng/mL within 24 h. The mean HNS concentrations were 272 μg/mL and 1.24 μg/mL at 4 h and 48 h post injection, respectively.

Immunogenicity

The anti-rhHNS antibody status in the serum and cerebrospinal fluid (CSF) of study subjects was monitored throughout the study (FIG. 11A-D). Subjects dosed every 2 weeks developed higher antibody conversion rate and higher antibody titers. For plot purposes, Ab negative is assigned an artificial titer of 10. Interestingly, the presence of anti-HNS antibodies was observed in both treatment groups (45 mg/14 days—FIG. 11A, 11C, 45 mg/28 days—FIG. 11B, 11D).

Pharmacodynamic Biomarker Assessments

CSF and urine samples were obtained to measure concentration of GAG (i.e. heparan sulfate) in addition to the CSF PD samples taken at the time of PK sampling. The identification of novel biomarkers is an exploratory objective of this clinical trial. A biomarker, as discussed herein is defined as a characteristic that is objectively measured and evaluated as an indicator of the MPS IIIA pathogenic process, or a pharmacologic response to experimental therapy with rhHNS. The conduct of a clinical trial in an extremely rare disease such as MPS IIIA provides a unique opportunity to collect samples for biomarker research, which may lead to the identification of novel markers and afford potential insights into the pathophysiology of MPS IIIA and its response to therapy. Samples collected during the duration of this study are used for further biomarker evaluation (data not shown).

Figure 12A:
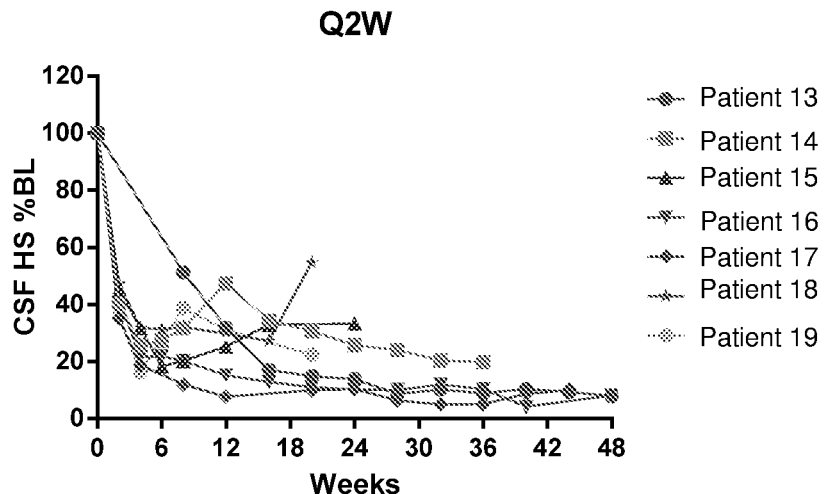
FIG. 12 CSF shows change in CSF heparan sulfate levels normalized to the Day 0 baseline (BL) level of each subject receiving 45 mg every 2 weeks (FIG. 12A) or every 4 weeks (FIG. 12B).
Figure 12B:
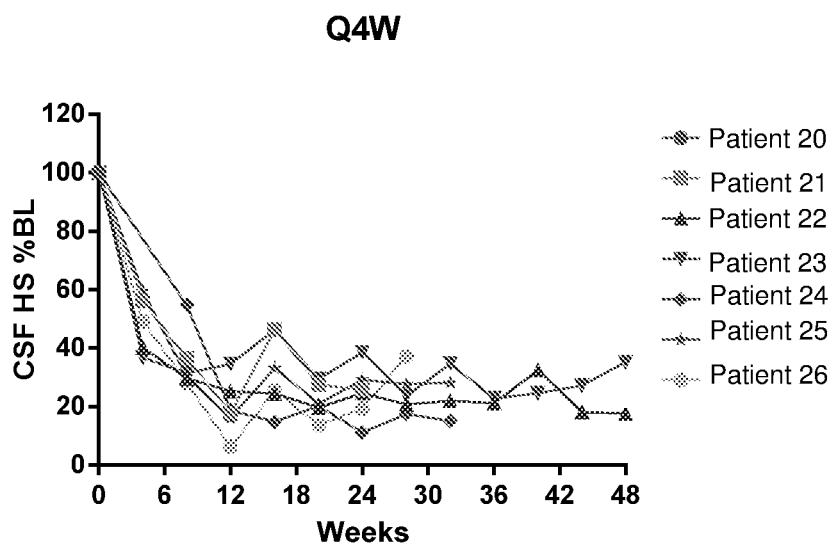

CSF heparan sulfate was normalized to the Day 0 baseline (BL) level CSF HS level of each subject as shown in FIGS. 12A and 12B. Q2W, Q4W: CSF HS levels in all patients was markedly reduced after first dosing and maintained at the low level. A fluctuation of CSF HS reduction was observed in patients with high serum Ab titers and positive for CSF Ab. CSF HS levels in untreated controls were 82% of BL at week 24 and 89% of BL at week 48 (data not shown).

Figure 13A:
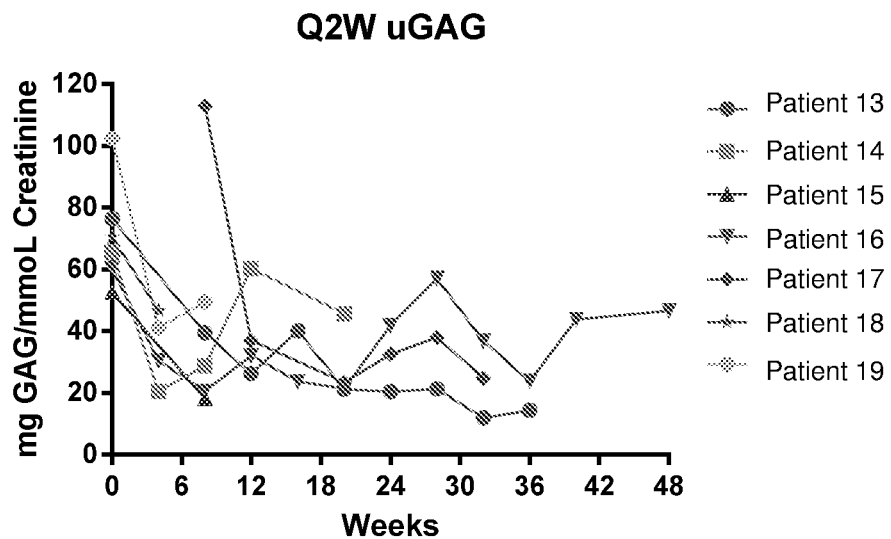
FIG. 13 shows urinary glycosaminoglycan (GAG) levels (mg) normalized for mmol of urine creatinine. The mean values of urine GAG are displayed over time and by dose group in FIGS. 13A (45 mg/14 days) and 13B (45 mg/28 days).
Figure 13B:
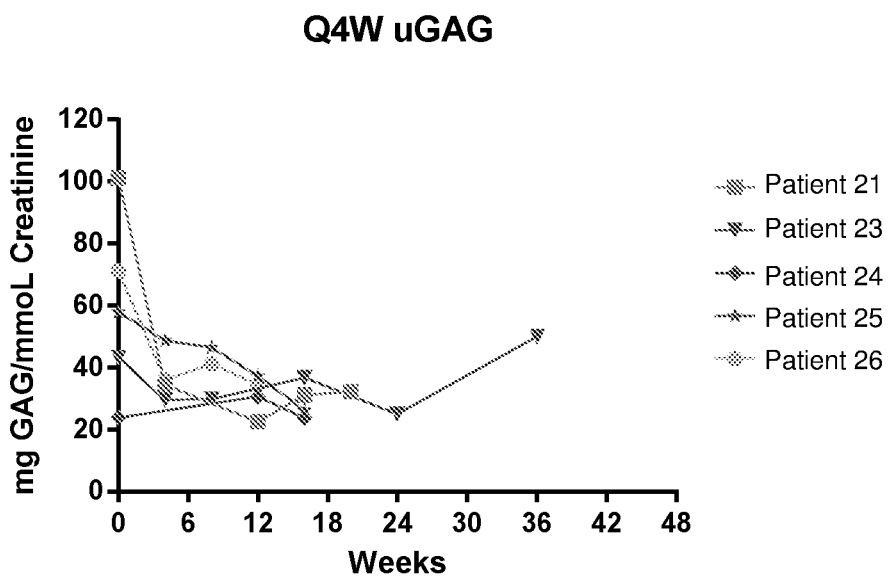

Urine glycosaminoglycan (GAG) levels (mg) were normalized for mmol of urine creatinine. The mean values of urine GAG are displayed over time and by dose group in FIGS. 13A (45 mg/14 days) and 13B (45 mg/28 days). By patient urine GAG levels were assessed by dye binding colorimetric assay to detect total GAG. After 48 weeks of treatment, reduction in urinary GAG levels was observed for individual subjects in all treatment groups.

Efficacy Assessments:

Primary efficacy assessment will be cognitive function over time expressed as a Developmental Quotient assessed by neurocognitive testing, accomplished by using the BSID-III. Additional efficacy variables to be assessed included: adaptive behavioral function over time, assessed by VABS-II, the total cortical grey matter volume, assessed by MRI, as well as the exploratory endpoints of: quality of life score (assessed using the Infant Toddler QoL Questionnaire); the Children's Sleep Habits Questionnaire; liver and spleen size, assessed by MRI; and the concentrations of exploratory biomarkers in CSF, serum, and urine.

Neurocognitive and Developmental Assessments

The study methodology included standardized neurodevelopmental assessments to provide a quantifiable measure of subject neurodevelopmental status (see Table 28). The assessments are estimated to last between 2 and 4 hours and were conducted prior to any invasive procedures, such as blood draws, and prior to sedation or anesthesia.

TABLE 28

Neurodevelopmental Assessments Tests

| Cognitive Test or Scale | Scale Developmental or Cognitive Domain(s) |
| --- | --- |
| Bayley Scales of Infant and Toddler Development, Third Edition (BSID-III) | Summary score and sub-domains: Cognitive Motor Social/Emotional Language |
| ADAPTIVE BEHAVIOR | |
| Vineland Adaptive Behavior Scales, Second Edition (VABS II)13 | Communication Daily Living Socialization Motor Skills |

EQUIVALENTS

Those skilled in the art will recognize, or be able to ascertain using no more than routine experimentation, many equivalents to embodiments of the inventions described herein. The scope of the present invention is not intended to be limited to the above Description, but rather is as set forth in the following claims. All publications cited in this application are incorporated by reference in their entireties.

I claim:

1. A method of treating Sanfilippo Syndrome Type A (MPS IIIA) comprising a step of administering intrathecally to a subject in need of treatment a recombinant heparan N-sulfatase (HNS) enzyme at a therapeutically effective dose and an administration interval for a period sufficient to stabilize or reduce decline of cognitive function relative to baseline, wherein the administration interval is at least once every month;

wherein the therapeutically effective dose is or is greater than 45 mg per dose;

and wherein the period is at least 54 months.

2. The method of claim 1 wherein the administration is through intermittent or continuous access to an implanted intrathecal drug delivery device (IDDD).

3. The method of claim 1, wherein the cognitive function is assessed by the Bayley Scales of Infant Development (Third Edition) (BSID-III) instrument.

4. The method of claim 3, wherein the intrathecal administration of the recombinant HNS enzyme results in stabilization of a BSID-III development quotient relative to baseline.

5. The method of claim 1, wherein the cognitive function is assessed by the Kaufman Assessment Battery for Children (Second Edition) (KABC-II) instrument.

6. The method of claim 5, wherein the intrathecal administration of the recombinant HNS enzyme results in stabilization of a KABC-II development quotient relative to baseline.

7. The method of claim 1, wherein the cognitive function is assessed by the Vineland Adaptive Behavior Scales Second Edition (VABS-II) test.

8. The method of claim 7, wherein the intrathecal administration of the recombinant HNS enzyme results in stabilization of a VABS-II development quotient relative to baseline.

9. The method of claim 1, wherein the subject in need of treatment is at least 3 years old, at least 12 years old, or at least 18 years old.

10. The method of claim 1, wherein the method further comprises a step of adjusting the dose and/or administration interval for intrathecal administration based on improvement, stabilization or reduction in decline of cognitive function, relative to baseline.

11. The method of claim 10, wherein the step of adjusting comprises increasing the therapeutic effective dose for intrathecal administration if the improvement, stabilization or reduction in decline of cognitive function is unaltered or decreased relative to baseline after 4 doses.

12. The method of claim 1, wherein the intrathecal administration does not require an immunosuppressant.

13. The method of claim 1, wherein the intrathecal administration is performed in conjunction with intravenous administration of the recombinant HNS enzyme.

14. The method of claim 1, wherein the subject has cognitive impairment.

* * * * *